US012790615B2

(12) United States Patent
Chakrabarti et al.

(10) Patent No.: US 12,790,615 B2
(45) Date of Patent: Nov. 10, 2026

(54) COMPOSITIONS AND METHODS FOR SILENCING KRAS

(71) Applicant: Nanothera Biosciences, Inc., Mt. Laurel, NJ (US)

(72) Inventors: Raj Chakrabarti, Moorestown, NJ (US); Robert J. Lee, Mt. Laurel, NJ (US); Thomas Delacroix, Vert le Petit (FR); Gauthier Errasti, Vert le Petit (FR); Coralie Lebleu, Vert le Petit (FR); Anisha Ghosh, Mt. Laurel, NJ (US); Ioanna Petrounia, Mt. Laurel, NJ (US)

(73) Assignee: Nanothera Biosciences, Inc., Mt. Laurel, NJ (US)

( * ) Notice: Subject to any disclaimer, the term of this patent is extended or adjusted under 35 U.S.C. 154(b) by 473 days.

(21) Appl. No.: 17/970,405

(22) Filed: Oct. 20, 2023

(65) Prior Publication Data

US 2024/0060069 A1 Feb. 22, 2024

(51) Int. Cl.
*C12N 15/113* (2010.01)

(52) U.S. Cl.
CPC ...... *C12N 15/1135* (2013.01); *C12N 2310/14* (2013.01); *C12N 2310/141* (2013.01); *C12N 2320/32* (2013.01); *C12N 2320/34* (2013.01)

(58) Field of Classification Search
CPC ............. A61K 31/713; C12N 15/1135; C12N 2310/14; C12N 2310/315; C12N 2310/321; C12N 2320/32; C12N 2320/34
See application file for complete search history.

(56) References Cited

U.S. PATENT DOCUMENTS

2020/0407725 A1 12/2020 Sathyanarayanan et al.

FOREIGN PATENT DOCUMENTS

| | | | | |
|---|---|---|---|---|
| EP | 4000638 | A1 * | 5/2022 | ......... C12N 15/1135 |
| WO | WO-2017223135 | A1 * | 12/2017 | ........... A61K 9/1271 |
| WO | 2018170333 | A1 | 9/2018 | |
| WO | 2021107160 | A1 | 6/2021 | |

OTHER PUBLICATIONS

Acunzo et al. (Proceedings of the National Academy of Sciences (PNAS), vol. 114, No. 21, May 23, 2017 (May 23, 2017), pp. E4203-E4212, plus Supplemental Information).*
Papke et al. (ACS Pharmacol. Transl.Sci.2021,4,703-712, plus Supplemental Information).*
International Search Report and Written Opinion corresponding to PCT/US22/47291 mailed Nov. 3, 2023, 13 pages.

(Continued)

*Primary Examiner* — Terra C Gibbs
(74) *Attorney, Agent, or Firm* — J. Clinton Wimbish; Maynard Nexsen PC

(57) ABSTRACT

The invention relates to the inhibition of mutant KRAS sequences using RNA interference (RNAi). In addition, the present invention provides lipid nanoparticle (LNP) compositions as delivery vehicles for RNAi agents and methods of administering them for therapeutic purposes.

15 Claims, 36 Drawing Sheets

Specification includes a Sequence Listing.

(56) References Cited

OTHER PUBLICATIONS

Brennecke et al., Principles of MicroRNA-Target Recognition, pp. 0404-0418, PLoS Biology vol. 3, issue 3. Online. Feb. 15, 2005; [retrieved Mar. 13, 2023] Retrieved from the internet:< https://joumals.plos.org/plosbiology/article?id=10.1371/journal.pbio.0030085>; abstract; p. 0404, col. 2, last Paragraph; p. 0405, col. 1, first paragraph; p. 0405, col. 1, paragraph 3; p. 0408, col. 1, paragraph 1; p. 0412, col. 2, paragraph 2; DOI: 10.1371/journal.pbio.0030085.

Correia De Sousa et al., Deciphering miRNAs' Action through miRNA Editing, pp. 1-22, International Journal of Molecular Sciences, vol. 20, Online. Nov. 12, 2019; [retrieved Mar. 13, 2023] Retrieved from the Internet <https://www.mdpi.com/1422-0067/20/24/6249>; abstract; DOI: 10.3390/ijms20246249.

* cited by examiner

A

| 25nM | amiRscr | amiR6T | amiR6-11CU | amiR6-10GA | G12Dsi | sikras14 | EFTX-D1 | G12Dsi-4CA |
|---|---|---|---|---|---|---|---|---|
| pERK | 1 | 0.64 | 0.81 | 0.55 | 0.93 | 1.18 | 0.60 | 0.42 |
| KRAS (L-blot) | 1 | 1.17 | 0.96 | 0.31 | 0.39 | 1.31 | 0.73 | 0.39 |
| KRAS (R-blot) | 1 | 1.09 | 0.93 | 0.61 | 0.52 | 0.87 | 0.51 | 0.35 |

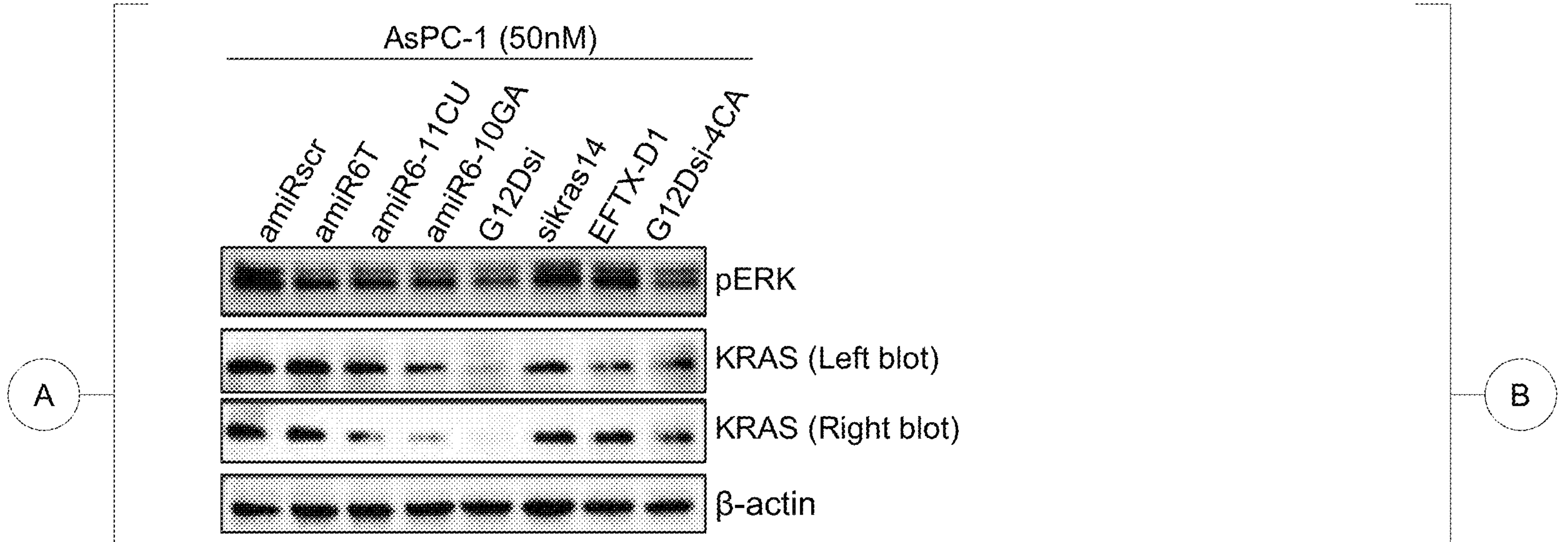
| 50nM | amiRscr | amiR6T | amiR6-11CU | amiR6-10GA | G12Dsi | sikras14 | EFTX-D1 | G12Dsi-4CA |
|---|---|---|---|---|---|---|---|---|
| pERK | 1 | 0.46 | 0.37 | 0.43 | 0.36 | 0.41 | 0.69 | 0.46 |
| KRAS (L-blot) | 1 | 0.61 | 0.43 | 0.33 | 0.13 | 0.25 | 0.33 | 0.28 |
| KRAS (R-blot) | 1 | 0.76 | 0.46 | 0.50 | 0.33 | 0.53 | 0.96 | 0.57 |
FIG. 8 (Continued...)

B
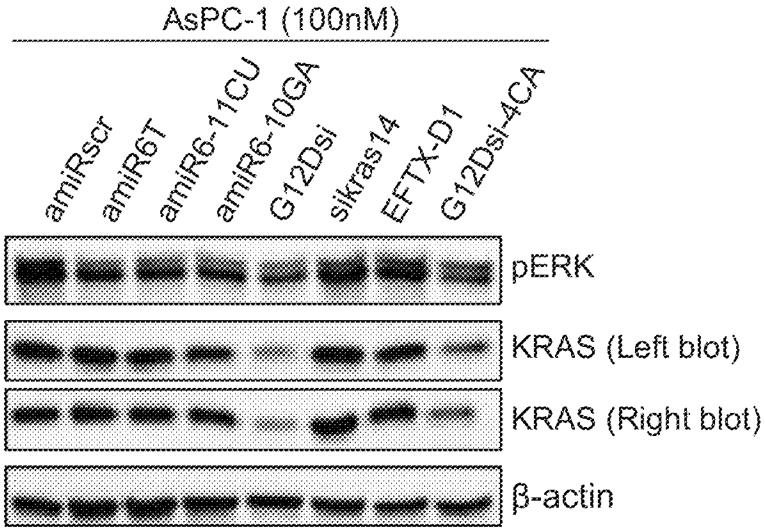
| 100nM | amiRscr | amiR6T | amiR6-11CU | amiR6-10GA | G12Dsi | sikras14 | EFTX-D1 | G12Dsi-4CA |
|---|---|---|---|---|---|---|---|---|
| pERK | 1 | 0.50 | 0.44 | 0.46 | 0.53 | 0.88 | 1.05 | 0.69 |
| KRAS (L-blot) | 1 | 0.74 | 0.49 | 0.41 | 0.21 | 1.04 | 0.93 | 0.41 |
| KRAS (R-blot) | 1 | 0.89 | 0.70 | 0.64 | 0.28 | 1.64 | 1.44 | 0.58 |
Fig. 8 (Continued...)

| 25nM | amiRscr | amiR6T | amiR6-11CU | amiR6-10GA | G12Dsi | sikras14 | EFTX-D1 | G12Dsi-4CA |
|---|---|---|---|---|---|---|---|---|
| pERK | 1 | 0.81 | 0.79 | 0.89 | 1.12 | 0.86 | 0.46 | 0.75 |
| KRAS (L-blot) | 1 | 1.30 | 1.23 | 1.25 | 0.70 | 1.71 | 1.23 | 1.30 |
| KRAS (R-blot) | 1 | 1.23 | 1.30 | 1.71 | 0.73 | 1.45 | 1.21 | 1.94 |

C
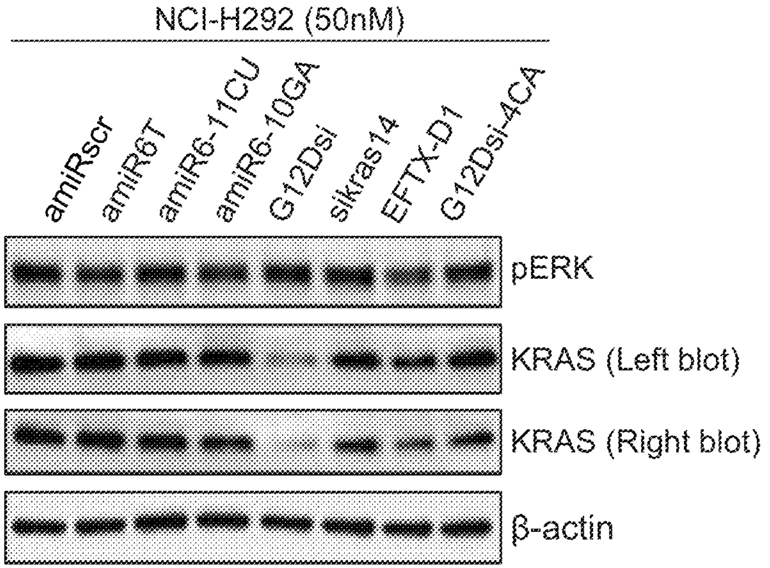
| 50nM | amiRscr | amiR6T | amiR6-11CU | amiR6-10GA | G12Dsi | sikras14 | EFTX-D1 | G12Dsi-4CA |
|---|---|---|---|---|---|---|---|---|
| pERK | 1 | 0.85 | 0.68 | 0.88 | 1.33 | 1.51 | 0.73 | 0.90 |
| KRAS (L-blot) | 1 | 1.08 | 0.55 | 0.69 | 0.23 | 0.74 | 0.41 | 0.72 |
| KRAS (R-blot) | 1 | 1.38 | 0.68 | 0.70 | 0.20 | 0.65 | 0.35 | 0.55 |
D
FIG. 9 (Continued...)

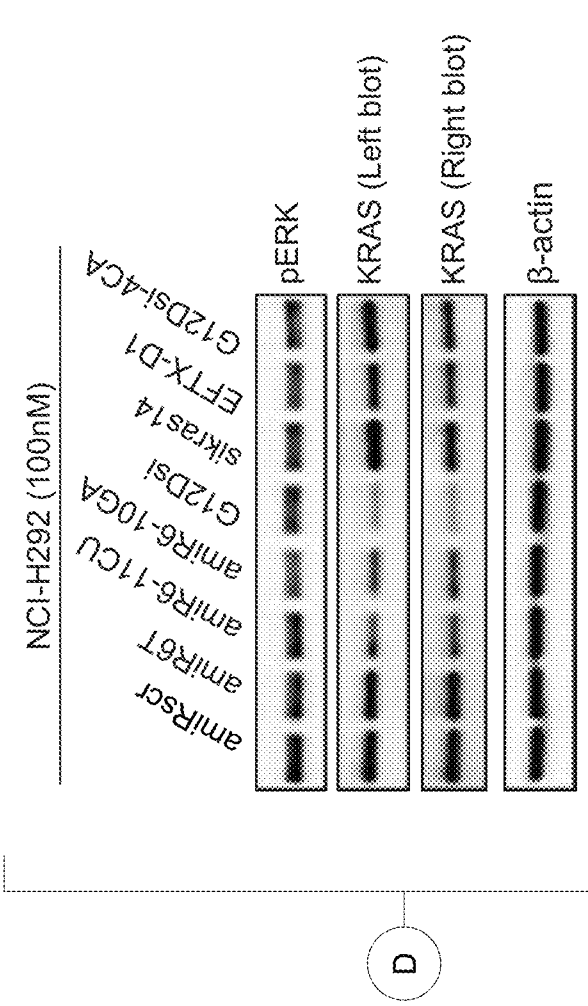
| 100nM | amiRscr | amiR6T | amiR6-11CU | amiR6-10GA | G12Dsi | sikras14 | EFTX-D1 | G12Dsi-4CA |
|---|---|---|---|---|---|---|---|---|
| pERK | 1 | 1.06 | 1.11 | 0.84 | 0.97 | 0.78 | 0.84 | 1.06 |
| KRAS (L-blot) | 1 | 1.09 | 0.49 | 0.53 | 0.25 | 1.22 | 0.75 | 1.42 |
| KRAS (R-blot) | 1 | 1.09 | 0.44 | 0.51 | 0.16 | 0.70 | 0.51 | 0.66 |
Fig. 9 (Continued...)

SEQUENCE LISTING

```
Sequence total quantity: 39
SEQ ID NO: 1            moltype = RNA  length = 22
FEATURE                 Location/Qualifiers
source                  1..22
                        mol_type = other RNA
                        organism = synthetic construct
SEQUENCE: 1
ccatcagcag gaactaccac aa                                           22

SEQ ID NO: 2            moltype = RNA  length = 24
FEATURE                 Location/Qualifiers
source                  1..24
                        mol_type = other RNA
                        organism = synthetic construct
modified_base           23..24
                        mod_base = OTHER
                        note = Thymine
SEQUENCE: 2
ccatcagcag gaactaccac aatt                                         24

SEQ ID NO: 3            moltype = RNA  length = 22
FEATURE                 Location/Qualifiers
source                  1..22
                        mol_type = other RNA
                        organism = synthetic construct
SEQUENCE: 3
acgccatctc gtccaactac ca                                           22

SEQ ID NO: 4            moltype = RNA  length = 24
FEATURE                 Location/Qualifiers
source                  1..24
                        mol_type = other RNA
                        organism = synthetic construct
modified_base           23..24
                        mod_base = OTHER
                        note = Thymine
SEQUENCE: 4
acgccatctc gtccaactac catt                                         24

SEQ ID NO: 5            moltype = RNA  length = 21
FEATURE                 Location/Qualifiers
source                  1..21
                        mol_type = other RNA
                        organism = synthetic construct
modified_base           20..21
                        mod_base = OTHER
                        note = Thymine
SEQUENCE: 5
gttggaggcg gtatgtgagt t                                            21

SEQ ID NO: 6            moltype = RNA  length = 22
FEATURE                 Location/Qualifiers
source                  1..22
                        mol_type = other RNA
                        organism = synthetic construct
modified_base           order(1,3,5,7)
                        mod_base = OTHER
                        note = 2-prime-O-methyl-substituted nucleotides
modified_base           1^2
                        mod_base = OTHER
                        note = phosphorothioate linkage
```

```
modified_base           3^4
                        mod_base = OTHER
                        note = phosphorothioate linkage
modified_base           5^6
                        mod_base = OTHER
                        note = phosphorothioate linkage
modified_base           7^8
                        mod_base = OTHER
                        note = phosphorothioate linkage
modified_base           19^20
                        mod_base = OTHER
                        note = phosphorothioate linkage
modified_base           20^21
                        mod_base = OTHER
                        note = phosphorothioate linkage
modified_base           21^22
                        mod_base = OTHER
                        note = phosphorothioate linkage
SEQUENCE: 6
ccatcagcag gaactaccac aa                                                22

SEQ ID NO: 7            moltype = RNA  length = 22
FEATURE                 Location/Qualifiers
source                  1..22
                        mol_type = other RNA
                        organism = synthetic construct
modified_base           order(1,3,5,7)
                        mod_base = OTHER
                        note = 2-prime-O-methyl-substituted nucleotides
modified_base           1^2
                        mod_base = OTHER
                        note = phosphorothioate linkage
modified_base           3^4
                        mod_base = OTHER
                        note = phosphorothioate linkage
modified_base           5^6
                        mod_base = OTHER
                        note = phosphorothioate linkage
modified_base           6^7
                        mod_base = OTHER
                        note = phosphorothioate linkage
modified_base           19^20
                        mod_base = OTHER
                        note = phosphorothioate linkage
modified_base           20^21
                        mod_base = OTHER
                        note = phosphorothioate linkage
modified_base           21^22
                        mod_base = OTHER
                        note = phosphorothioate linkage
SEQUENCE: 7
acgccatctc gtccaactac ca                                                22

SEQ ID NO: 8            moltype = RNA  length = 24
FEATURE                 Location/Qualifiers
source                  1..24
                        mol_type = other RNA
                        organism = synthetic construct
modified_base           1^2
                        mod_base = OTHER
                        note = phosphorothioate linkage
modified_base           2^3
                        mod_base = OTHER
                        note = phosphorothioate linkage
modified_base           22^23
                        mod_base = OTHER
                        note = phosphorothioate linkage
modified_base           23^24
                        mod_base = OTHER
                        note = phosphorothioate linkage
modified_base           23..24
                        mod_base = OTHER
                        note = Thymine
SEQUENCE: 8
acgccatcag ttccaactac catt                                              24

SEQ ID NO: 9            moltype = RNA  length = 24
FEATURE                 Location/Qualifiers
source                  1..24
```

```
                          mol_type = other RNA
                          organism = synthetic construct
modified_base             1^2
                          mod_base = OTHER
                          note = phosphorothioate linkage
modified_base             2^3
                          mod_base = OTHER
                          note = phosphorothioate linkage
modified_base             22^23
                          mod_base = OTHER
                          note = phosphorothioate linkage
modified_base             23^24
                          mod_base = OTHER
                          note = phosphorothioate linkage
modified_base             23..24
                          mod_base = OTHER
                          note = Thymine
SEQUENCE: 9
acgccatcaa ctccaactac catt                                             24

SEQ ID NO: 10             moltype = RNA  length = 19
FEATURE                   Location/Qualifiers
source                    1..19
                          mol_type = other RNA
                          organism = synthetic construct
ncRNA                     1..19
                          ncRNA_class = siRNA
SEQUENCE: 10
ttgcctacgt cataagctc                                                   19

SEQ ID NO: 11             moltype = RNA  length = 21
FEATURE                   Location/Qualifiers
source                    1..21
                          mol_type = other RNA
                          organism = synthetic construct
modified_base             20..21
                          mod_base = OTHER
                          note = Thymine
modified_base             1^2
                          mod_base = OTHER
                          note = phosphorothioate linkage
modified_base             2^3
                          mod_base = OTHER
                          note = phosphorothioate linkage
modified_base             19^20
                          mod_base = OTHER
                          note = phosphorothioate linkage
modified_base             20^21
                          mod_base = OTHER
                          note = phosphorothioate linkage
ncRNA                     1..21
                          ncRNA_class = siRNA
SEQUENCE: 11
ttgcctacgc catcagctct t                                                21

SEQ ID NO: 12             moltype = RNA  length = 21
FEATURE                   Location/Qualifiers
source                    1..21
                          mol_type = other RNA
                          organism = synthetic construct
modified_base             20..21
                          mod_base = OTHER
                          note = Thymine
modified_base             1^2
                          mod_base = OTHER
                          note = phosphorothioate linkage
modified_base             2^3
                          mod_base = OTHER
                          note = phosphorothioate linkage
modified_base             19^20
                          mod_base = OTHER
                          note = phosphorothioate linkage
modified_base             20^21
                          mod_base = OTHER
                          note = phosphorothioate linkage
ncRNA                     1..21
                          ncRNA_class = siRNA
SEQUENCE: 12
ttgactacgc catcagctct t                                                21
```

```
SEQ ID NO: 13          moltype = RNA  length = 21
FEATURE                Location/Qualifiers
source                 1..21
                       mol_type = other RNA
                       organism = synthetic construct
modified_base          1^2
                       mod_base = OTHER
                       note = phosphorothioate linkage
modified_base          2^3
                       mod_base = OTHER
                       note = phosphorothioate linkage
modified_base          19^20
                       mod_base = OTHER
                       note = phosphorothioate linkage
modified_base          20^21
                       mod_base = OTHER
                       note = phosphorothioate linkage
modified_base          20..21
                       mod_base = OTHER
                       note = Thymine
ncRNA                  1..21
                       ncRNA_class = siRNA
SEQUENCE: 13
ctcttgccta cgccatcagt t                                                    21

SEQ ID NO: 14          moltype = RNA  length = 22
FEATURE                Location/Qualifiers
source                 1..22
                       mol_type = other RNA
                       organism = synthetic construct
SEQUENCE: 14
cgccactacg accaactacc ac                                                   22

SEQ ID NO: 15          moltype = RNA  length = 22
FEATURE                Location/Qualifiers
source                 1..22
                       mol_type = other RNA
                       organism = synthetic construct
SEQUENCE: 15
cgccactagc tccaactacc ac                                                   22

SEQ ID NO: 16          moltype = RNA  length = 22
FEATURE                Location/Qualifiers
source                 1..22
                       mol_type = other RNA
                       organism = synthetic construct
SEQUENCE: 16
cgccactagc cccaactacc ac                                                   22

SEQ ID NO: 17          moltype = RNA  length = 22
FEATURE                Location/Qualifiers
source                 1..22
                       mol_type = other RNA
                       organism = synthetic construct
SEQUENCE: 17
cgccactagc ttcaactacc ac                                                   22

SEQ ID NO: 18          moltype = RNA  length = 19
FEATURE                Location/Qualifiers
source                 1..19
                       mol_type = other RNA
                       organism = synthetic construct
ncRNA                  1..19
                       ncRNA_class = siRNA
SEQUENCE: 18
ttgcctacgc cacaagctc                                                       19

SEQ ID NO: 19          moltype = RNA  length = 19
FEATURE                Location/Qualifiers
source                 1..19
                       mol_type = other RNA
                       organism = synthetic construct
ncRNA                  1..19
                       ncRNA_class = siRNA
SEQUENCE: 19
ttgactacgc cacaagctc                                                       19

SEQ ID NO: 20          moltype = RNA  length = 19
```

-continued

```
FEATURE              Location/Qualifiers
source               1..19
                     mol_type = other RNA
                     organism = synthetic construct
SEQUENCE: 20
ttctccgaac gtgtcacgt                                              19

SEQ ID NO: 21        moltype = RNA  length = 19
FEATURE              Location/Qualifiers
source               1..19
                     mol_type = other RNA
                     organism = synthetic construct
SEQUENCE: 21
gtctcttgga tattctcga                                              19

SEQ ID NO: 22        moltype = RNA  length = 22
FEATURE              Location/Qualifiers
source               1..22
                     mol_type = other RNA
                     organism = synthetic construct
SEQUENCE: 22
ttgtggtagt tcctgctgat gg                                          22

SEQ ID NO: 23        moltype = RNA  length = 24
FEATURE              Location/Qualifiers
source               1..24
                     mol_type = other RNA
                     organism = synthetic construct
modified_base        23..24
                     mod_base = OTHER
                     note = Thymine
SEQUENCE: 23
ttgtggtagt tcctgctgat ggtt                                        24

SEQ ID NO: 24        moltype = RNA  length = 22
FEATURE              Location/Qualifiers
source               1..22
                     mol_type = other RNA
                     organism = synthetic construct
SEQUENCE: 24
tggtagttgg acgagatggc gt                                          22

SEQ ID NO: 25        moltype = RNA  length = 24
FEATURE              Location/Qualifiers
source               1..24
                     mol_type = other RNA
                     organism = synthetic construct
modified_base        23..24
                     mod_base = OTHER
                     note = Thymine
SEQUENCE: 25
tggtagttgg acgagatggc gttt                                        24

SEQ ID NO: 26        moltype = RNA  length = 21
FEATURE              Location/Qualifiers
source               1..21
                     mol_type = other RNA
                     organism = synthetic construct
modified_base        20..21
                     mod_base = OTHER
                     note = Thymine
SEQUENCE: 26
ctcacatacc gcctccaact t                                           21

SEQ ID NO: 27        moltype = RNA  length = 24
FEATURE              Location/Qualifiers
source               1..24
                     mol_type = other RNA
                     organism = synthetic construct
modified_base        1^2
                     mod_base = OTHER
                     note = phosphorothioate linkage
modified_base        2^3
                     mod_base = OTHER
                     note = phosphorothioate linkage
modified_base        22^23
                     mod_base = OTHER
                     note = phosphorothioate linkage
modified_base        23^24
```

```
                         mod_base = OTHER
                         note = phosphorothioate linkage
modified_base            23..24
                         mod_base = OTHER
                         note = Thymine
SEQUENCE: 27
tggtagttgg aactgatggc gttt                                               24

SEQ ID NO: 28            moltype = RNA  length = 24
FEATURE                  Location/Qualifiers
source                   1..24
                         mol_type = other RNA
                         organism = synthetic construct
modified_base            1^2
                         mod_base = OTHER
                         note = phosphorothioate linkage
modified_base            2^3
                         mod_base = OTHER
                         note = phosphorothioate linkage
modified_base            22^23
                         mod_base = OTHER
                         note = phosphorothioate linkage
modified_base            23^24
                         mod_base = OTHER
                         note = phosphorothioate linkage
modified_base            23..24
                         mod_base = OTHER
                         note = Thymine
SEQUENCE: 28
tggtagttgg agttgatggc gttt                                               24

SEQ ID NO: 29            moltype = RNA  length = 19
FEATURE                  Location/Qualifiers
source                   1..19
                         mol_type = other RNA
                         organism = synthetic construct
ncRNA                    1..19
                         ncRNA_class = siRNA
SEQUENCE: 29
gagcttatga cgtaggcaa                                                     19

SEQ ID NO: 30            moltype = RNA  length = 21
FEATURE                  Location/Qualifiers
source                   1..21
                         mol_type = other RNA
                         organism = synthetic construct
modified_base            1^2
                         mod_base = OTHER
                         note = phosphorothioate linkage
modified_base            2^3
                         mod_base = OTHER
                         note = phosphorothioate linkage
modified_base            19^20
                         mod_base = OTHER
                         note = phosphorothioate linkage
modified_base            20^21
                         mod_base = OTHER
                         note = phosphorothioate linkage
modified_base            20..21
                         mod_base = OTHER
                         note = Thymine
ncRNA                    1..21
                         ncRNA_class = siRNA
SEQUENCE: 30
gagctgatgg cgtaggcaat t                                                  21

SEQ ID NO: 31            moltype = RNA  length = 21
FEATURE                  Location/Qualifiers
source                   1..21
                         mol_type = other RNA
                         organism = synthetic construct
modified_base            1^2
                         mod_base = OTHER
                         note = phosphorothioate linkage
modified_base            2^3
                         mod_base = OTHER
                         note = phosphorothioate linkage
modified_base            19^20
                         mod_base = OTHER
```

```
                        note = phosphorothioate linkage
modified_base           20^21
                        mod_base = OTHER
                        note = phosphorothioate linkage
ncRNA                   1..21
                        ncRNA_class = siRNA
modified_base           20..21
                        mod_base = OTHER
                        note = Thymine
SEQUENCE: 31
gagctgatgg cgtagtcaat t                                                    21

SEQ ID NO: 32           moltype = RNA  length = 21
FEATURE                 Location/Qualifiers
source                  1..21
                        mol_type = other RNA
                        organism = synthetic construct
modified_base           1^2
                        mod_base = OTHER
                        note = phosphorothioate linkage
modified_base           2^3
                        mod_base = OTHER
                        note = phosphorothioate linkage
modified_base           19^20
                        mod_base = OTHER
                        note = phosphorothioate linkage
modified_base           20^21
                        mod_base = OTHER
                        note = phosphorothioate linkage
modified_base           20..21
                        mod_base = OTHER
                        note = Thymine
ncRNA                   1..21
                        ncRNA_class = siRNA
SEQUENCE: 32
ctgatggcgt aggcaagagt t                                                    21

SEQ ID NO: 33           moltype = RNA  length = 19
FEATURE                 Location/Qualifiers
source                  1..19
                        mol_type = other RNA
                        organism = synthetic construct
SEQUENCE: 33
ttctccgaac gtgtcacgt                                                       19

SEQ ID NO: 34           moltype = RNA  length = 19
FEATURE                 Location/Qualifiers
source                  1..19
                        mol_type = other RNA
                        organism = synthetic construct
SEQUENCE: 34
acgtgacacg ttcggagaa                                                       19

SEQ ID NO: 35           moltype = RNA  length = 19
FEATURE                 Location/Qualifiers
source                  1..19
                        mol_type = other RNA
                        organism = synthetic construct
SEQUENCE: 35
tcgagaatat ccaagagac                                                       19

SEQ ID NO: 36           moltype = RNA  length = 24
FEATURE                 Location/Qualifiers
source                  1..24
                        mol_type = other RNA
                        organism = synthetic construct
modified_base           23..24
                        mod_base = OTHER
                        note = dT overhangs
modified_base           1^2
                        mod_base = OTHER
                        note = phosphorothioate linkage
modified_base           2^3
                        mod_base = OTHER
                        note = phosphorothioate linkage
modified_base           22^23
                        mod_base = OTHER
                        note = phosphorothioate linkage
modified_base           23^24
```

-continued

```
                         mod_base = OTHER
                         note = phosphorothioate linkage
SEQUENCE: 36
acgccatcaa ctccaactac catt                                              24

SEQ ID NO: 37            moltype = RNA  length = 24
FEATURE                  Location/Qualifiers
source                   1..24
                         mol_type = other RNA
                         organism = synthetic construct
modified_base            23..24
                         mod_base = OTHER
                         note = dT overhangs
modified_base            1^2
                         mod_base = OTHER
                         note = phosphorothioate linkage
modified_base            2^3
                         mod_base = OTHER
                         note = phosphorothioate linkage
modified_base            22^23
                         mod_base = OTHER
                         note = phosphorothioate linkage
modified_base            23^24
                         mod_base = OTHER
                         note = phosphorothioate linkage
SEQUENCE: 37
tggtagttgg agttgatggc gttt                                              24

SEQ ID NO: 38            moltype = RNA  length = 21
FEATURE                  Location/Qualifiers
source                   1..21
                         mol_type = other RNA
                         organism = synthetic construct
modified_base            20..21
                         mod_base = OTHER
                         note = dT overhangs
modified_base            1^2
                         mod_base = OTHER
                         note = phosphorothioate linkage
modified_base            2^3
                         mod_base = OTHER
                         note = phosphorothioate linkage
modified_base            19^20
                         mod_base = OTHER
                         note = phosphorothioate linkage
modified_base            20^21
                         mod_base = OTHER
                         note = phosphorothioate linkage
SEQUENCE: 38
ttgcctacgc catcagctct t                                                 21

SEQ ID NO: 39            moltype = RNA  length = 21
FEATURE                  Location/Qualifiers
source                   1..21
                         mol_type = other RNA
                         organism = synthetic construct
modified_base            20..21
                         mod_base = OTHER
                         note = dT overhangs
modified_base            1^2
                         mod_base = OTHER
                         note = phosphorothioate linkage
modified_base            2^3
                         mod_base = OTHER
                         note = phosphorothioate linkage
modified_base            19^20
                         mod_base = OTHER
                         note = phosphorothioate linkage
modified_base            20^21
                         mod_base = OTHER
                         note = phosphorothioate linkage
SEQUENCE: 39
gagctgatgg cgtaggcaat t                                                 21
```

COMPOSITIONS AND METHODS FOR SILENCING KRAS

RELATED APPLICATION DATA

The present application claims priority to U.S. Provisional Patent Application Ser. No. 63/270,229 filed Oct. 21, 2021 which is incorporated herein by reference in its entirety.

SEQUENCE LISTING

An electronic sequence listing (060015-00022.xml; size 87.5 KB; date of creation Jan. 31, 2023) submitted herewith is incorporated by reference in its entirety.

BACKGROUND

Ras mutations are associated with ~16% of human cancers. Kras is the most frequently mutated Ras isoform, accounting for 85% of all Ras-related cancers. Kras is anchored to the cell membrane through farnesylation. It cycles between an active GTP-bound state and an inactive GDP-bound state. Kras wild type (WT) is activated through the EGFR tyrosine kinase. Meanwhile, kras mutants are constitutively activated in a subset of tumor cells. Kras mutations are present in approximately 25% of tumors, making them one of the most common genetic mutations linked to cancer. They are frequent drivers of lung, colorectal and pancreatic cancers. KRAS drives 32% of lung cancers, 40% of colorectal cancers, and 85% to 90% of pancreatic cancer cases. G12C, G12D, G12V, G12R, and G13D are some of the most common KRAS mutations, based on the specific mutations that are present. Selective targeting of kras mutations is a promising strategy for cancer therapy since it can complement the activity of EGFR tyrosine kinase inhibitors and reduce side effects due to targeting of WT kras.

RNA interference (RNAi) is a gene regulation mechanism based on either a small interfering RNA (siRNA) or a microRNA (miRNA) that functions through incorporation into an RNA-induced silencing complex (RISC). miRNA mimics or artificial miRNAs are synthetic analogues of physiological miR-miR* duplexes. Both siRNA and miRNA mimics are typically designed as oligo duplexes consisting of a guide strand and a passenger strand. Inside the cell, the passenger strand is degraded and the guide-strand is retained in the RISC and seeks out target sequences in mRNA coding sequence or 5' or 3'-UTR and down-regulates gene expression through mRNA degradation and/or translational arrest. siRNA-based gene silencing mechanism typically requires a high degree of sequence match between the guide strand and the target mRNA, with some mismatches tolerated in several positions. In contrast, an miRNA-based mechanism is highly dependent on the seed-region (nt 2-7) perfectly matching the mRNA target sequence. Strictly speaking, miRNAs are defined as naturally occurring non-coding RNA that is part of the human genome. However, it is possible to design artificial miRNAs (amiRs) with a seed region that is complementary to a target sequence in an mRNA and achieve gene silencing based on a miRNA-like mechanism. Similarly, siRNAs can be designed to target a specific region of a gene based on its sequence complementarity to the guide-strand. Depending on the overall degree of target sequence complementarily and seed-region complementarity, an amiR and an siRNA can each possess activities from both a miRNA and an siRNA mechanisms, and the overall gene silencing result reflects both types of activities. Acunzo et al (PNAS 2017, 114:E4203-E4212) designed amiRs with seed regions matching a stretch of kras coding region that contains the kras point mutation, producing 6 amiRs for each point mutation. In addition, a central bulge was introduced in the amiR sequences to produce 3-nt mismatches with the kras mRNA target to diminish siRNA-like activity. Overall, the amiRs had a seed region that perfectly matched the kras mutant target, with 3 nt mismatches in total for the mutant. Meanwhile, the amiRs contained an additional mismatch to the seed region of kras wt, resulting in 4 nt mismatches total for the wt, thus producing selectivity for the kras mutant over kras wt. However, this strategy resulted in amiRs with relatively low activities against the kras mutant target and highly variable selectivity of the amiRs for the kras mutant when tested in vitro. Another strategy for targeting kras mutants is by designing siRNA molecules against the region containing the point mutation. Strategically, it is sometimes advantageous to introduce mismatches so that the siRNA will have one fewer mismatch to the mutant compared to the wild type. Papke et al. designed an siRNA that has 2 mismatches each against G12C, G12D, and G13D, and 3 mismatches against kras wt. As a result, the final sequence EFTX-D1 showed silencing activity against all 3 mutants while supposedly greatly reducing silencing activity against the kras WT. However, when we examined this particular siRNA in cell lines, we found only relatively low gene silencing activity and generally poor kras mutant selectivity.

SUMMARY

Given the limitations of prior approaches, we have created a novel strategy for designing amiRs and siRNAs and have identified amiRs and siRNAs with improved efficacy and selectivity for kras mutants over kras wild-type, thereby reducing potential side effects in therapeutic applications. In addition, the amiRs/siRNAs were incorporated into lipid nanoparticles (LNPs) for enhanced delivery in vivo. We have identified new LNP compositions that are particularly effective in amiR and siRNA delivery.

In one aspect, artificial miRNA duplexes are described herein for targeting mutants of kras. For example, in some embodiments, an miRNA duplex sequence for targeting kras mutants includes a guide strand sequence following the rules (1) the $7^{th}$ nt matches with the mutant target sequence (mismatched against the WT sequence) and/or (2) the remainder of the amiR has one additional mismatch with the corresponding target sequence in either position 10 or position 11. In another aspect, siRNA duplexes are provided for targeting mutants of kras. In some embodiments, an siRNA duplex for targeting a mutant of kras having the properties (1) a target sequence that is from the $2^{nd}$ nt of codon 10 to the $2^{nd}$ nt of codon 16, and/or (2) whose guide strand sequence contains 0-1 nt mismatch (mismatch at position 4 with C to A substitution) with the point mutated target sequence and 1-2 nt mismatch against kras WT (position 4 and the site of the point mutation).

In addition, the amiRs/siRNAs having composition and properties described herein were incorporated into lipid nanoparticles (LNPs) for enhanced delivery in vivo. For RNAi therapeutics, delivery in vivo has been identified as a key limiting factor. Most approved siRNAs (5 from Alnylam so far) are targeted to the liver, which has inherent high uptake and can be targeted through GalNAc conjugation of the siRNA. However, for solid tumors, an LNP-based strategy is the preferred option. LNPs have been shown to be efficient delivery vehicles for siRNA (e.g., Patisiran) and mRNA (COVID-19 vaccines from BioNTech and from Moderna) in the clinic, therefore, are potentially translatable into the clinic. LNPs comprise an ionizable lipid, a neutral lipid, cholesterol, and a releasable PEG-lipid. The selection of the ionizable lipid is critical. The pKa and geometry, along with biodegradability are key considerations. Existing products have utilized DLin-MC3-DMA (Alnylam), ALC-0315 (BioNTech), and SM-102 (Moderna) as the ionizable lipids.

A novel amiR design strategy was developed by limiting the number of mismatches to 2 nt against a kras mutant and 3 nt mismatch against kras wt. In contrast, the previously published amiR strategy by Acunzo et al. had 3 and 4 nt mismatches against the kras mutant and kras wt, respectively, resulting in suboptimal activity and selectivity of the amiR. This new amiR design strategy was based on a combination of experimentation and software-based RNAi activity prediction. The new amiRs will possess both miR-like and siRNA-like activities. This is a novel strategy for designing kras-mutant-selective RNAi agents.

In addition, a novel siRNA design strategy was developed by selecting a sequence with 0-1 nt mismatch with the kras mutant target sequence and 1-2 nt mismatch with the kras wild type sequence. This strategy has resulted in novel siRNA designs that were both highly active and kras mutant selective.

The above design strategies have resulted in amiRs and siRNAs that had a combination of high gene silencing activity and high kras mutant selectivity compared favorably to previously published strategies, which contained a greater number of mismatches.

DETAILED DESCRIPTION

Figure 1A:
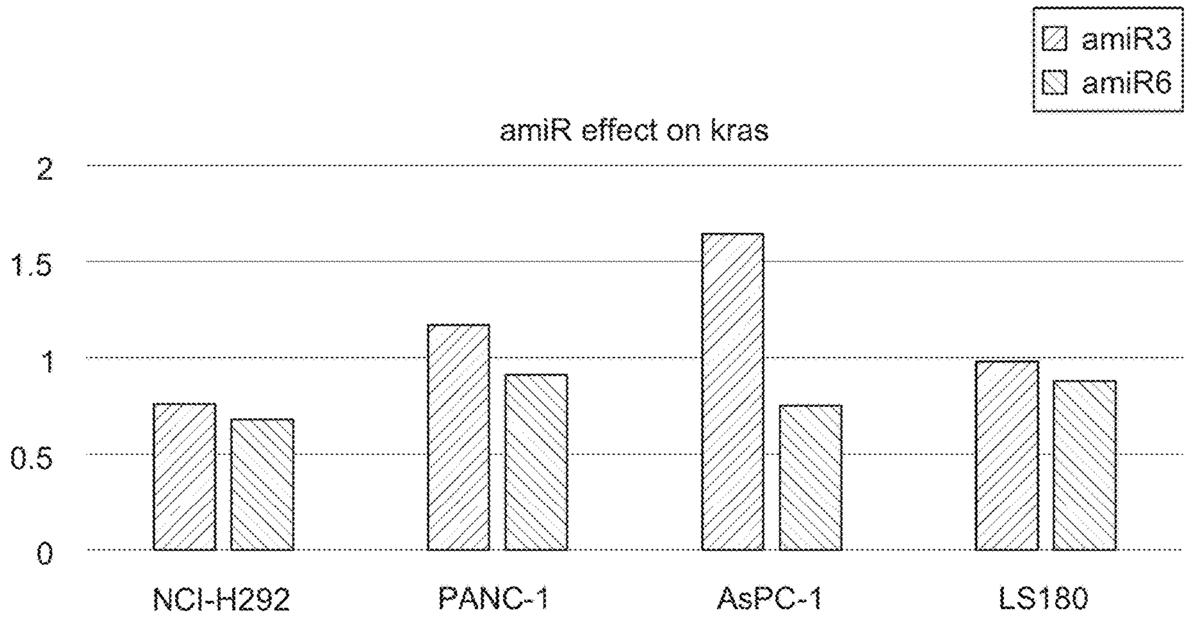
FIG. 1A: Effects of amiRs on expression levels of KRAS and pERK in Cell Lines. Cells were transfected at 50 nM of amiR3 or amiR6. Protein levels were measured by Western blot. Levels of Kras expression. All levels normalized to beta-actin as a housekeeping gene.
Figure 1B:
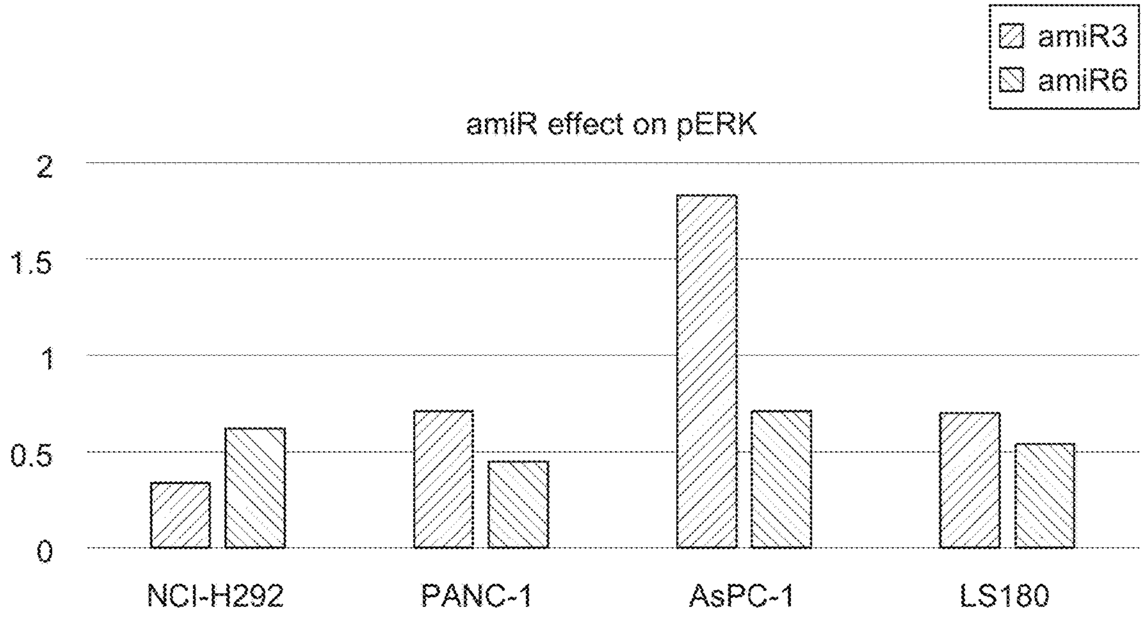
FIG. 1B: Effects of amiRs on expression levels of KRAS and pERK in Cell Lines. Cells were transfected at 50 nM of amiR3 or amiR6. Protein levels were measured by Western blot. Levels of pEKR expression. All levels normalized to beta-actin as a housekeeping gene.
Figure 2A:
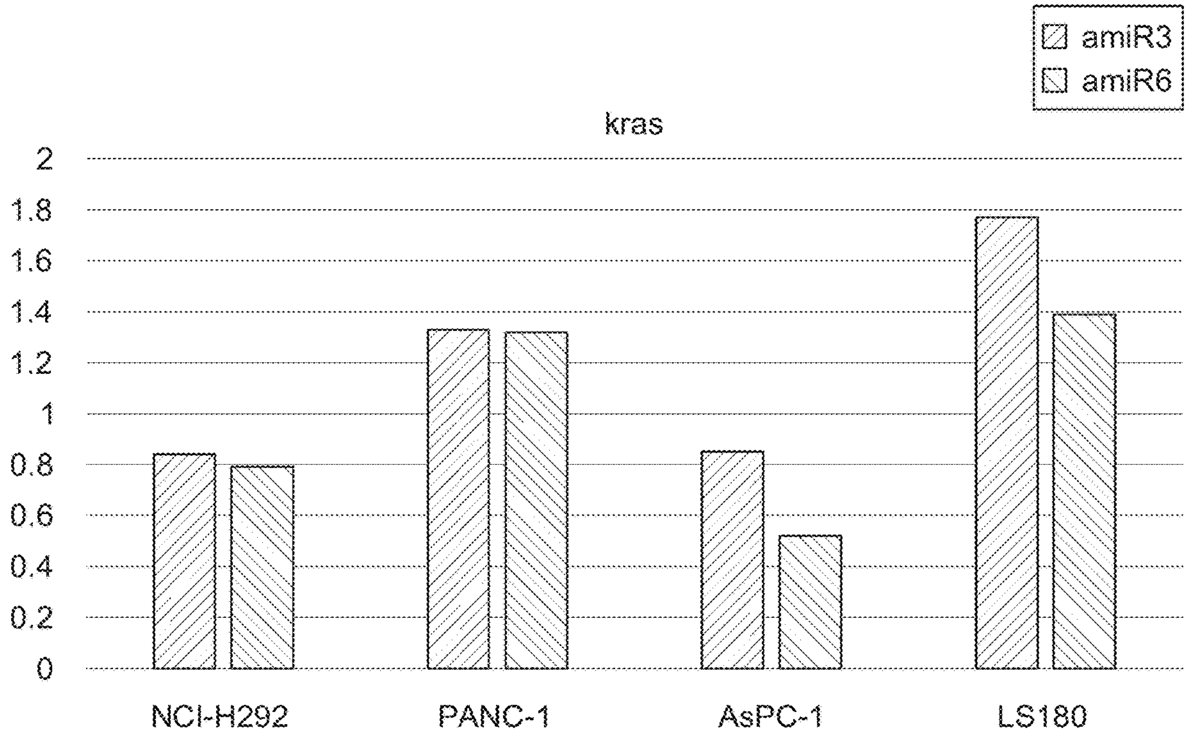
FIG. 2A: Effects of amiRs on expression levels of KRAS and pERK in Cell Lines. Cells were transfected at 100 nM of amiR3 or amiR6. Protein levels were measured by Western blot. Levels of Kras expression. All levels normalized to beta-actin as a housekeeping gene.
Figure 2B:
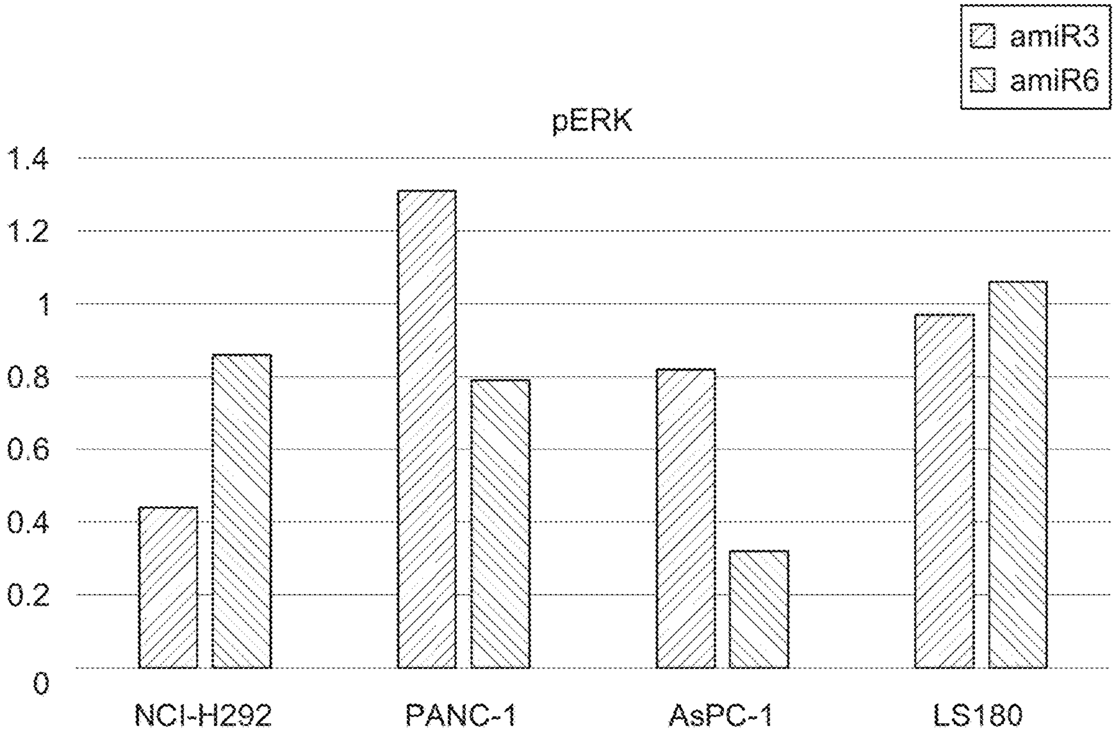
FIG. 2B: Effects of amiRs on expression levels of KRAS and pERK in Cell Lines. Cells were transfected at 100 nM of amiR3 or amiR6. Protein levels were measured by Western blot. Levels of pEKR expression. All levels normalized to beta-actin as a housekeeping gene.
Figure 3A:
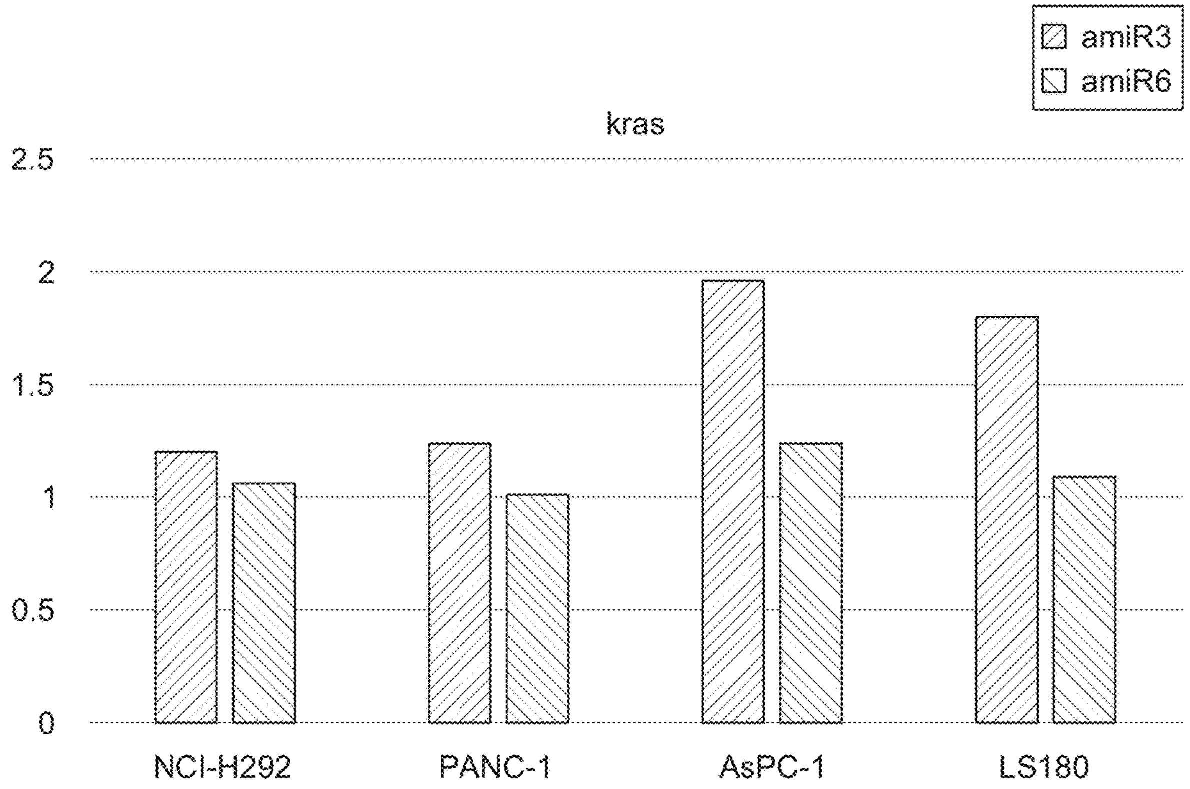
FIG. 3A: Effects of amiRs on expression levels of KRAS and pERK in Cell Lines. Cells were transfected at 200 nM of amiR3 or amiR6. Protein levels were measured by Western blot. Levels of Kras expression. All levels normalized to beta-actin as a housekeeping gene.
Figure 3B:
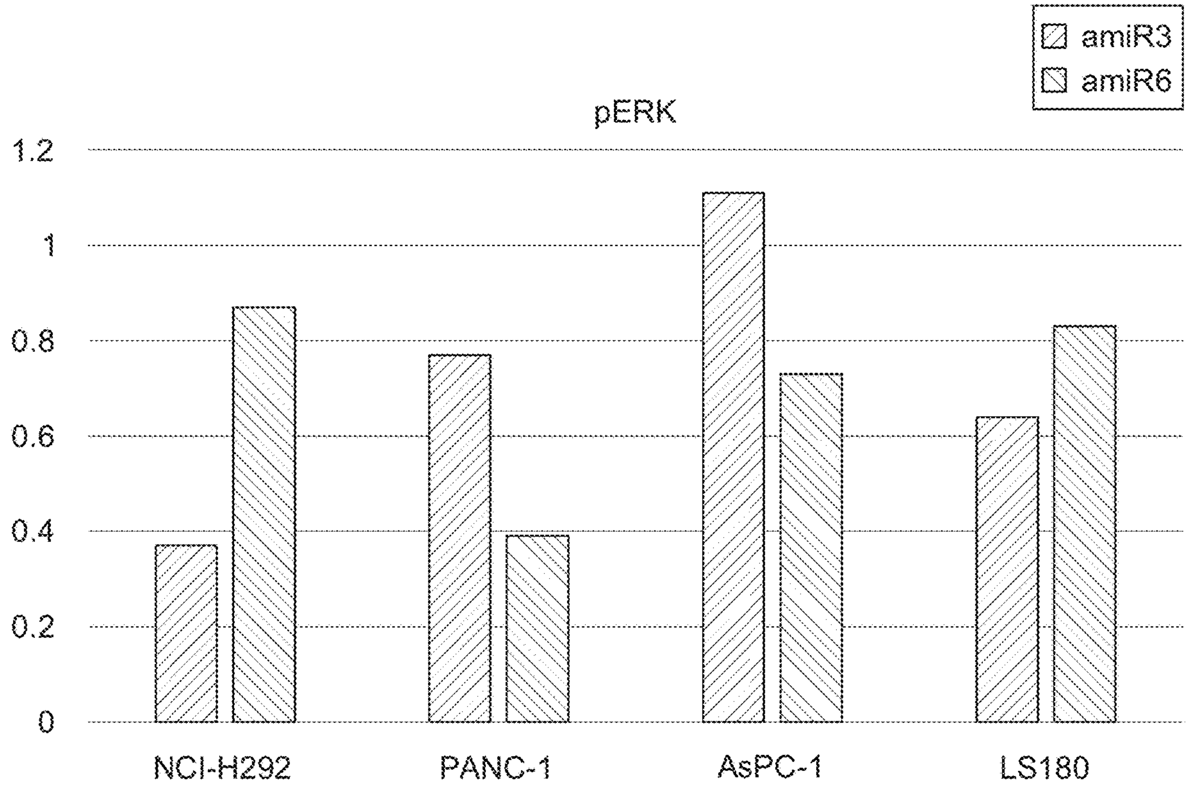
FIG. 3B: Effects of amiRs on expression levels of KRAS and pERK in Cell Lines. Cells were transfected at 200 nM of amiR3 or amiR6. Protein levels were measured by Western blot. Levels of pEKR expression. All levels normalized to beta-actin as a housekeeping gene.
Figure 4A:
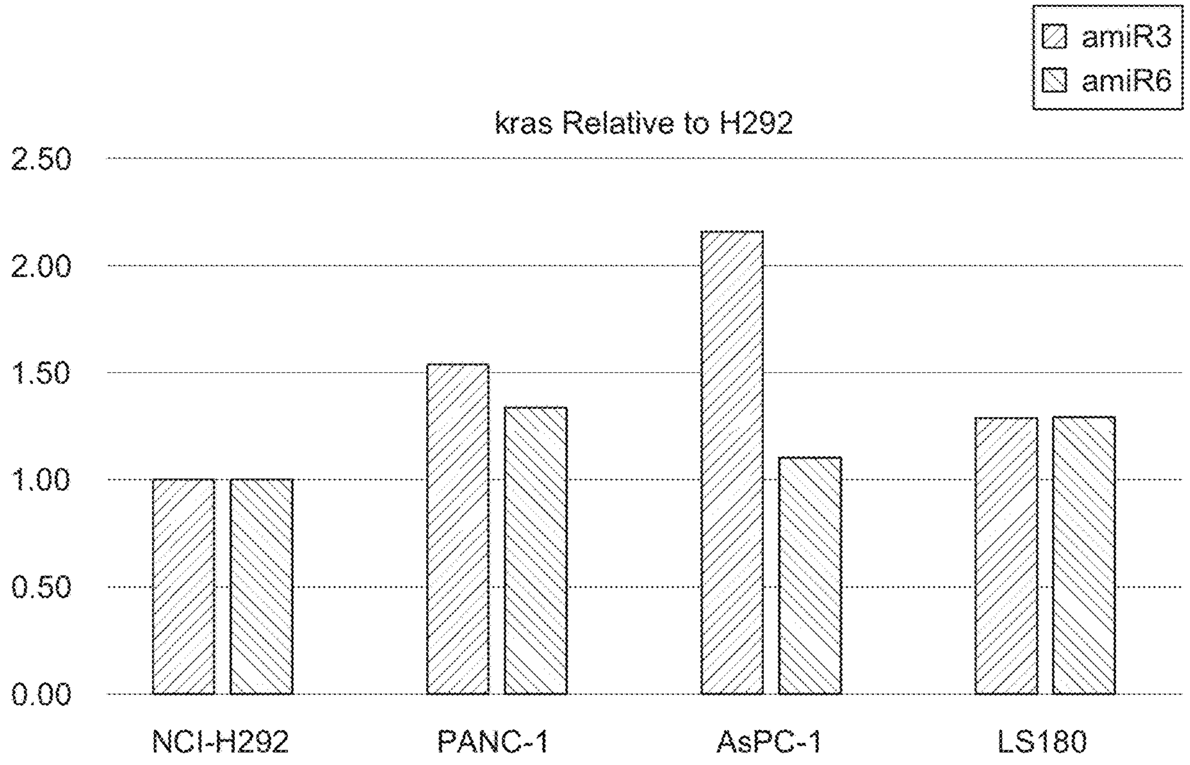
FIG. 4A: Effects of amiRs on expression levels of KRAS and pERK in Cell Lines relative to the effect on NCI-H292 cells (Kras wt). Cells were transfected at 50 nM of amiR3 or amiR6. Protein levels were measured by Western blot. Levels of Kras expression. All levels normalized to beta-actin as a housekeeping gene.
Figure 4B:
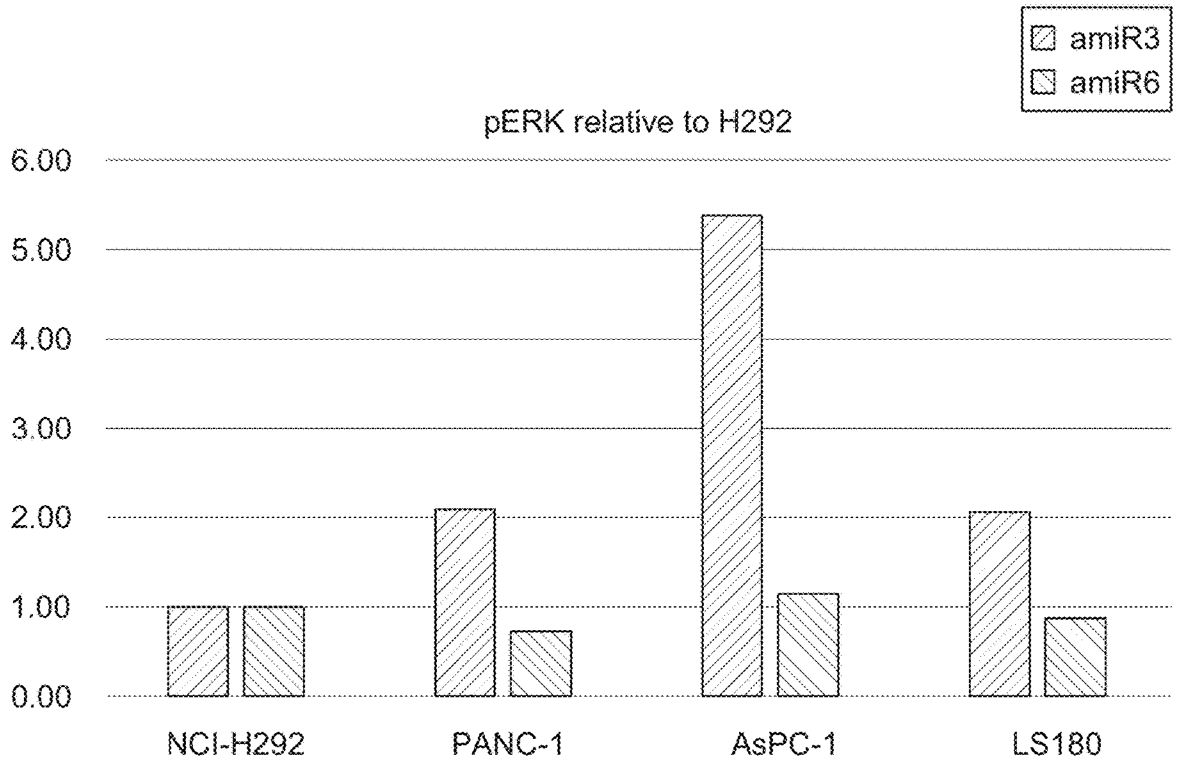
FIG. 4B: Effects of amiRs on expression levels of KRAS and pERK in Cell Lines relative to the effect on NCI-H292 cells (Kras wt). Cells were transfected at 50 nM of amiR3 or amiR6. Protein levels were measured by Western blot. Levels of pEKR expression. All levels normalized to beta-actin as a housekeeping gene.
Figure 5A:
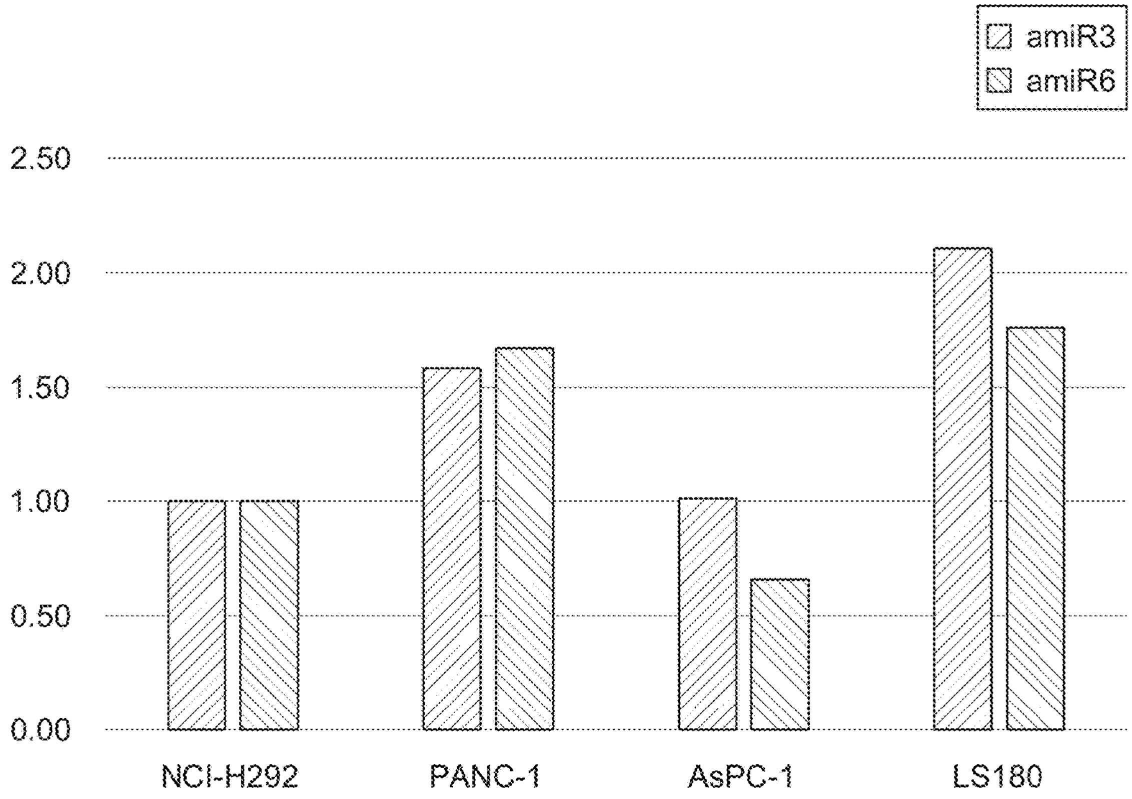
FIG. 5A: Effects of amiRs on expression levels of KRAS and pERK in Cell Lines relative to the effect on NCI-H292 cells (Kras wt). Cells were transfected at 100 nM of amiR3 or amiR6. Protein levels were measured by Western blot. Levels of Kras expression. All levels normalized to beta-actin as a housekeeping gene.
Figure 5B:
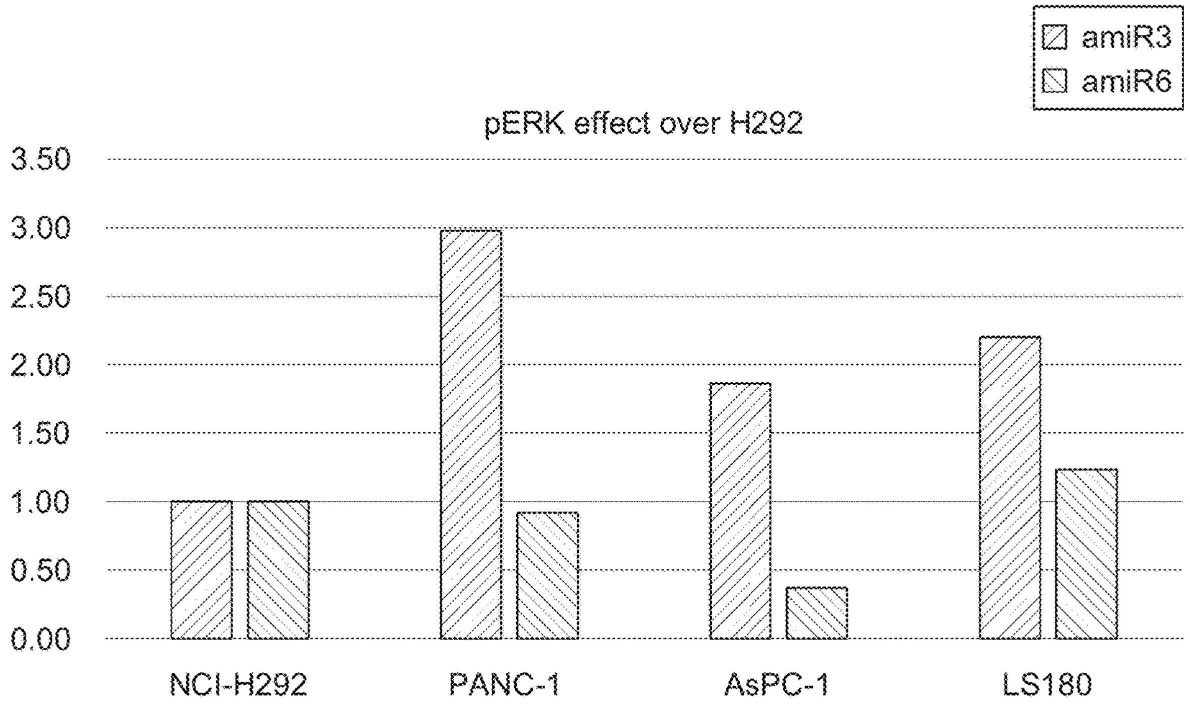
FIG. 5B: Effects of amiRs on expression levels of KRAS and pERK in Cell Lines relative to the effect on NCI-H292 cells (Kras wt). Cells were transfected at 100 nM of amiR3 or amiR6. Protein levels were measured by Western blot. Levels of pEKR expression. All levels normalized to beta-actin as a housekeeping gene.
Figure 6A:
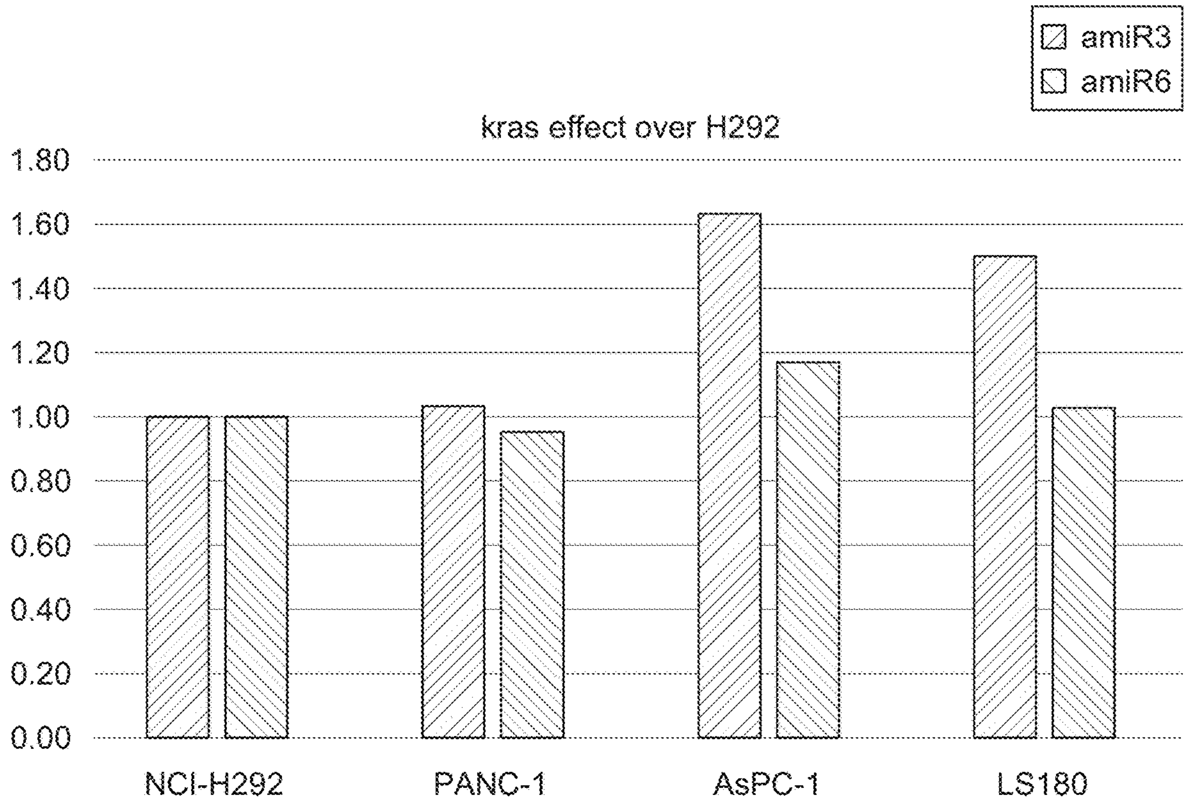
FIG. 6A: Effects of amiRs on expression levels of KRAS and pERK in Cell Lines relative to the effect on NCI-H292 cells (Kras wt). Cells were transfected at 200 nM of amiR3 or amiR6. Protein levels were measured by Western blot. Levels of Kras expression. All levels normalized to beta-actin as a housekeeping gene.
Figure 6B:
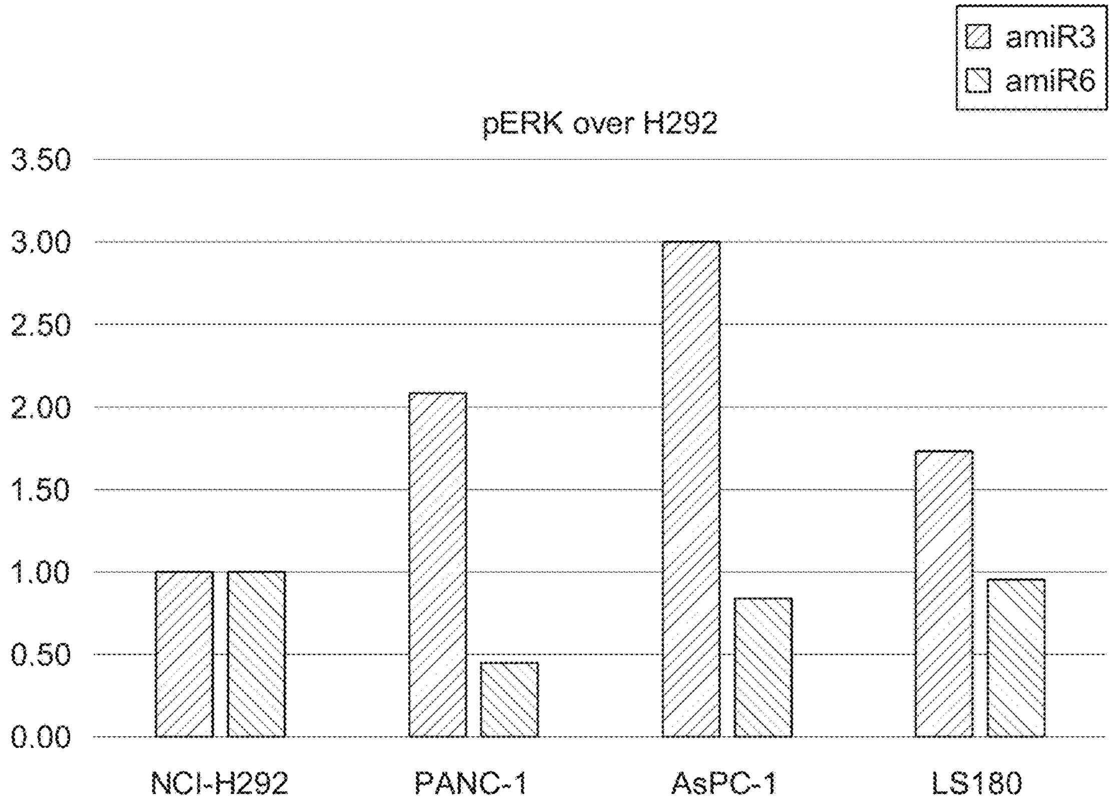
FIG. 6B: Effects of amiRs on expression levels of KRAS and pERK in Cell Lines relative to the effect on NCI-H292 cells (Kras wt). Cells were transfected at 200 nM of amiR3 or amiR6. Protein levels were measured by Western blot. Levels of pEKR expression. All levels normalized to beta-actin as a housekeeping gene.

Embodiments described herein can be understood more readily by reference to the following detailed description and examples and their previous and following descriptions. Elements, apparatus and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the spirit and scope of the invention.

The following non-limiting examples provide further disclosure of the details disclosed in the foregoing Summary.

First, data on previous amiR designs were examined. Acunzo et al (2017) disclosed an amiR design strategy. We examined the resulting amiRs targeting the G12D mutation based on the western blot data on kras (Figure S3, panel C) in his article. Despite the claim that the amiRs were kras mutant selective, the Western blot data actually showed reverse selectivity for WT, low effectiveness targeting G12D kras, or WT kras induction (see Table below for a summary of the data) among some of the amiR candidates. Induction of WT kras expression was also found. This was problematic since it could result in increased tumorigenesis. Further improvement in amiR design is clearly needed.

| | WT | G12D | Issue |
|---|---|---|---|
| KD1 | 0.92 | 1.11 | reverse selectivity |
| KD2 | 1.22 | 1.00 | low effect |
| KD3 | 1.30 | 0.78 | WT induction |
| KD4 | 1.79 | 0.70 | high WT induction |
| KD5 | 0.83 | 1.00 | reverse selectivity |
| KD6 | 1.45 | 0.78 | WT induction |

Among the amiR sequences targeting G12D in that article, KD3 and KD6 had some G12D-selective targeting effect and moderate WT induction. To investigate this observation, amiRs analogous to KD3 and KD6 were synthesized and tested in the following G12D and WT cell lines at a CRO Bioduro-Sundia. amiR3 and amiR6 were designed based on KD3 and KD6 by adopting a duplex design and adding chemical modifications to increase amiR nuclease stability.

| Cell line | Kras status | Tumor origin |
|---|---|---|
| NCI-H292 | wt | Lung cancer |
| PANC-1 | G12D/wt | Pancreatic cancer |
| Aspc-1 | G12D/G12D | Pancreatic cancer |
| LS180 | G12D/wt | Colon Cancer |

The amiR duplexes tested are as follows, and were purchased from Integrated DNA Technologies (IDT):

| Name | Sequence |
|---|---|
| amiR3 | rCrCrA rUrCrA rGrCrA rGrGrA rArCrU rArCrC rArCrA rA (SEQ ID NO: 1)<br>rUrUrG rUrGrG rUrArG rUrUrC rCrUrG rCrUrG rArUrG rG (SEQ ID NO: 22) |
| amiR3T | rCrCrA rUrCrA rGrCrA rGrGrA rArCrU rArCrC rArCrA rATT (SEQ ID NO: 2)<br>rUrUrG rUrGrG rUrArG rUrUrC rCrUrG rCrUrG rArUrG rGTT (SEQ ID NO: 23) |
| amiR6 | rArCrG rCrCrA rUrCrU rCrGrU rCrCrA rArCrU rArCrC rA (SEQ ID NO: 3)<br>rUrGrG rUrArG rUrUrG rGrArC rGrArG rArUrG rGrCrG rU (SEQ ID NO: 24) |
| amiR6t | rArCrG rCrCrA rUrCrU rCrGrU rCrCrA rArCrU rArCrC rATT (SEQ ID NO: 4)<br>rUrGrG rUrArG rUrUrG rGrArC rGrArG rArUrG rGrCrG rUTT (SEQ ID NO: 25) |
| amiRscr | rGrUrU rGrGrA rGrGrC rGrGrU rArUrG rUrGrA rGTT (SEQ ID NO: 5)<br>rCrUrC rArCrA rUrArC rCrGrC rCrUrC rCrArA rCTT (SEQ ID NO: 26) |
| amiR3a | mC*rCmA* rUmC*rA mG*rCrA rGrGrA rArCrU rArCrC rA*rC*rA* rA (SEQ ID NO: 6)<br>rCrCrA rUrCrA rGrCrA rGrGrA rArCrU rArCrC rArCrA rA (SEQ ID NO: 1) |
| amiR6a | mA*rCmG* rCmC*rA* mUrCrU rCrGrU rCrCrA rArCrU rA*rC*rC* rA (SEQ ID NO: 7)<br>rUrGrG rUrArG rUrUrG rGrArC rGrArG rArUrG rGrCrG rU (SEQ ID NO: 24) |

The symbol * denotes a phosphorothioate bond. In addition, amiR3a and amiR6a contained 2-OMe-modified nucleotides, indicated by "mN".

Western Blot Data from Bioduro-Sundia (CRO)

Transfection was performed using commercial transfection reagents at 50, 100, and 200 nM. Western blot was performed to examine the effects of various amiRs on kras expression and p-ERK (a downstream target of kras) expression. The antibody used recognizes both mutant and wt kras proteins. Data from all 3 concentrations are provided in FIGS. 1A, 1B, 2A, 2B, 3A, and 3B.

In addition, it was also useful to look at the effect of the amiRs on kras and pERK relative to the wt control NCI-292 cell line to assess the selectivity of the amiRs. The results are presented in FIGS. 4A, 4B, 5A, 5B, 6A, and 6B.

Conclusions of this study:

1. amiR6 generally had greater down regulatory effects on kras and pERK in the cells than amiR3
2. amiR3 exhibited reverse selectivity for G12D, whereas amiR6 had relatively good selectivity for G12D, especially in the homozygous G12D Aspc-1 cells. The effect was more pronounced in pERK relative to kras, which was expressed at relatively low levels.

Figure 7A:
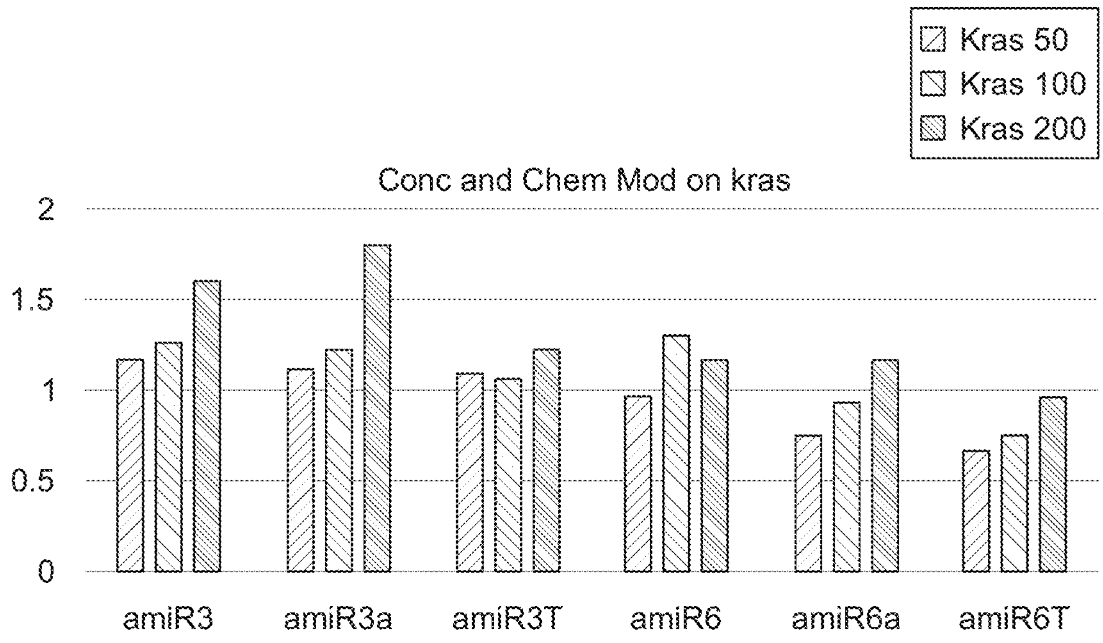
FIG. 7A: Effects of concentration and chemical modifications on target regulation. Expression of kras. All levels normalized to beta-actin as a housekeeping gene.
Figure 7B:
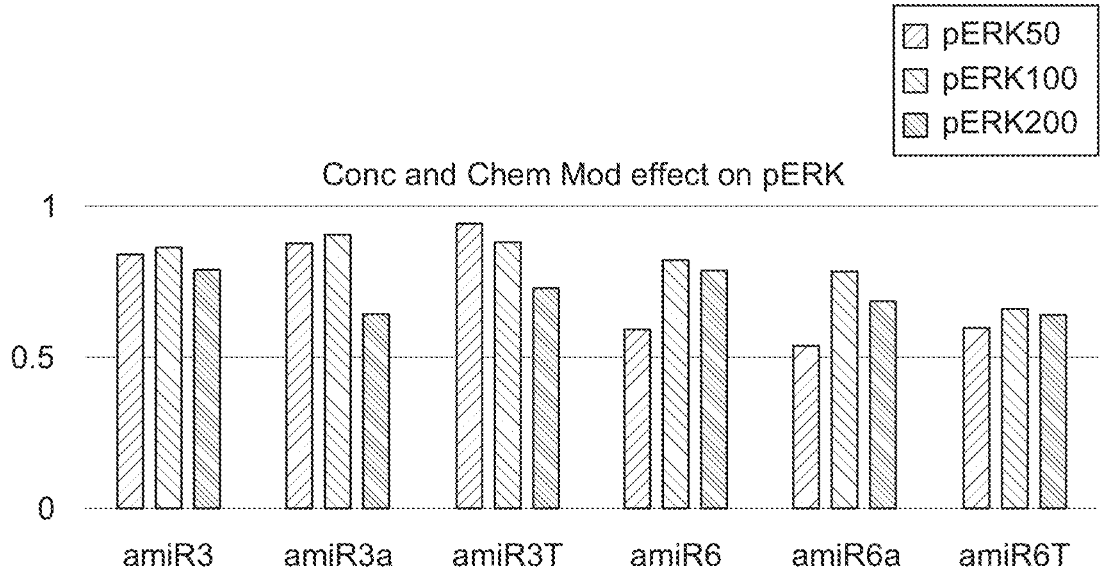
FIG. 7B: Effects of concentration and chemical modifications on target regulation. Expression of pERK. All levels normalized to beta-actin as a housekeeping gene.

Effects of amiR Concentration and Chemical modifications are illustrated in FIGS. 7A-7B.

Conclusions of this study:

1. A high amiR concentration seemed to upregulate kras in vitro, possibly due to the use of transfection agents containing cationic lipids and possible off-target activation of alternative pathways. The concentration effect of the amiRs on pERK was not clear
2. Overall the effect followed the ranking of amiRt>=amiRa>amiR for different amiR overhang designs and chemical modifications studied. So amiRt or amiRa was the preferred amiR chemistry.

To further improve target downregulation, it was then decided that the number of mismatches in the amiRs versus the kras G12D mutant sequence be reduced from 3 nt to 2 nt in the central bulge region. The newly designed amiR6 variants were evaluated by the open-source DesiRm software, which generated predicted gene silencing activity. This resulted in the identification of two amiR6 variants, amiR6-11CU and amiR6-10GA. The sequences of these amiRs are as follows:

amiR6 and variants
amiR6t (original)
Sequence 1

(SEQ ID NO: 4)
rArCrG rCrCrA rUrCrU rCrGrU rCrCrA rArCrU rArCrC rATT

Sequence 2

(SEQ ID NO: 25)
rUrGrG rUrArG rUrUrG rGrArC rGrArG rArUrG rGrCrG rUTT amiR6-11CU (variant)

(SEQ ID NO: 8)
rA*rC*rG rCrCrA rUrCrA rGrUrU rCrCrA rArCrU rArCrC rA*T*T

-continued

```
                                              (SEQ ID NO: 27)
rU*rG*rG rUrArG rUrUrG rGrArA rCrUrG rArUrG rGrCrG rU*T*T

amiR6-10GA (variant)
                                              (SEQ ID NO: 9)
rA*rC*rG rCrCrA rUrCrA rArCrU rCrCrA rArCrU rArCrC rA*T*T

                                              (SEQ ID NO: 28)
rU*rG*rG rUrArG rUrUrG rGrArG rUrUrG rArUrG rGrCrG rU*T*T
```

Kras Mutant Targeting Using siRNA

It is possible to design siRNAs that match with a kras mutant and contain a mismatch to the kras wt sequence. In this case, the seed region (nt 2-7) of the siRNA guide strand is outside the region opposite the point mutation of the kras mutant, which distinguished this strategy from the above-discussed amiR strategy. A recent article (Papke et al. ACS Pharmacol. Transl. Sci. 2021, 4, 2, 703-712) reported an siRNA, named EFTX-D1, which had 2 mismatches with G12D and 3 mismatches with kras wt target sequence. It was claimed that this siRNA could selectively target kras G12D. However, EFTX-D1 was found to be suboptimal because the number of mismatches was too numerous to sustain effective silencing of the kras target. Therefore, improved siRNAs were designed with fewer mismatches, as shown below:

G12Dsi had the greatest kras knockdown. amiR6-10GA and G12Dsi-4CA were exceptionally potent, both for pERK and kras downregulation.

Figure 11:
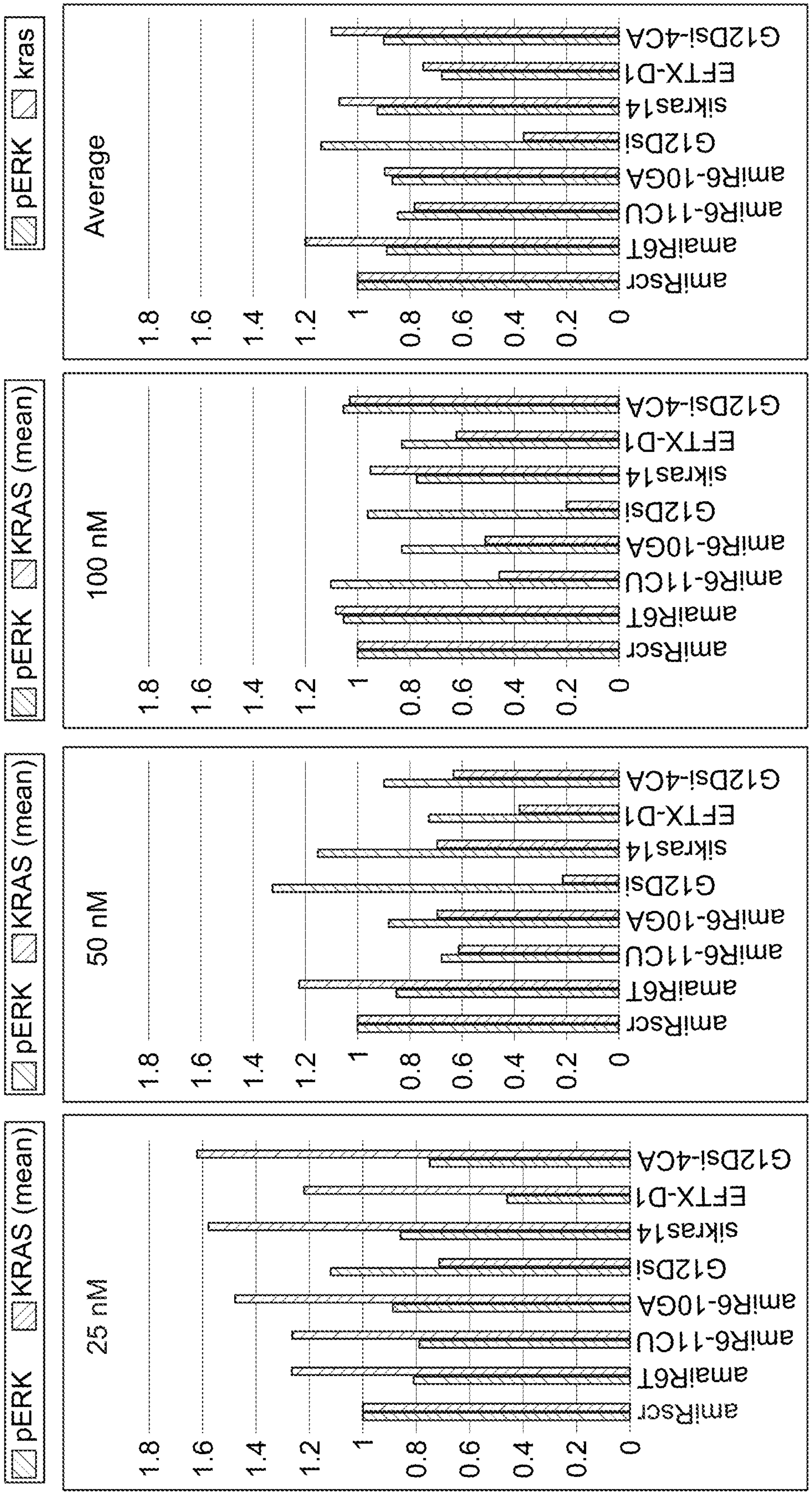
FIG. 11. Relative expression levels of pERK and Kras from Western blot results of NCI-H292 (KRAS WT) cells treated with amiRs.

In NCI H292 kras wt cells, the results are provided in FIG. 11.

G12Dsi had the greatest knockdown of kras but not pERK. amiR6-11CU, amiR10GA, and EFTX-D1 also had significant knockdown effects.

Figure 12:
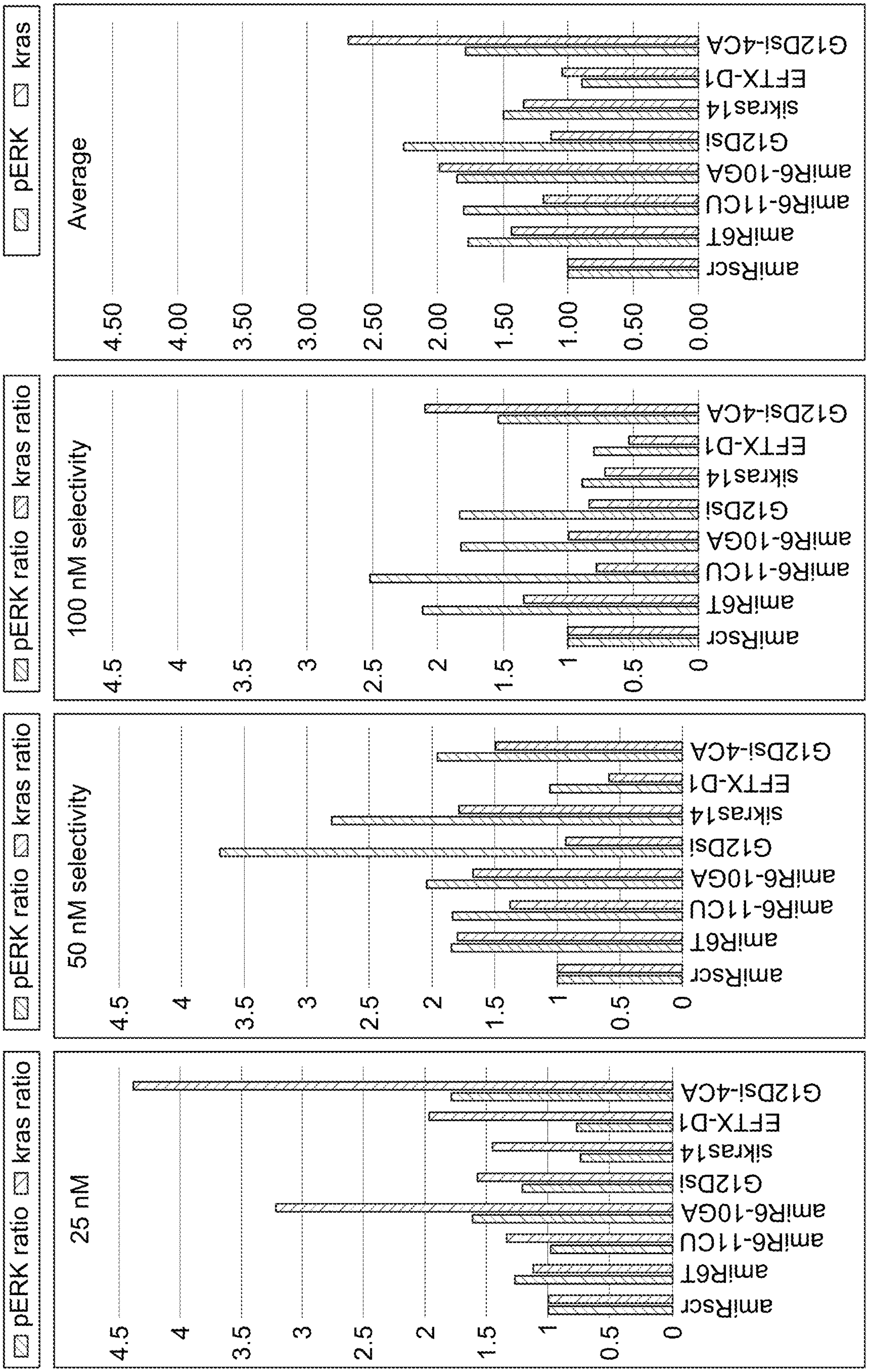
FIG. 12. Selectivity of amiRs for the G12D mutant Aspc-1 relative to the WT Aspc-1 cells in down-regulation of pERK and Kras FIG. 13. Relative expression of Kras in Aspc-1 cells following amiR treatment. mRNA levels were measured by qRT-PCR after treatment at 3 concentrations.

Selectivity for G12D over WT for the various amiR and siRNA constructs are provided in FIG. 12.

G12D selectivity seemed to be highly concentration-dependent and differed for pERK and kras At 25 nM, G12si4CA and amiR10GA had the best kras and pERK selectivity (much better than EFTX-D1)

```
SiRNAs
EFTX-D1 (this is as reported by Papke et al)
                                              (SEQ ID NO: 10)
rUrUrG rCrCrU rArCrG rUrCrA rUrArA rGrCrU rC

                                              (SEQ ID NO: 29)
rGrArG rCrUrU rArUrG rArCrG rUrArG rGrCrA rA

G12Dsi (this siRNA has a perfect match with G12D and one mismatch with kras WT)
                                              (SEQ ID NO: 11)
rU*rU*rG rCrCrU rArCrG rCrCrA rUrCrA rGrCrU rC*T*T

                                              (SEQ ID NO: 30)
rG*rA*rG rCrUrG rArUrG rGrCrG rUrArG rGrCrA rA*T*T

G12Dsi-4CA (this siRNA has 1 mismatch with G12D and 2 mismatches with kras WT)
                                              (SEQ ID NO: 12)
rU*rU*rG rArCrU rArCrG rCrCrA rUrCrA rGrCrU rC*T*T

                                              (SEQ ID NO: 31)
rG*rA*rG rCrUrG rArUrG rGrCrG rUrArG rUrCrA rA*T*T

sikras14 (this is an alternative siRNA with a different targeting sequence from EFTX-D1)
                                              (SEQ ID NO: 13)
rC*rU*rC rUrUrG rCrCrU rArCrG rCrCrA rUrCrA rG*T*T

                                              (SEQ ID NO: 32)
rC*rU*rG rArUrG rGrCrG rUrArG rGrCrA rArGrA rG*T*T
```

Figure 8:
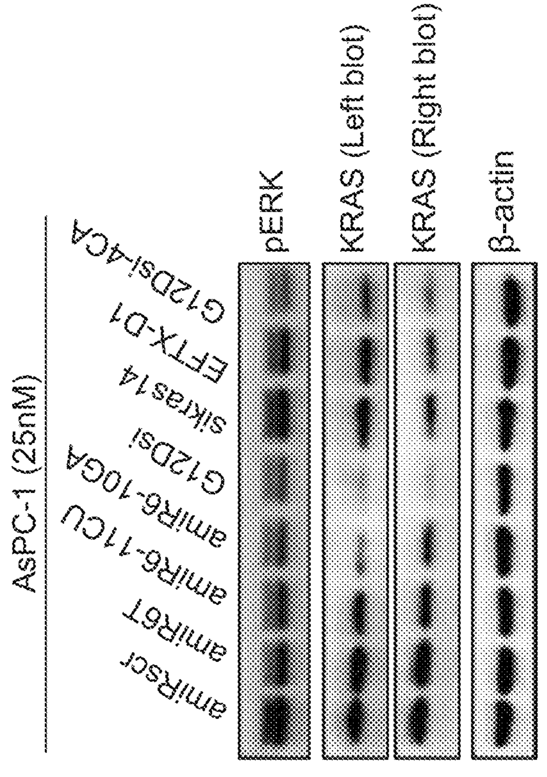
FIG. 8. Western blot results of AsPC-1 (KRAS G12D) cells treated with amiRs.
Figure 9:
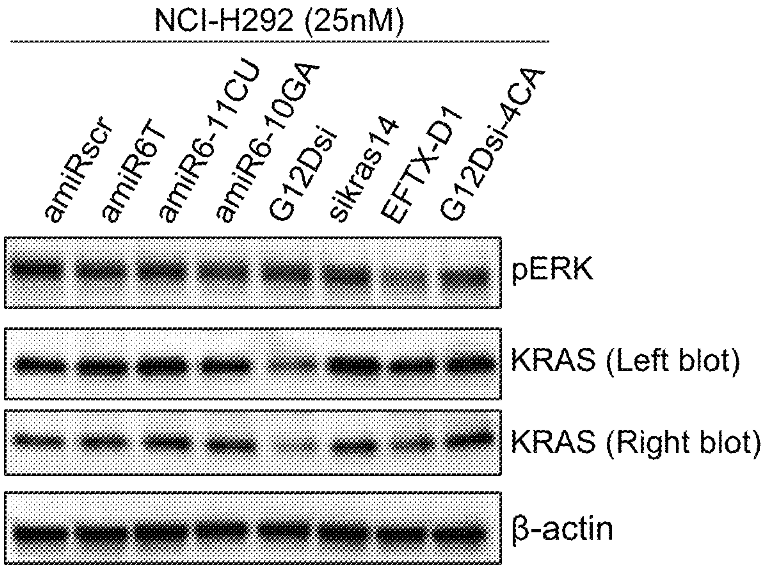
FIG. 9. Western blot results of NCI-H292 (KRAS WT) cells treated with amiRs.

The newly designed amiRs and siRNAs were evaluated in G12D homozygous AsPC-1 cells and kras WT NCI-H292 cells. Kras and pERK were analyzed by Western blot, whereas kras mRNA was measured by qRT-PCR. Selectivity for kras G12D over kras WT was calculated. The results are as follows:

3 amiR-based designs and 4 siRNA-based designs were synthesized by IDT and tested in G12D AsPC-1 and WT NCI-H292 cells. Western blot on kras and pERK and qRT-PCR on kras were carried out at 25, 50, and 100 nM concentrations at Bioduro-Sundia. The results are provided in the Western blot data of FIGS. 8-9.

Figure 10:
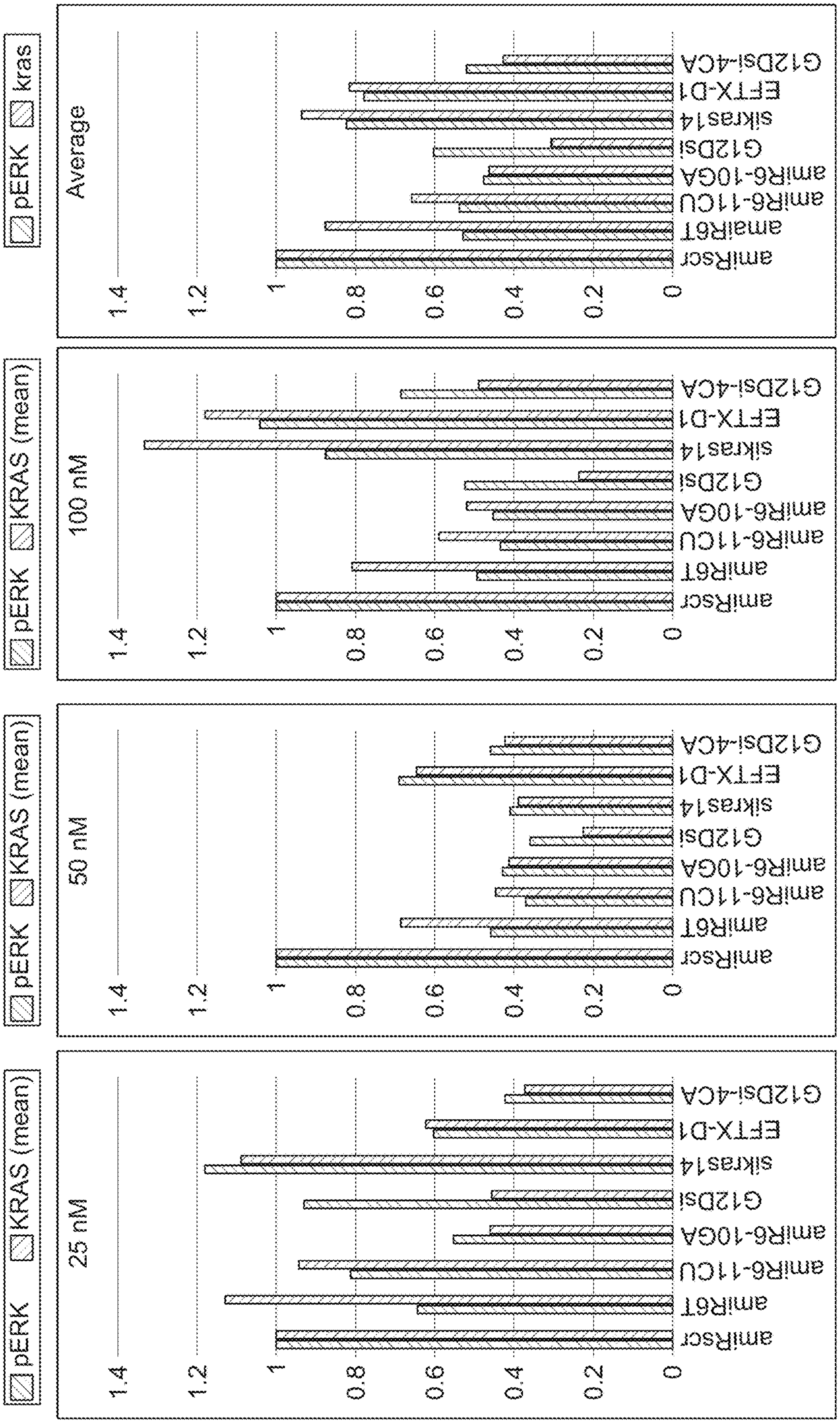
FIG. 10. Relative expression levels of pERK and Kras from Western blot results of AsPC-1 (KRAS G12D) cells treated with amiRs.

The downregulation of pERK and kras in Aspc-1 G12D cells is summarized in FIG. 10.

At 50 nM, amiR6T, amiR6-10GA, sikras14, and G12Dsi-4CA showed kras selectivity. In addition, G12Dsi showed good pERK selectivity At 100 nM G12Dsi-4CA showed good kras selectivity and some pERK selectivity. All amiRs and G12Dsi showed good pERK selectivity.

Looking at effects at all concentrations:

- amiR-6T, -11CU and -10GA exhibited preferential down-regulation of KRas and pERK proteins in the mutant (G12D) cells compared to the KRas (WT) cells. amiR-6-10GA & -11CU appear to be more effective than amiR-6T.
- G12Dsi knocked down KRas in both cell lines, but pERK was depleted only in the mutant cells.
- G12D-4CA appears to be promising in reducing both Kras and pERK levels in the mutant cells.

Overall, G12Dsi-4CA and amiR6-10GA had the best selectivity for the mutant (G12D) over WT KRas. These two artificial siRNA/miRNA are promising therapeutic candidates for KRasG12D than the previously reported EFTX-D1 (Silencing of Oncogenic KRAS by Mutant-Selective Small Interfering RNA. Papke B et al. ACS Pharmacol Transl Sci. 2021 Feb. 4; 4 (2):703-712.) in terms of efficacy and selectivity both for KRas and pERK.

Overall, G12Dsi-4CA and amiR6-10GA had the best selectivity for G12D over WT, amiR6T and G12Dsi also had significant selectivity for G12D.

Conclusion Based on the WB Data

Based on efficacy and selectivity data, amiR6-10GA and G12Dsi-4CA were deemed to warrant further evaluation as G12D selective amiR/siRNA therapeutic candidates. G12Dsi also appeared promising due to its higher kras knockdown and excellent pERK selectivity for G12D mutant cell lines. These constructs were more efficacious than the previously reported EFTX-D1 both in terms of efficacy and selectivity for kras and pERK.

Downregulation of kras mRNA by amiR/siRNA Assessed by qRT-PCR

Introduction qRT-PCR was used to directly measure the down-regulation of the kras mRNA target. It should be noted that amiR and siRNA possess both mRNA down-regulation and translational arrest.

amiR is likely to have a greater effect on translation due to its mechanism. So qRT-PCR will show a greater effect for siRNA than amiRs due to this difference.

Raw Data

Kras expression in AsPC-1 cells by qRT-PCR

| Oligos ID | 100 nM | | | 50 nM | | | 25 nM | | |
|---|---|---|---|---|---|---|---|---|---|
| amiRscr | 0.99 | 0.99 | 1.03 | 1.06 | 1.01 | 0.94 | 0.97 | 0.99 | 1.04 |
| amiR6T | 0.66 | 0.66 | 0.69 | 0.85 | 0.72 | 0.84 | 0.79 | 0.80 | 0.68 |
| amiR6-11CU | 0.57 | 0.49 | 0.56 | 0.71 | 0.63 | 0.62 | 0.51 | 0.48 | 0.50 |
| amiR6-10GA | 0.67 | 0.60 | 0.62 | 0.74 | 0.76 | 0.79 | 0.62 | 0.59 | 0.57 |
| G12Dsi | 0.26 | 0.29 | 0.31 | 0.31 | 0.32 | 0.36 | 0.39 | 0.36 | 0.34 |
| sikras14 | 1.05 | 0.92 | 0.74 | 0.70 | 0.84 | 0.72 | 0.95 | 0.93 | 0.84 |
| EFTX-D1 | 0.60 | 0.77 | 0.59 | 0.63 | 0.69 | 0.55 | 0.69 | 0.77 | 0.69 |
| G12Dsi-4CA | 0.16 | 0.18 | 0.15 | 0.15 | 0.18 | 0.19 | 0.23 | 0.27 | 0.23 |

Average RQ

| Oligos ID | 100 nM | 50 nM | 25 nM |
|---|---|---|---|
| amiRscr | 1.00 | 1.00 | 1.00 |
| amiR6T | 0.67 | 0.80 | 0.76 |
| amiR6-11CU | 0.54 | 0.65 | 0.49 |
| amiR6-10GA | 0.63 | 0.76 | 0.59 |
| G12Dsi | 0.29 | 0.33 | 0.36 |
| sikras14 | 0.90 | 0.76 | 0.91 |
| EFTX-D1 | 0.65 | 0.63 | 0.72 |
| G12Dsi-4CA | 0.16 | 0.17 | 0.24 |

Figure 13:
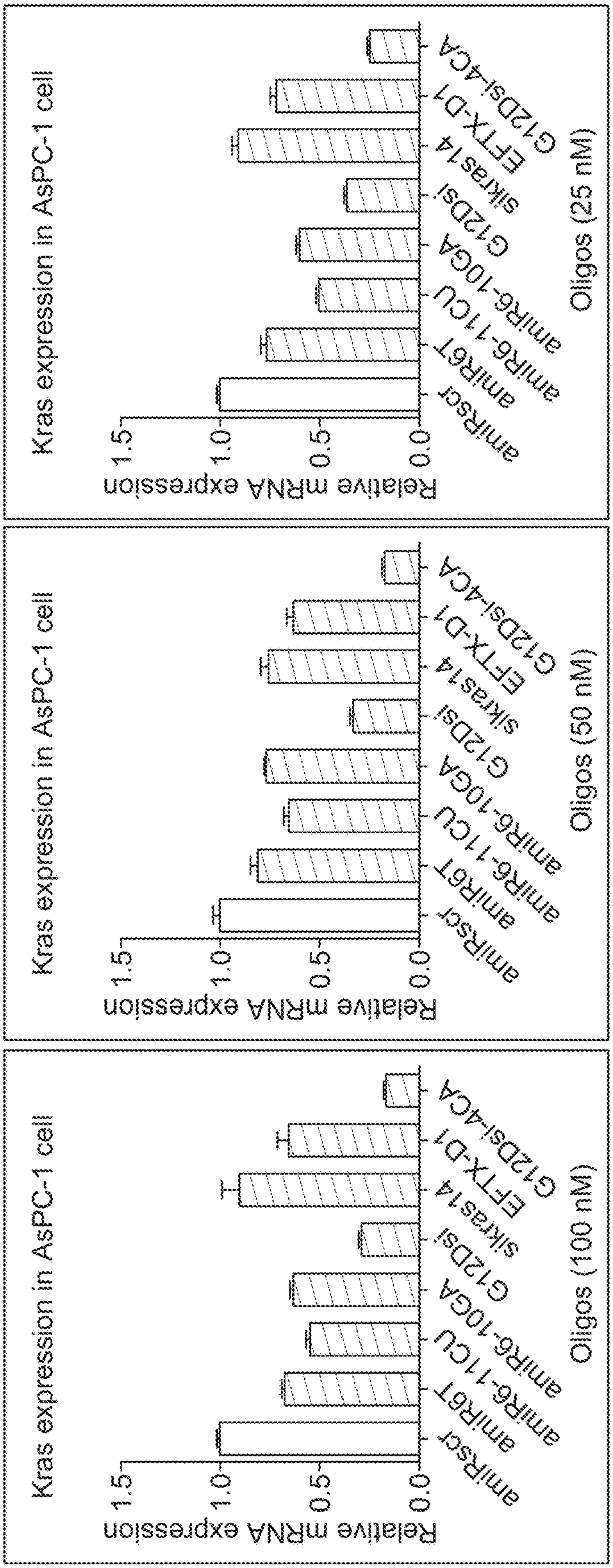

Additional data is provided in FIG. 13.

Kras expression in NCI-H292 cells by qRT-PCR RQ

| Oligos ID | 100 nM | | | 50 nM | | | 25 nM | | |
|---|---|---|---|---|---|---|---|---|---|
| amiRscr | 0.98 | 1.01 | 1.01 | 0.97 | 1.05 | 0.99 | 1.02 | 1.08 | 0.90 |
| amiR6T | 1.24 | 1.39 | 1.20 | 1.48 | 1.50 | 1.30 | 1.49 | 1.35 | 1.21 |

-continued

| Oligos ID | 100 nM | | | 50 nM | | | 25 nM | | |
|---|---|---|---|---|---|---|---|---|---|
| amiR6-11CU | 1.56 | 1.46 | 1.41 | 0.87 | 0.89 | 0.88 | 1.11 | 1.07 | 1.07 |
| amiR6-10GA | 1.17 | 1.32 | 1.19 | 1.36 | 1.37 | 1.36 | 1.02 | 1.01 | 1.01 |
| G12Dsi | 0.59 | 0.63 | 0.57 | 0.48 | 0.56 | 0.55 | 0.54 | 0.56 | 0.61 |
| sikras14 | 1.12 | 1.13 | 1.13 | 1.00 | 0.91 | 0.86 | 0.80 | 0.82 | 0.88 |
| EFTX-D1 | 0.55 | 0.56 | 0.49 | 0.49 | 0.44 | 0.40 | 0.44 | 0.42 | 0.41 |
| G12Dsi-4CA | 0.94 | 0.96 | 0.89 | 0.62 | 0.85 | 0.73 | 0.71 | 0.76 | 0.70 |

Average RQ

| Oligos ID | 100 nM | 50 nM | 25 nM |
|---|---|---|---|
| amiRscr | 1.00 | 1.00 | 1.00 |
| amiR6T | 1.28 | 1.43 | 1.35 |
| amiR6-11CU | 1.47 | 0.88 | 1.08 |
| amiR6-10GA | 1.22 | 1.36 | 1.01 |
| G12Dsi | 0.60 | 0.53 | 0.57 |
| sikras14 | 1.12 | 0.93 | 0.83 |
| EFTX-D1 | 0.54 | 0.44 | 0.42 |
| G12Dsi-4CA | 0.93 | 0.73 | 0.72 |

Figure 14:
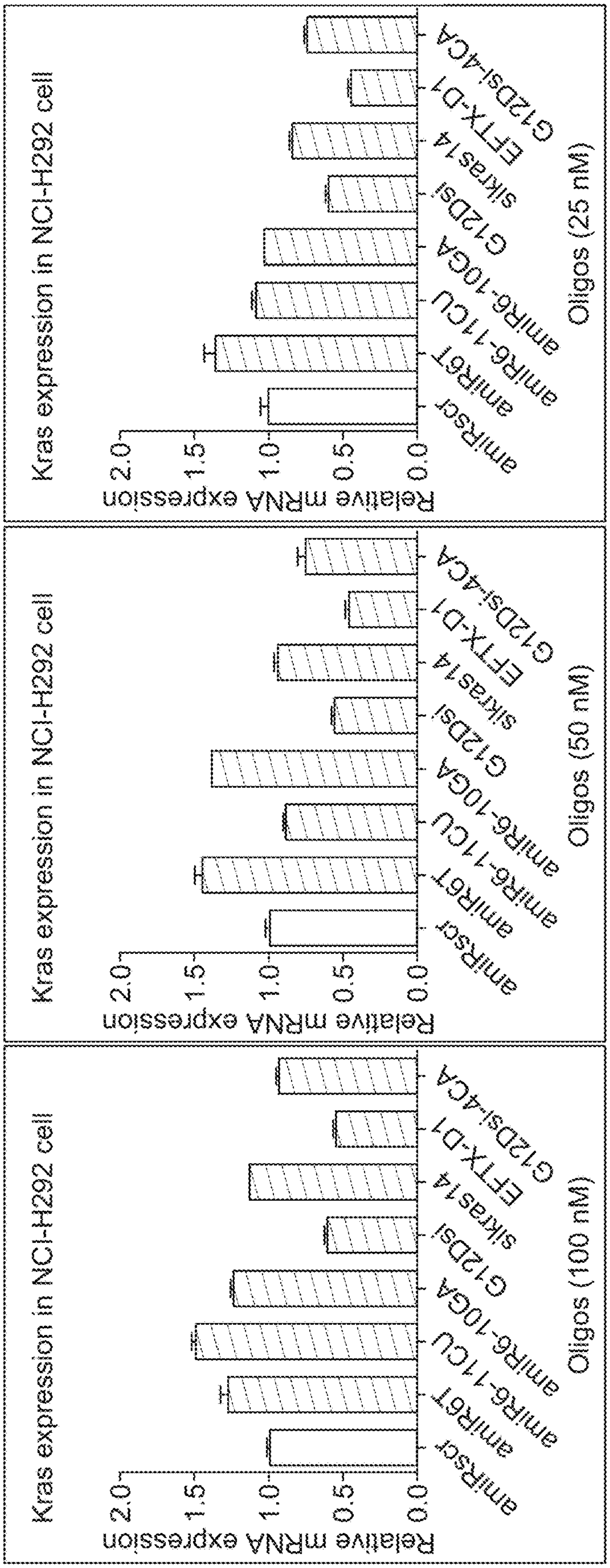
FIG. 14. Relative expression of Kras in NCI-H292 cells following amiR treatment. mRNA levels were measured by qRT-PCR after treatment at 3 concentrations.

Additional data is provided in FIG. 14.

Figure 15:
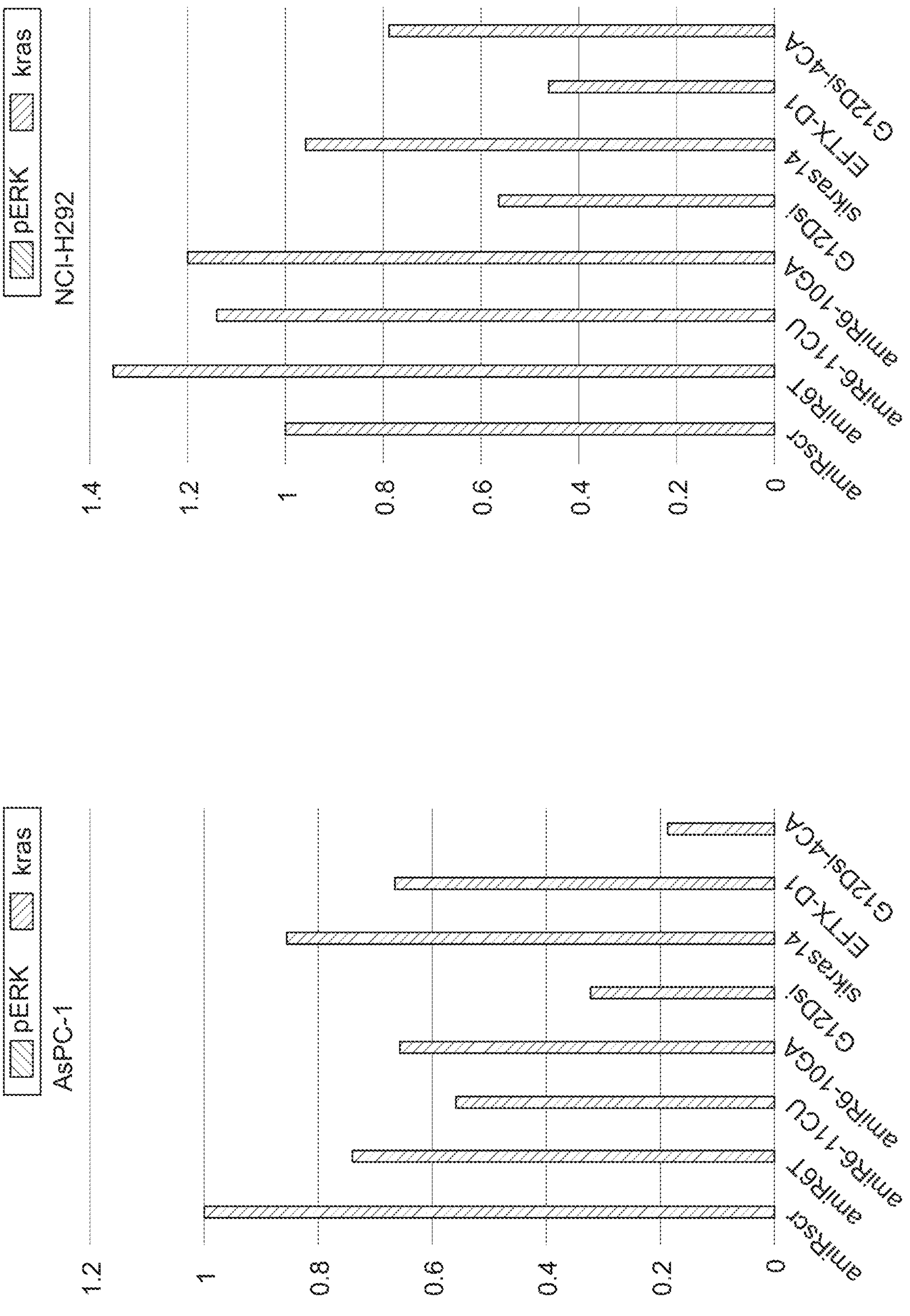
FIG. 15. Relative expression of Kras in Aspc-1 and NCI-H292 cells following amiR treatment averaging data from 3 concentrations. mRNA levels were measured by qRT-PCR.
Figure 16:
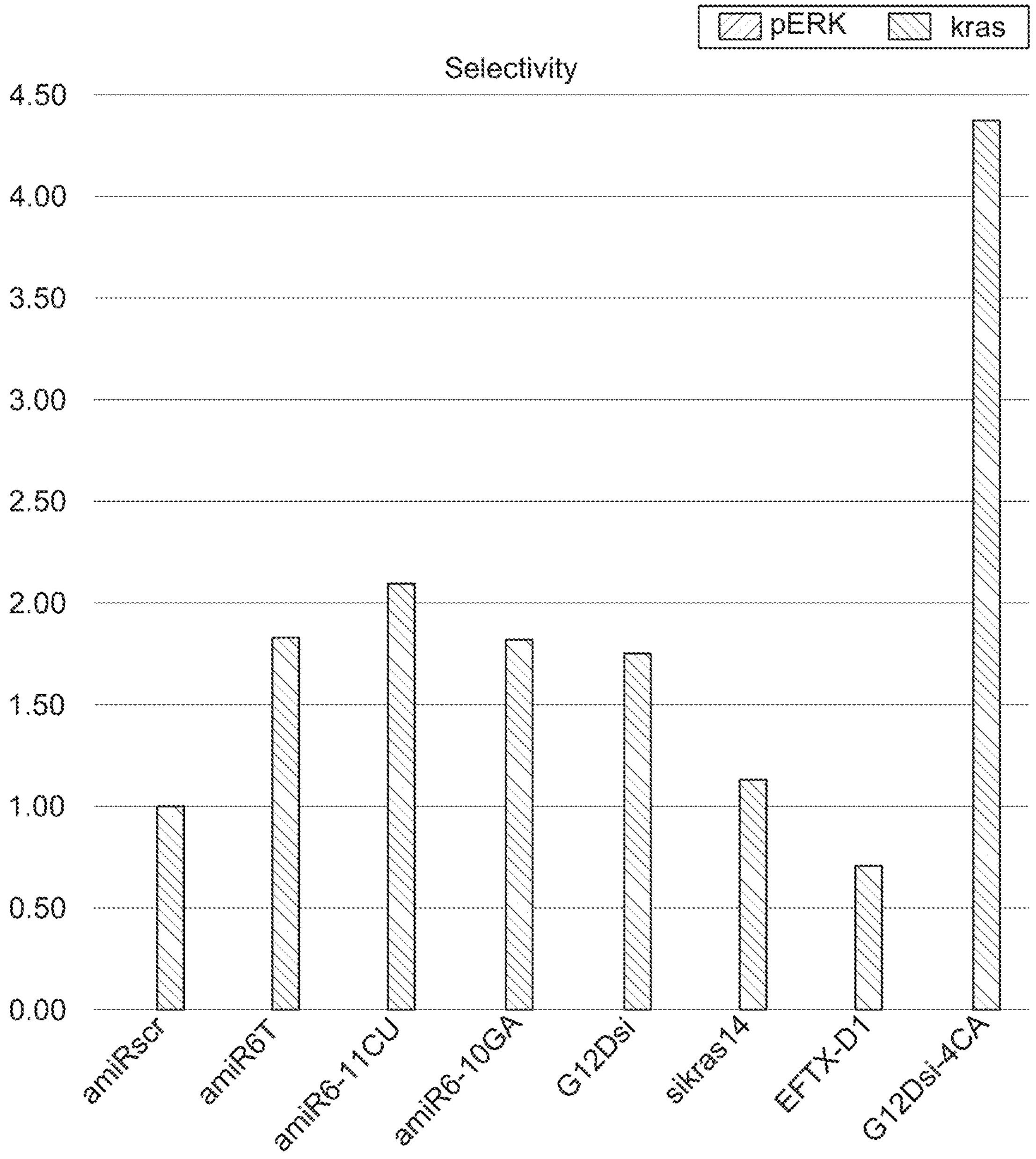
FIG. 16. Selectivity of amiRs for the G12D mutant Aspc-1 relative to the WT Aspc-1 cells in down-regulation of Kras Mrna.
Figure 17A:
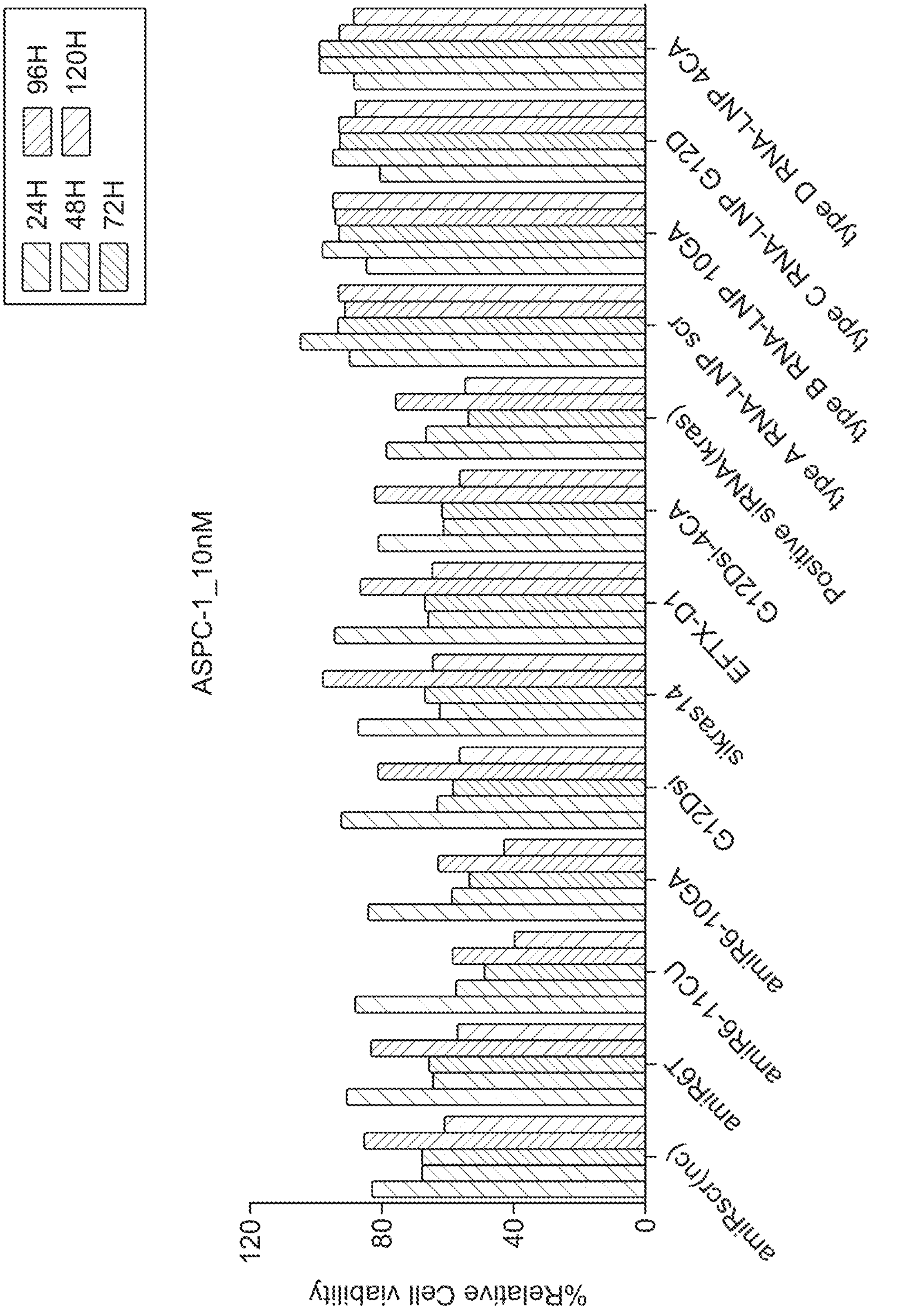
FIG. 17A: Inhibition of Aspc-1 cell growth by amiRs. Relative cell viability was determined following treatment with a transfection agent or with amiR or siRNA loaded in LNPs. 10 nM.
Figure 17B:
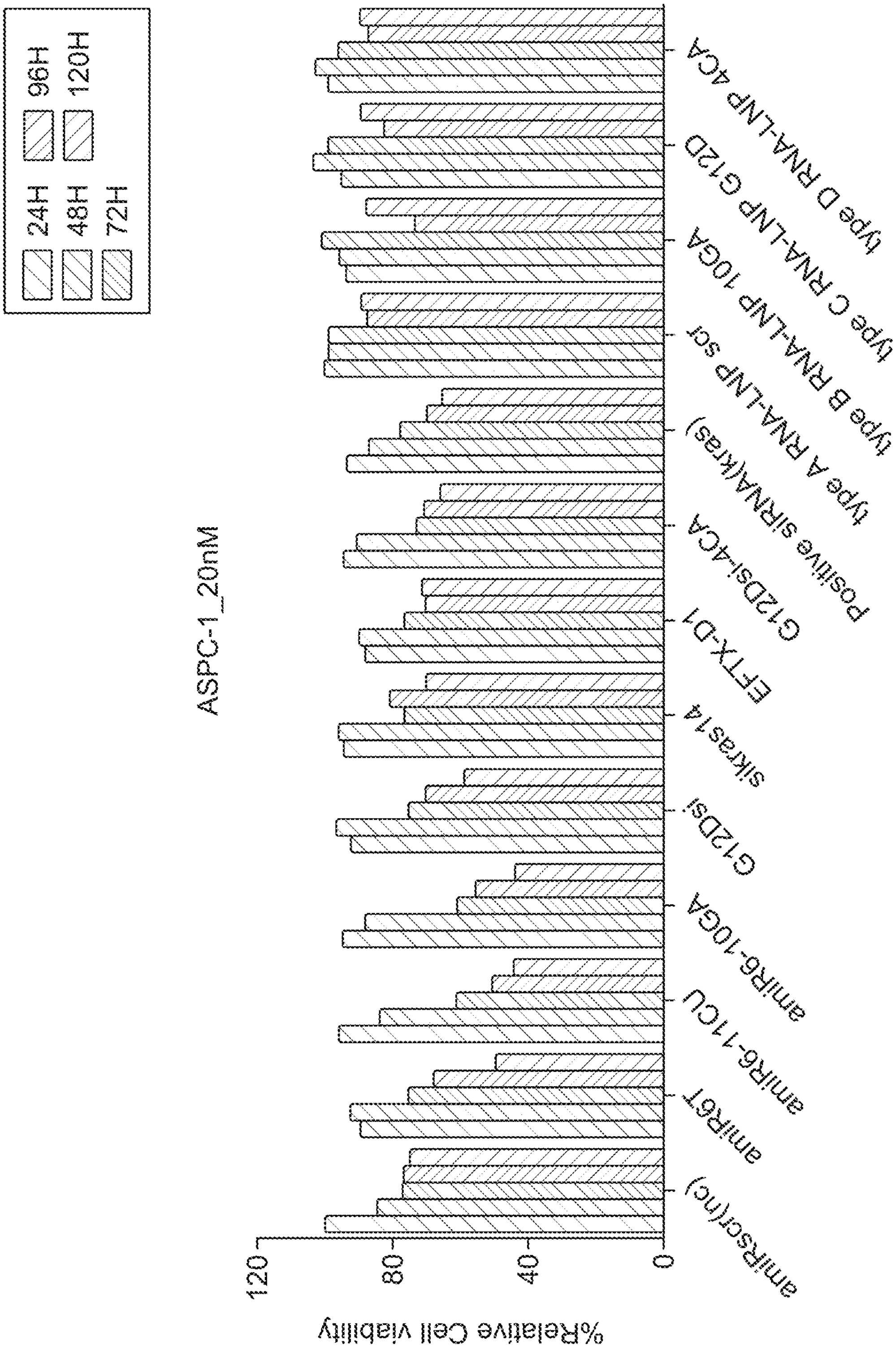
FIG. 17B: Inhibition of Aspc-1 cell growth by amiRs. Relative cell viability was determined following treatment with a transfection agent or with amiR or siRNA loaded in LNPs. 20 Nm.
Figure 18A:
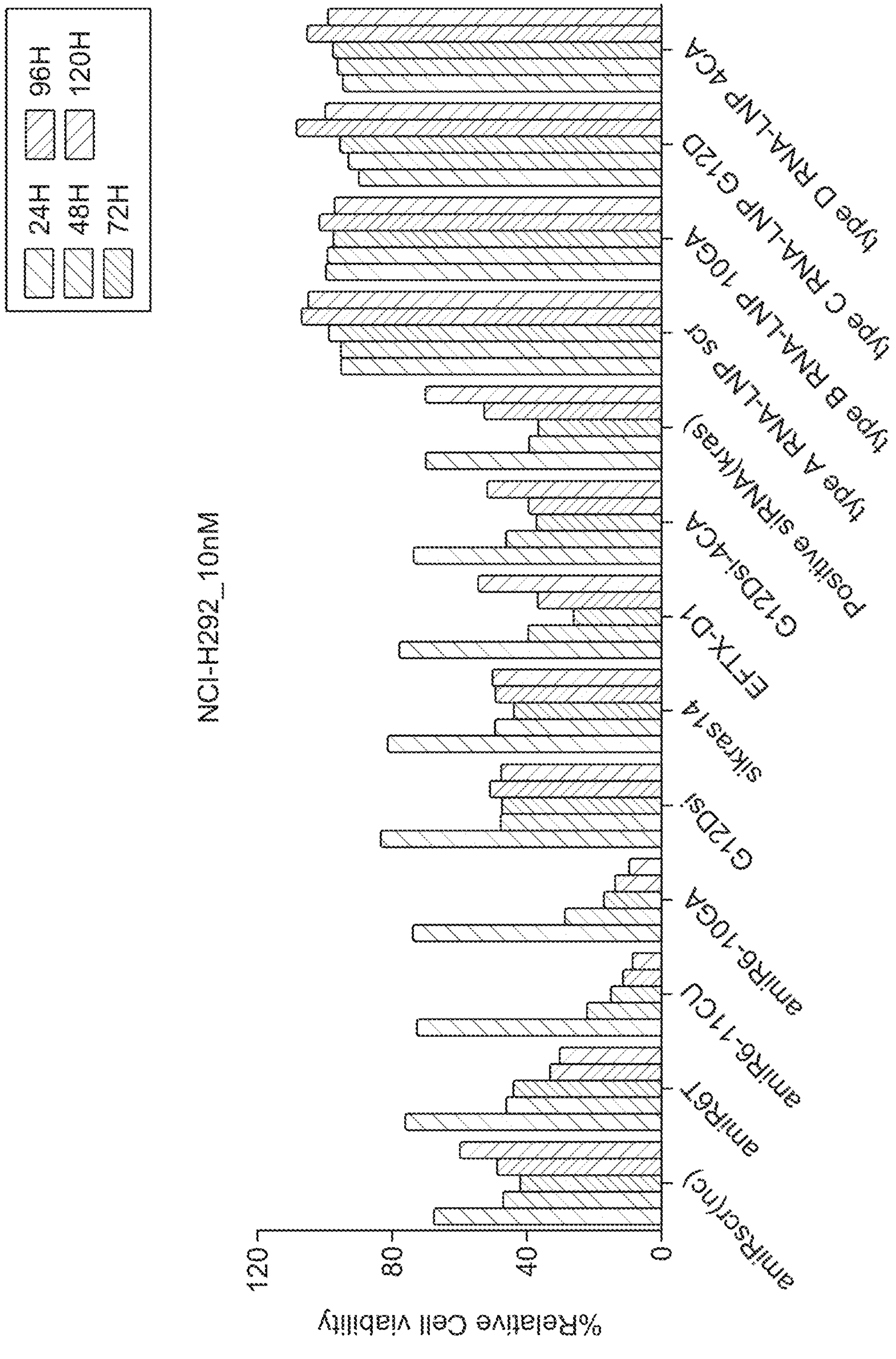
FIG. 18A: Inhibition of NCI-H292 cell growth by amiRs. Relative cell viability was determined following treatment with a transfection agent or with amiR or siRNA loaded in LNPs. 10 nM.
Figure 18B:
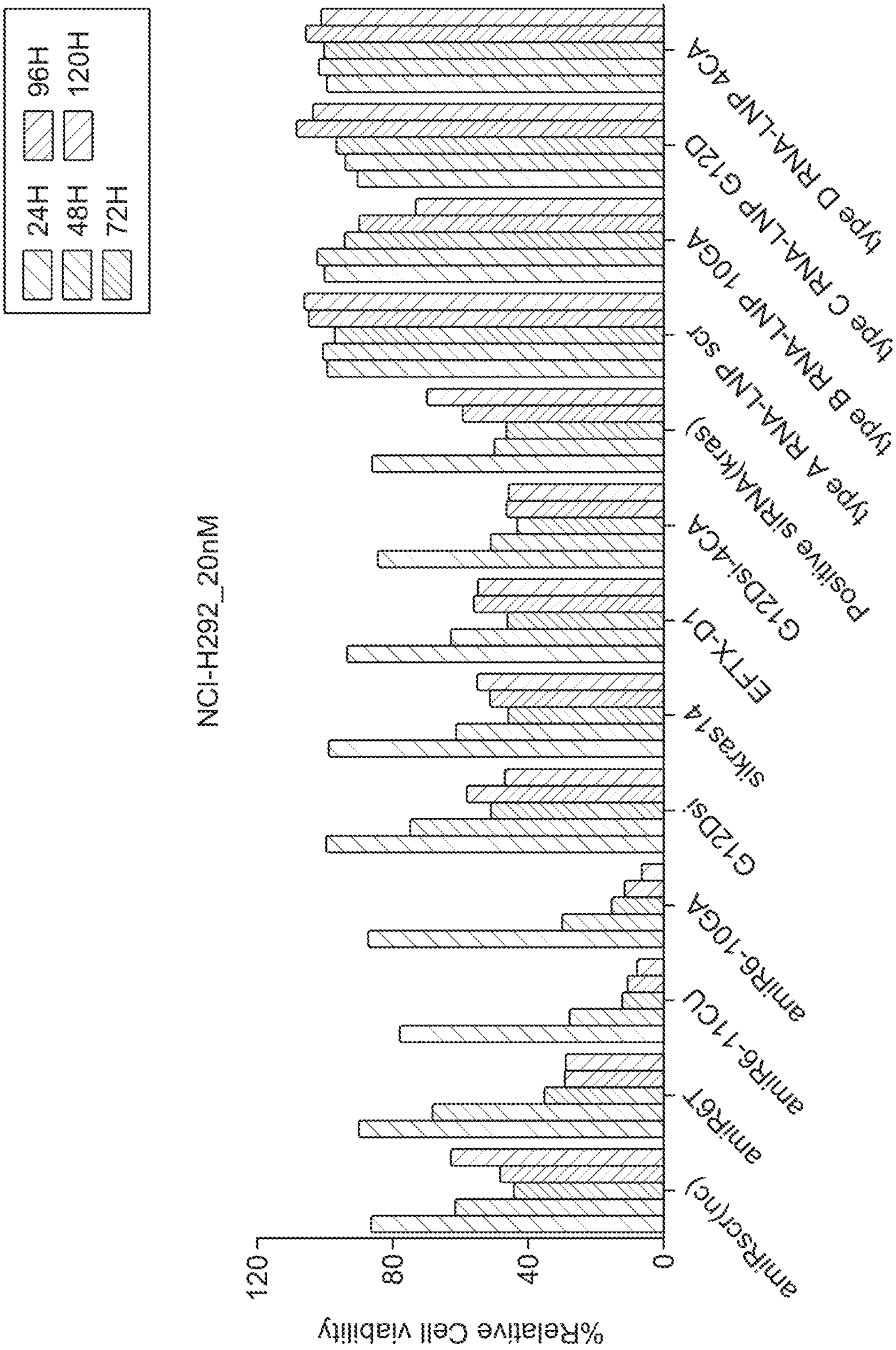
FIG. 18B: Inhibition of NCI-H292 cell growth by amiRs. Relative cell viability was determined following treatment with a transfection agent or with amiR or siRNA loaded in LNPs. 20 nM.

The gene silencing data were averaged and the G12D-to-WT targeting ratios were calculated as shown in FIGS. 15 and 16.

The conclusions of this study are based on average gRTPCR data in cells (WT and Mutant) transfected with 25, 50 and 100 nM amiRs/siRNAs Based on G12D mRNA knockdown, the activity ranking followed G12Dsi-4CA»G12Dsi>amiR6-11CU>amiR6-10GA=EFTX-D1

Based on G12D vs kras WT selectivity, the ranking followed G12Dsi-4CA»amiR6-11CU>amiR6-10GA=amiR6T=G12Dsi So the top candidate for target downregulation efficacy and selectivity based on qRT-PCR were G12Dsi-4CA, amiR6-11CU, G12Dsi, and amiR6-10GA Overall Conclusions of this study are: G12Dsi-4CA, amiR6-10GA, amiR6-11CU, and G12Dsi are all improved designs compared to the previously reported amiR6 (Acunzo et al) and siRNA EFTX-D1 (Papke et al). In fact, EFTX-D1 did not perform well both in terms of efficiency and G12D selectivity. G12Dsi-4CA had the best overall G12D selectivity profile among the sequences tested while the others are also very promising.

The General Approach of the amiR and siRNA Designs

The method described above for designing amiRs and siRNAs described above can readily be applied to other kras mutants and to point mutations in general. The generalized design approach is as follows:

For amiR design, the $7^{th}$ nt of the guide strand should match with the mutant target sequence (mismatched against the WT sequence). The rest of the amiR should perfectly match the corresponding target sequence except for position 10 or position 11 (e.g., using G to A or C to U substitution), introducing an additional mismatch. So the overall number of mismatches for mutant is 1 nt (in the center) and for WT is 2 nt (1 in seed region, 1 in center). The following are examples of this design method applied to targeting G12S (listed by guide-strand only):

```
amiR6-G12S (as reported by Acunzo et al article):
                                        (SEQ ID NO: 14)
CGCCACUACGACCAACUACCAC

amiR6-G12S no bulge
                                        (SEQ ID NO: 15)
CGCCACUAGCUCCAACUACCAC

amiR6-G12S-10UC
                                        (SEQ ID NO: 16)
CGCCACUAGCCCCAACUACCAC

amiR6-G12S-11CU
                                        (SEQ ID NO: 17)
CGCCACUAGCUUCAACUACCAC
```

The same approach can be used to design amiR sequences targeting G12V, G13D, G12C, and any other kras point mutated variants. In a typical amiR design, 2-3 phosphorothioate linkages are incorporated in both the 5' and the 3' ends. The passenger strand would be fully complementary to the guide strand. In addition, dTdT may be added to each strand to produce a 2nt 3' overhang.

For designing siRNA for targeting kras mutant. Variants of G12Dsi and G12Dsi4CA can be easily designed to target other kras mutants. The variant would have 0-1 nt mismatch with the point mutated target sequence and 1-2 nt mismatch against kras WT. For example, to target kras G12C, the following guide strands can be used:

```
G12Csi guide strand
                                        (SEQ ID NO: 18)
UUGCCUACGCCACAAGCUC

G12Csi-4CA guide strand
                                        (SEQ ID NO: 19)
UUGACUACGCCACAAGCUC
```

The same approach can be used to design amiR sequences targeting G12V, G13D, G12C, and any other kras point mutated variants. In a typical siRNA design, 2-3 phosphorothioate linkages are incorporated in both the 5' and 3' ends. The passenger strand would be fully complementary to the guide strand. In addition, dTdT may be added to each strand to produce a 3' 2nt overhang.

Evaluation of LNP-kras amiR/siRNA in Vitro

Tumor cell inhibition by 10GA, 4CA, and G12Dsi, along with EFTX-D1, amiRscr, and positive control (seq 2 from Kopke article) were analyzed by cell viability assay at 10 nM and 20 nM in ASPC-1 (G12D) and NCI-H292 (WT) cells using lipofectamine transfection agent. 10GA, 4CA, and G12Dsi were also studied in LNP format, which was designed for in vivo delivery. The results are provided in FIGS. 17A, 17B, 18A, and 18B.

First, for the LNPs, the in vitro activity was generally low (LNPs are designed for in vivo). 10GA at 20 nM seemed to have a slight effect in both cell types. The effect was stronger in H292 (WT) cells. This might be due to H292 having a stronger kras dependency.

For all amiR/siRNAs using lipofectamine transfection agent, the cytotoxicy effect in Aspc-1 cells followed the sequence of 11CU=10GA>6T>G12Dsi>sikras14=4CA=EFTX-D1=positive control (seq 2)>amiRscr For all amiR/siRNAs using lipofectamine transfection agent, the cytotoxicy effect in H292 cells followed the sequence of 11CU=10GA>6T»G12Dsi=sikras14=4CA=EFTX-D1=positive control (seq 2)=amiRscr.

Therefore, based on the in vitro cell inhibition, 11CU and 10GA had the highest activity that was higher than those of the siRNA-based agents. Sequences from the literature (EFTX-D1, seq 2) were ineffective in terms of cellular inhibition. The amiRs are superior RNAi agents in terms of cytotoxicity.

Synthesis and Characterization of Lipid Nanoparticles (LNPs) with New Ionizable Lipids and are Free of Ethanol amiR and siRNA samples were synthesized by Wuxi STA according to our designs and purified by HPLC.

Material and Methods 1,2-Dioleyloxy-3-dimethylaminopropane (DODMA), 1,2-dioleoyl-sn-glycero-3-phosphoethanolamine (DOPE), cholesterol, acetic acid and sodium acetate were purchased from Sigma. 1,2-dilinoleyloxy-n,n-dimethyl-3-aminopropane (DLin-DMA) and (6Z, 9Z, 28Z, 31Z)-Heptatriaconta-6,9,28,31-tetraen-19-yl 4-(dimethylamino)butanoate (Dlin-MC3-DMA) were obtained from MedChemExpress and Nanosoft polymers, respectively. L-Histidine was purchased from Roth. Ethanol, RNAse-free water, and Slide-A-Lyzer™ Dialysis Cassettes (10 kD, 12-30 mL) were purchased from VWR. RNAs were purchased from Wuxi AppTec.

| RNA Abbreviation | Short Name | Sequence | Anhydrous MW (g/mol) | Purity (%) |
|---|---|---|---|---|
| A | amiRscrA | 5'-rUrUrCrUrCrCrGrArArCrGrUrGrUrCrArCrGrU-3' (SEQ ID NO: 33)<br>5'-rArCrGrUrGrArCrArCrGrUrUrCrGrGrArGrArA-3' (SEQ ID NO: 34) | 12098.3 | 99.13% |
| B | amiR-seq2 | 5'-rGrUrCrUrCrUrUrGrGrArUrArUrUrCrUrCrGrA-3' (SEQ ID NO: 21)<br>5'-rUrCrGrArGrArArUrArUrCrCrArArGrArGrArC-3' (SEQ ID NO: 35) | 12068.3 | 97.78% |
| C | amiR6-10GA | 5'-rA*rC*rGrCrCrArUrCrArArCrUrCrCrArArCrUrArCrCrA*dT*dT-3' (SEQ ID NO: 36)<br>5'-rU*rG*rGrUrArGrUrUrGrGrArGrUrUrGrArUrGrGrCrGrU*dT*dT-3' (SEQ ID NO: 37) | 15364.4 | 93.54% |
| D | G12Dsi | 5'-rU*rU*rGrCrCrUrArCrGrCrCrArUrCrArGrCrUrC*dT*dT-3' (SEQ ID NO: 38)<br>5'-rG*rA*rGrCrUrGrArUrGrGrCrGrUrArGrGrCrArA*dT*dT-3' (SEQ ID NO: 39) | 13458.3 | 98.73% |

LNPs Preparation

Stock solutions of lipids were prepared in ethanol. DODMA chloroform solution (Sigma, 890899C-100MG) was evaporated at 40° C. using a vacuum evaporator (Genevac EZ-2 Elite, automated program for low boiling point solvent) and then solubilized at 20 g/L in ethanol at 40° C. DLin-DMA, DLin-MC3-DMA, DOPE and $PEG_{2000}$-DMG were solubilized at 20 g/L in ethanol whereas cholesterol solution was prepared at 10 g/L.

A solution composed of ionizable lipid/DOPE/cholesterol/$PEG_{2000}$ -DMG at a ratio 46:26:26:2 mol/mol was prepared in ethanol at 8 g/L for each ionizable lipid (DODMA, DLin-DMA and DLin-MC3-DMA) and was heated to 40° C.

In parallel, acetate buffer was prepared with 45 mM acetic acid and 5 mM sodium acetate in RNAse-free water. RNA solutions at 0.8 g/L and sucrose 20% were prepared in RNAse-free water. All solutions were heated to 40° C.

The ionizable lipid/DOPE/cholesterol/$PEG_{2000}$-DMG lipid solution (2.5 mL, 8 g/L) was rapidly injected into the acetate buffer (2.5 mL) at 40° C. under magnetic stirring at 200 rpm. RNA solution (5 mL, 0.8 g/L) was rapidly added to this mix at 40° C. under magnetic stirring at 100 rpm, followed by rapid injection of sucrose 20% (10 mL) under the same conditions. The resulting LNPs (20 mL) were subsequently dialyzed against 2 times 1 L of sucrose 10% and 10 mM L-Histidine (pH=7.4) using a Slide-A-Lyzer cassette to remove ethanol (bath change after 4 h or overnight). Finally, LNPs were filtered through a 0.45 μm PES sterile filter for sterilization and stored at −20° C.

LNPs Characterization

DLS

DLS measurements were carried out on a Zetasizer Pro (Malvern Panalytical) equipped with a He—Ne laser (633 nm), at 25° C. and a scattering angle of 174.8°. The software used was ZS Explorer. A low-volume plastic cell of 10 mm optical path length was filled with 70 μL of the sample. The viscosity of the dispersant was corrected according to the solvent or mixture of solvents used. Data were acquired on three different measurements with automatic optimization of the number and duration of runs per measurement. Results are expressed as an average of these measurements. $D_h$ of the objects is the intensity mean for each population. PDI is calculated from the autocorrelation functions using the cumulant method.

Zeta-Potential

Zeta-potential measurements were carried out on a Zetasizer Pro (Malvern Panalytical) equipped with a He—Ne laser (633 nm), at 25° C. and a scattering angle of 174.8°. The software used was ZS Explorer. A folded capillary cell (DTS1070) was filled with 1 mL of sample diluted 1:100 in water. Data were acquired on five different automatic measurements. Results are expressed as an average of these five measurements.

Figure 19:
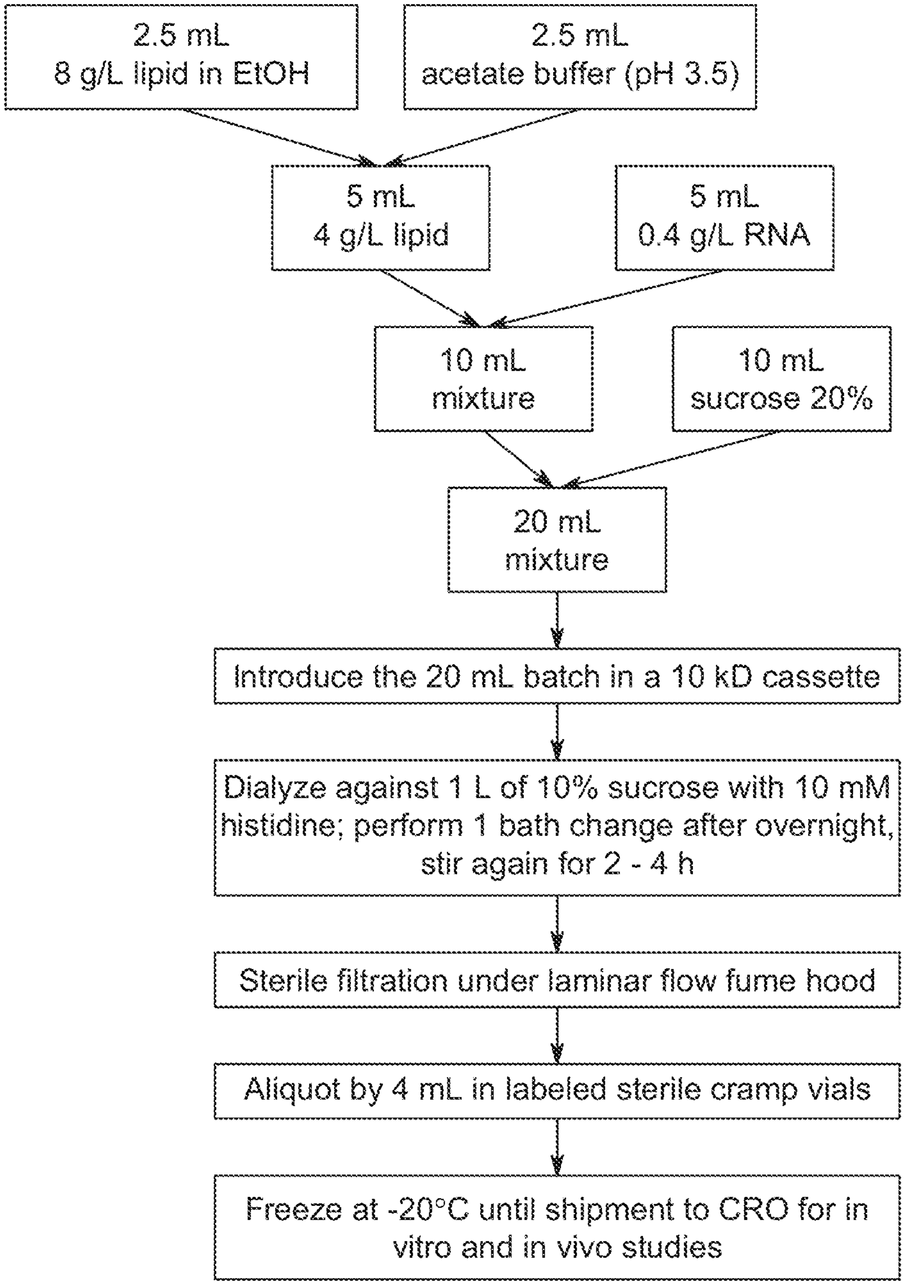
FIG. 19. Flowchart for preparation of LNPs loaded with amiR or siRNA.

LNP preparation was performed as follows at PMC Isochem in France according to FIG. 19.

The resulting LNPs were characterized by dynamic light scattering for particle size. The mean particle size was found to be <150 nm.

Figure 20:
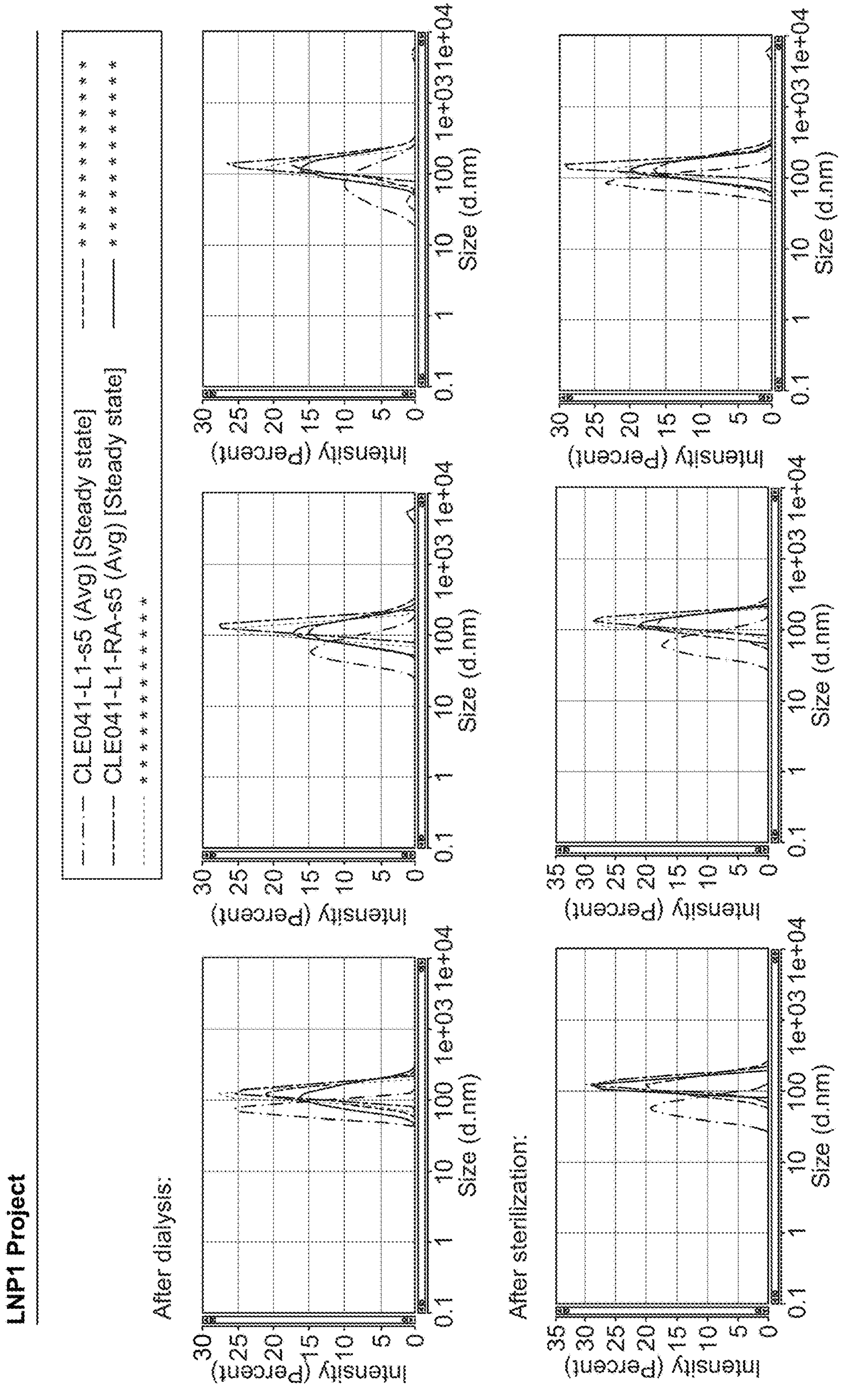
FIG. 20. Particle size distributions of LNPs following dialysis and then sterile filtration.

The particle sizes were measured after dialysis and again after sterilization. Results are plotted in FIG. 20.

The resulting LNP products have the following compositions:

Composition of the RNA lipid nanoparticles (RNA-LNPs):

| Product name | CAS number: | % w/w |
|---|---|---|
| Ribonucleic acid (RNA), modified (chemically synthesized):<br>-RNA type A of sequence:<br>5'-rUrUrCrUrCrCrGrArArCrGrUrGrUrCrArCrGrU-3'<br>5'-rArCrGrUrGrArCrArCrGrUrUrCrGrGrArGrArA-3'<br>-RNA type B of sequence:<br>5'-rGrUrCrUrCrUrUrGrGrArUrArUrUrCrUrCrGrA-3'<br>5'-rUrCrGrArGrArArUrArUrCrCrArArGrArGrArC-3'<br>-RNA type C of sequence:<br>5'-rA*rC*rGrCrCrArUrCrArArCrUrCrCrArArCrUrArCrCrA*dT*dT-3'<br>5'-rU*rG*rGrUrArGrUrUrGrGrArGrUrUrGrArUrGrGrCrGrU*dT*dT-3'<br>-RNA type D of sequence:<br>5'-rU*rU*rGrCrCrUrArCrGrCrCrArUrCrArGrCrUrC*dT*dT-3'<br>5'-rG*rA*rGrCrUrGrArUrGrGrCrGrUrArGrGrCrArA*dT*dT-3' | / | 0.015 |
| Lipid:<br>-type 1:<br>1,2-Dioleyloxy-3-dimethylaminopropane (DODMA)<br>-type 2: | 104162-47-2 | |
| 1,2-dilinoleyloxy-n,n-dimethyl-3-aminopropane (DLinDMA)<br>-type 3: | 871258-12-7 | 0.033 |
| (6Z,9Z,28Z,31Z)-Heptatriaconta-6,9,28,31-tetraen-19-yl 4-(dimethylamino)butanoate (Dlin-MC3-DMA)<br>1,2-dioleoyl-sn-glycero-3-phosphoethanolamine (DOPE) | 768593 | 0.022 |
| Cholesterol | 57-88-5 | 0.012 |
| 1,2-Dimyristoyl-rac-glycero-3-methoxypolyethylene glycol-2000 (DMG-PEG2000) | 384835-59-0 | 0.006 |
| Sucrose | 57-50-1 | 9.095 |
| Histidine | 64-19-7 | 0.141 |
| Water, DEPC-Treated | 7732-18-5 | 90.677 |

Composition of the Lipid Nanoparticles (LNPs):

| Product name | CAS number: | % w/w |
|---|---|---|
| Lipid: | | |
| type 1: 1,2-Dioleyloxy-3-dimethylaminopropane (DODMA) | 104162-47-2 | |
| type 2: 1,2-dilinoleyloxy-n,n-dimethyl-3-aminopropane (DLinDMA) | 871258-12-7 | 0.033 |
| type 3: (6Z,9Z,28Z,31Z)-Heptatriaconta-6,9,28,31-tetraen-19-yl 4-(dimethylamino)butanoate (Dlin-MC3-DMA) | 768593 | 0.022 |
| 1,2-dioleoyl-sn-glycero-3-phosphoethanolamine (DOPE) | | |
| Cholesterol | 57-88-5 | 0.012 |
| 1,2-Dimyristoyl-rac-glycero-3-methoxypolyethylene glycol-2000 (DMG-PEG2000) | 384835-59-0 | 0.006 |
| Sucrose | 57-50-1 | 9.096 |
| Histidine | 64-19-7 | 0.141 |
| Water, DEPC-Treated | 7732-18-5 | 90.690 |

The LNPs were then evaluated for tumor cell inhibition in vitro at the CRO Bioduro-Sandia. The protocol used was as follows:

Study Design for LNPs Transfection and Cell Lines Activity Assay

1. Study Objective:

To detect the effect of LNPs on cell line viability and proliferation.

2. Study Design:

Transfect the LNP-siRNA into Bxpc-3 and HUVEC cell lines, knock down the mRNA level of KRAS gene, and use CTG method to detect the cell line viability and proliferation at 24 h, 48 h, 72 h, 96 h, and 120 h.

3. Material and Methods:

3.1 Cell Lines

| Cell line | Medium |
|---|---|
| Bxpc-3 | 1640 + 10% FBS + 1% P/S |
| HUVEC | HUVEC Complete Medium (BEGM kit + 10% FBS) |

3.2 Reagent

CellTiter-Glo® Luminescent Cell Viability Assay (Promega Cat #G7573).

RPMI 1640 Medium (Gibco Cat #11415-064).

Trypsin-EDTA (0.25%) (STEMCELL Cat #09701).

FBS (ExCell Bio Cat #FND500).

Phosphate Buffered Saline (PBS) (Gibco Cat #C20012500BT).

Penicillin/Streptomycin (100×) (Gibico Cat #15140-122).

Sodium Pyruvate (100 mM) (Gibco Cat ##11360-070)

Lipofectamine RNAi MAX (Thermo Fisher Cat #13778075).

Dimethyl sulfoxide (DMSO) 100 mL (Sigma Cat #D2650-100 mL).

HUVEC Complete Medium (Pricella Cat #CM-0122)

15 LNPs list in the table as below.

| LNP | API |
|---|---|
| DODMA (L1) | AmiR6-10GA (type A)<br>G12DSi (type B)<br>Pos amiR-seq2 (type D)<br>empty |
| DLIN-DMA (L2) | AmiR6-10GA (type A)<br>G12DSi (type B)<br>Pos amiR-seq2 (type D)<br>empty |

-continued

| LNP | API |
|---|---|
| DLIN-MC3-DMA (L3) | AmiR6-10GA (type A)<br>G12DSi (type B)<br>Neg amiRscrA (type C)<br>Pos amiR-seq2 (type D)<br>empty |

3.3 Instruments

Cell counter: Counter star (Ruiyu-biotech)

CO2 cell incubator: MCO-15AC (Thermo Fisher)

Pipette: BioHit Multichannel, 50-1200 μL (RAININ Multichannel).

Pipette: 0.2-10 μL, 10-300 μL, 5-50 μL (Eppendorf)

Centrifuge: Centrifuge ST 40R (Thermo Fisher)

Water system: Milli-Q Reference system (Millipore)

Perkin Elmer Envision 2104 Multilabel Reader (No. 01-094-0002)

4. Assay Protocol 4.1 Preparation of Cell Assay Plates: Day 1

1) Pre-warm Trypsin-EDTA (0.25%), cell medium with 37° C. water bath.
2) Observe cells under a microscope to assess the degree of confluency and confirm the absence of bacterial and fungal contaminants.
3) Remove medium, wash cells with 10 mL PBS twice. Add 2 mL 0.25% Trypsin/EDTA reagent for a T-75 flask. Put flask in the incubator for a few minutes, or until cells have detached. Add 7 mL of fresh cell medium contain 10% FBS, rinse the cells and transfer to a centrifuge tube.
4) Centrifuge the collected cells at 200 g for 5 minutes, at room temperature.
5) After centrifugation, discard the supernatant. Resuspend the cell pellet with 5 mL complete cell medium.
6) Remove 20 μL of the resuspended cells to count cells. Count cells by adding 20 μL cell suspension to 20 μL dye with Cell Counter Star, record live cell number and viability in cell tracking sheet.
7) Using complete cell medium, adjust the volume of the suspension to achieve a cell concentration.
8) The seeding density of cell lines is 2000 in 90 μL per well in 96-well plate. Incubate the cell lines overnight at 5% $CO_2$ and 37° C. Perform in triplicate. Seeding 10 plates for each cell line.

4.2 LNPs Transfection: Day 2

For LNPs Transfection:

Before transfection, mix the LNPs gently with tips.

Prepare 10× concentration of LNPs as below.

| SIRNA | Molecular weight | Stock Concentration (mg/mL) | Stock Concentration (uM) | Stock Solution Volume (uL) | Medium Volume (uL) | 10× concentration |
|---|---|---|---|---|---|---|
| amiRscrA | 12038.3 | 0.16 | 13.2909 | 5 | 61.45 | 1 uM |
| amiR-seq2 | 12068.3 | 0.16 | 13.2579 | 5 | 61.29 | 1 uM |
| amiR6-10GA | 15364.4 | 0.16 | 10.4137 | 5 | 47.07 | 1 uM |
| G12Dsi | 13458.3 | 0.16 | 11.8886 | 5 | 54.44 | 1 uM |
| empty | | | | 5 | 61.45 | |

For 100 nM LNPs, add 10 uL 1 uM LNPs to 90 uL cells according to the plate map. Do in duplicate.

For 50 nM LNPs, add 5 uL 1 uM LNPs+5 uL Medium to 90 uL cells according to the plate map. Do in duplicate.

Total twenty plates, each plate for one concentration and one time point and one cell line.

4.2 CTG Detect: Day 3-7 (at 24 h, 48 h, 72 h, 96 h and 120 h)

1) Incubate the plates at room temperature and away from light for 30 minutes.
2) Thaw three vials of CellTiter-Glo® Reagent at room temperature and equilibrated them to room temperature prior to use. Avoid light.
3) Add 100 μL/well of CellTiter-Glo® Reagent in each well. Avoid light.
4) Mix contents for 2 minutes on an orbital shaker.
5) Incubate plate at room temperature for 10 minutes to stabilize the luminescent signal. Read plates in Envision.

5. Results Analysis

The surviving rate (%)=((LumTest article−LumBlank control)/(LumVehicle control−LumBlank control))×100%

Figure 21A:
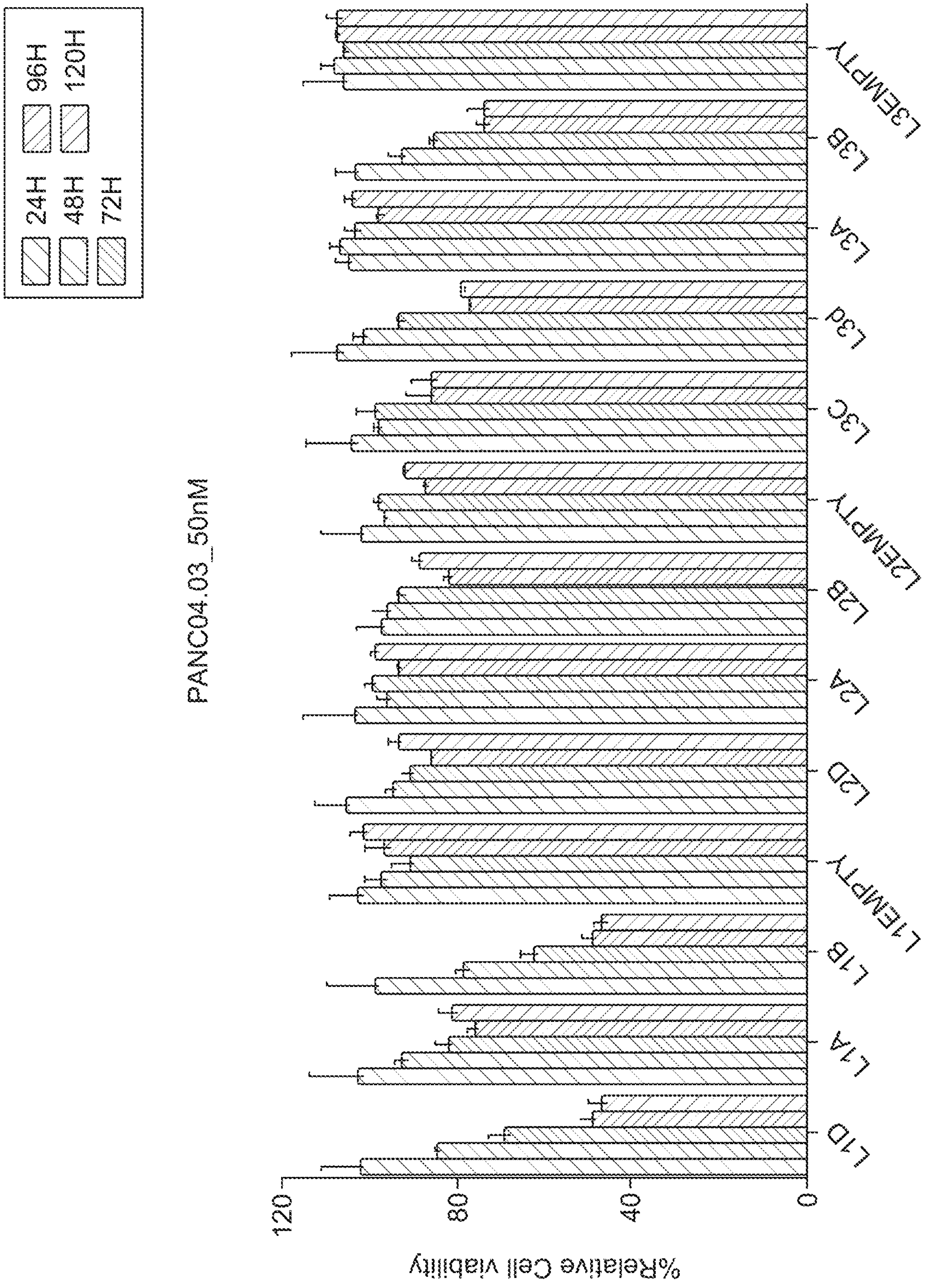
FIG. 21A: Inhibition of growth of PAN0403 cells by LNPs loaded with amiR or siRNA. 50 nM; L1: DODMA-based, L2: DlinDMA-based, L3: DlinMC3DMA-based. A. amiR6-10GA; B. G12Dsi; C. Scrambled control; D. Seq-2 siRNA positive control.
Figure 21B:
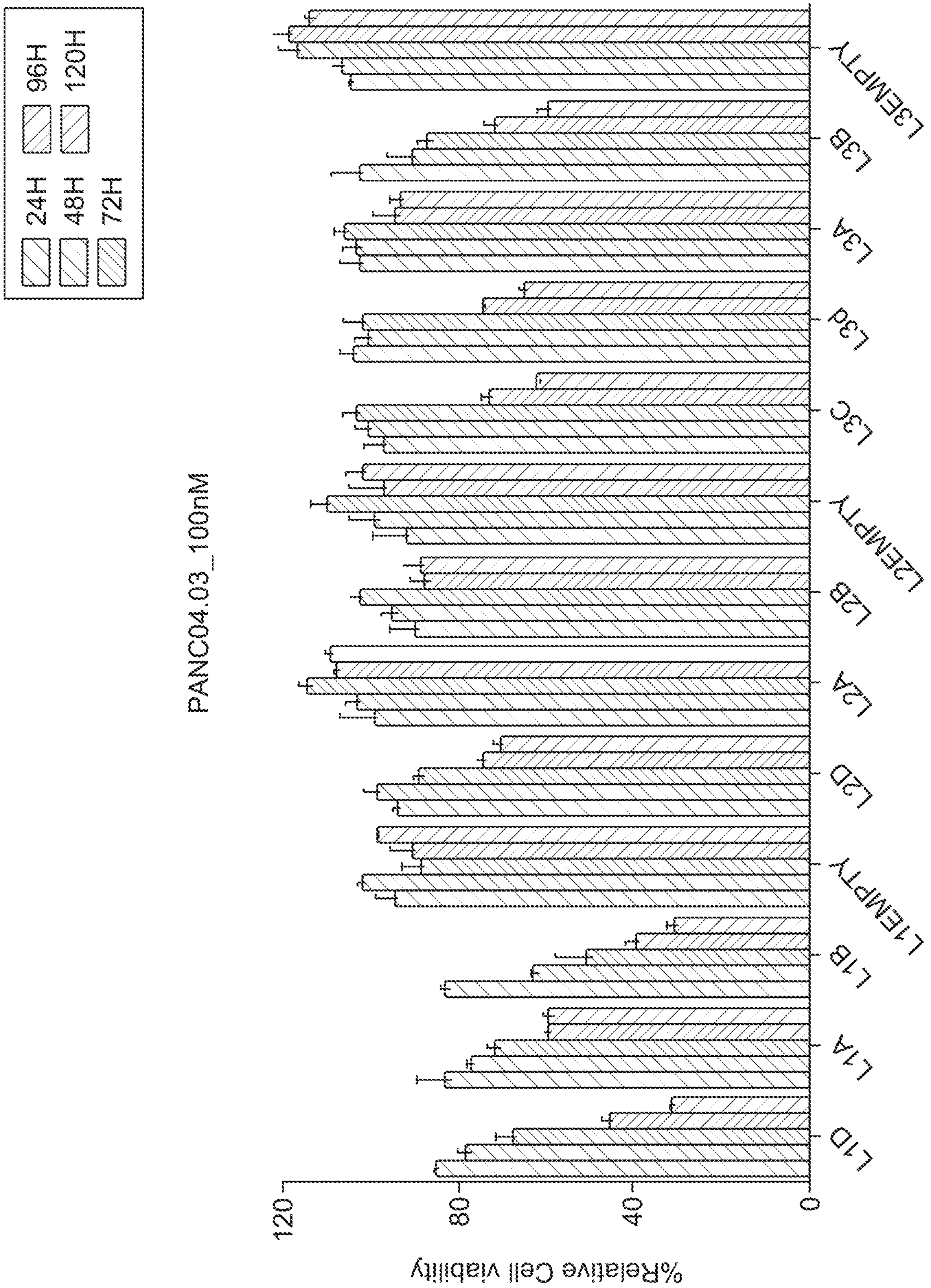
FIG. 21B: Inhibition of growth of PAN0403 cells by LNPs loaded with amiR or siRNA. 100 nM. L1: DODMA-based, L2: DlinDMA-based, L3: DlinMC3DMA-based. A. amiR6-10GA; B. G12Dsi; C. Scrambled control; D. Seq-2 siRNA positive control.
Figure 22A:
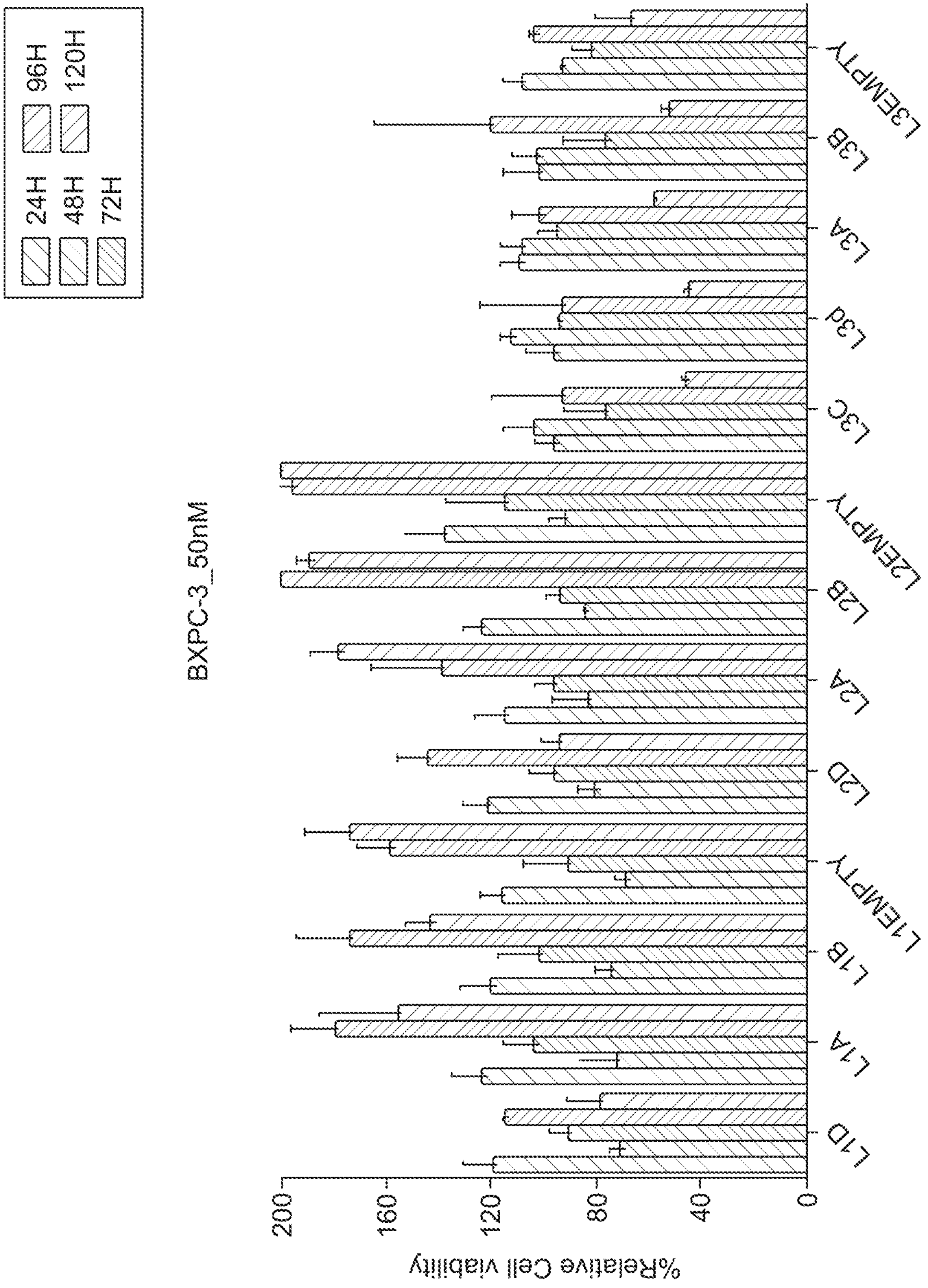
FIG. 22A: Inhibition of growth of BxPC-3 cells by LNPs loaded with amiR or siRNA. 50 nM; L1: DODMA-based, L2: DlinDMA-based, L3: DlinMC3DMA-based. A. amiR6-10GA; B. G12Dsi; C. Scrambled control; D. Seq-2 siRNA positive control.
Figure 22B:
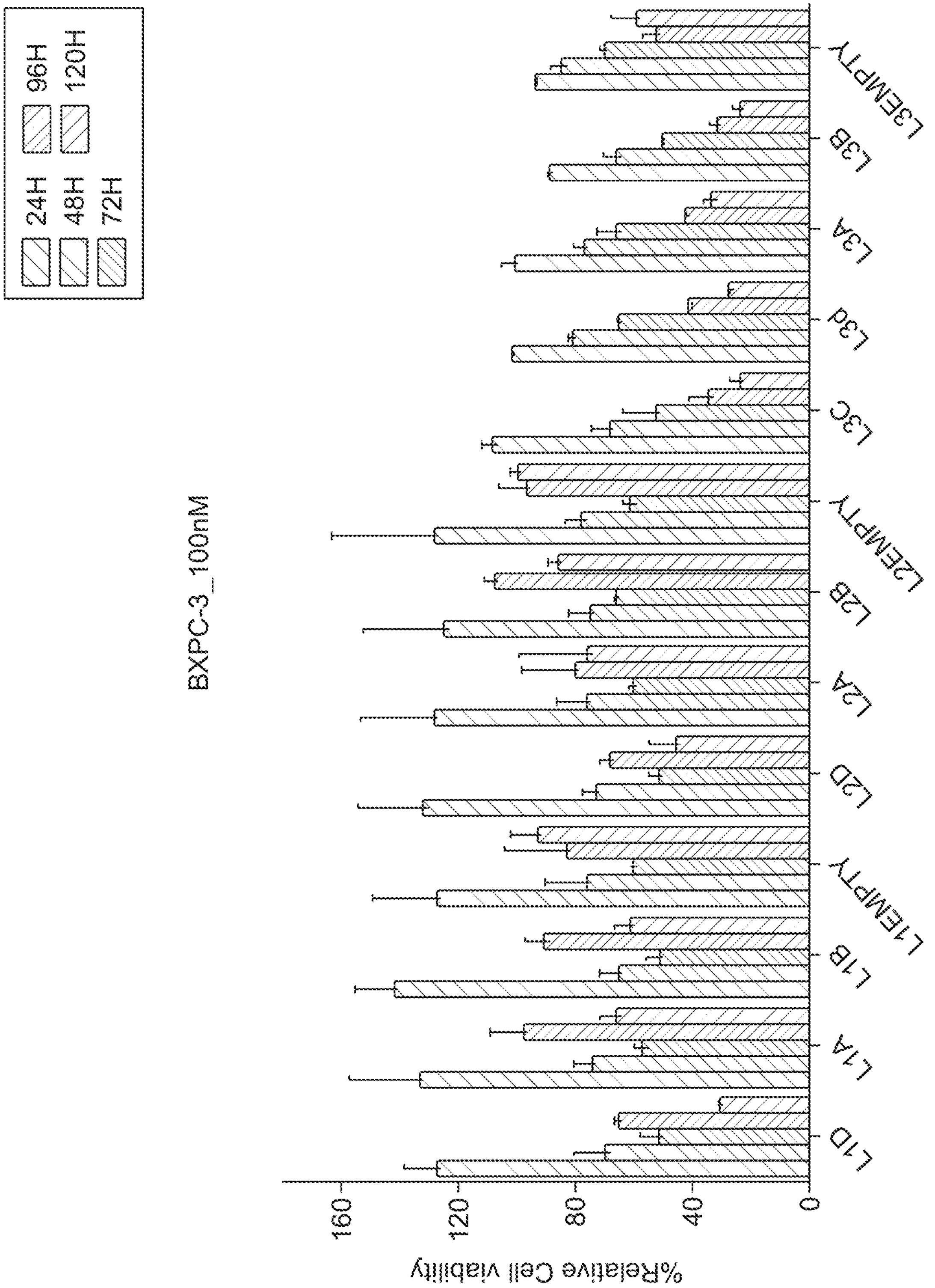
FIG. 22B: Inhibition of growth of BxPC-3 cells by LNPs loaded with amiR or siRNA. 100 nM. L1: DODMA-based, L2: DlinDMA-based, L3: DlinMC3DMA-based. A. amiR6-10GA; B. G12Dsi; C. Scrambled control; D. Seq-2 siRNA positive control.

First, for PAN0403 cells, the data are provided in FIGS. 21A-21B. Then the data for BxP3 cells are provided in FIGS. 22A-22B.

Figure 23A:
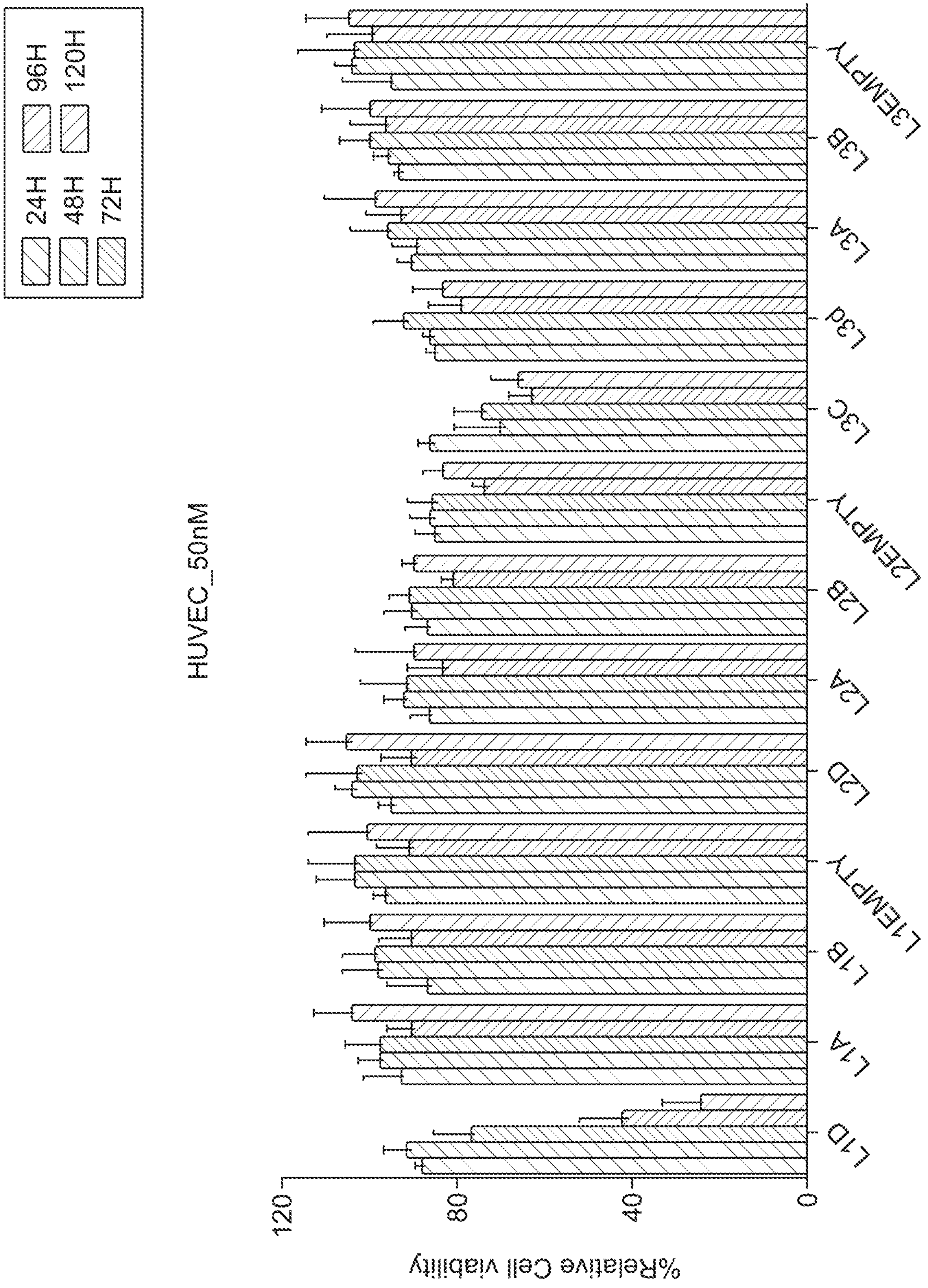
FIG. 23A: Inhibition of growth of HUVEC cells by LNPs loaded with amiR or siRNA. 50 nM; L1: DODMA-based, L2: DlinDMA-based, L3: DlinMC3DMA-based. A. amiR6-10GA; B. G12Dsi; C. Scrambled control; D. Seq-2 siRNA positive control.
Figure 23B:
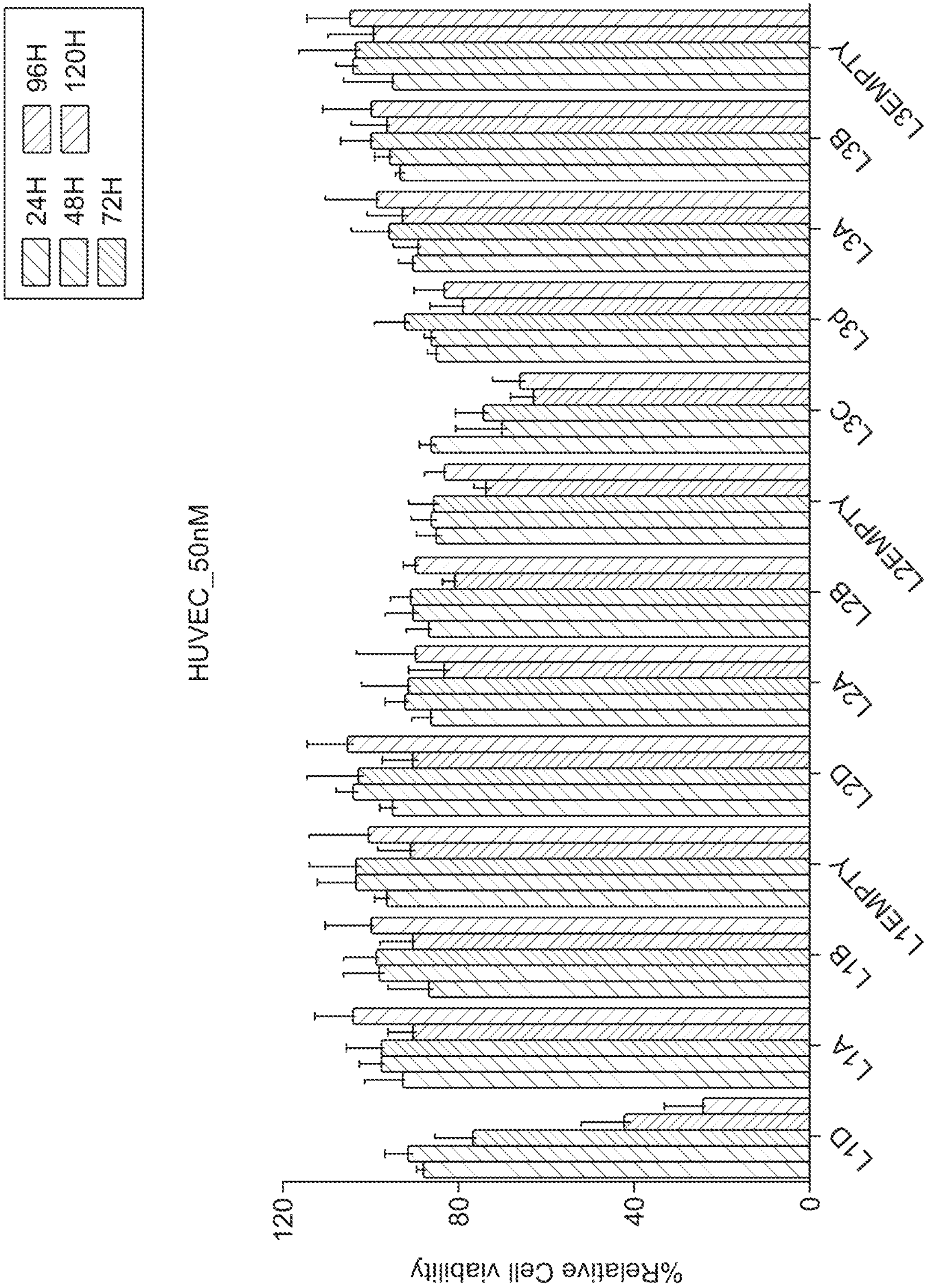
FIG. 23B: Inhibition of growth of HUVEC cells by LNPs loaded with amiR or siRNA. 100 nM. L1: DODMA-based, L2: DlinDMA-based, L3: DlinMC3DMA-based. A. amiR6-10GA; B. G12Dsi; C. Scrambled control; D. Seq-2 siRNA positive control.

FIGS. 23A and 23B provides inhibition of growth of HUVEC cells by LNPs loaded with amiR or siRNA. 29A: 50 nM; 29B: 100 nM. L1: DODMA-based, L2: DlinDMA-based, L3: DlinMC3DMA-based. A. amiR6-10GA; B. G12Dsi; C. Scrambled control; D. Seq-2 siRNA positive control The results showed that amiRs 10GA and 12Dsi were able to inhibit the growth of tumor cells while weakly inhibitive in normal endothelial HUVEC cells. In contrast, the scr control and seq2 siRNA showed much less selectivity toward tumor cells, causing relatively greater cytotoxicity in HUVEC cells. BxPC-3 is kras WT. HUVEC is kras WT and non-cancerous normal human vascular endothelial cells. So lack of toxicity in HUVEC cells and BxPC-3 indicates potential reduced toxicity to normal tissues.

Then the LNPs were evaluated in an in vivo efficacy study at Bioduro-Sandia.

Protocol for In Vivo Anti-Tumor Efficacy Study of Test Drug in Panc0403 Subcutaneous Model in B-NDG Mice 1. Study Objective: Evaluate the Anti-Tumor Efficacy Study of Test Drug in Panc0403 Subcutaneous Model in B-NDG Mice.
2. Study Design:

Treatment group and dosing:

| | Group | Animal Number | Treatment (mg/kg) | Frequency & Route | Dose Volume (mL/kg) | Treatment time |
|---|---|---|---|---|---|---|
| 1 | Type-1 | 6 | 0 | i.v. q2d × 10 | 10 | 21 days |
| 2 | Type 1-A | 6 | 2 | i.v. q2d × 10 | 10 | 21 days |
| 3 | Type 1-B | 6 | 2 | i.v. q2d × 10 | 10 | 21 days |
| 4 | Type 1-D | 6 | 2 | i.v. q2d × 10 | 10 | 21 days |
| 5 | Type-3 | 6 | 0 | i.v. q2d × 10 | 10 | 21 days |
| 6 | Type 3-A | 6 | 2 | i.v. q2d × 10 | 10 | 21 days |
| 7 | Type 3-B | 6 | 2 | i.v. q2d × 10 | 10 | 21 days |
| 8 | Type 3-C | 6 | 2 | i.v. q2d × 10 | 10 | 21 days |
| 9 | Type 3-D | 6 | 2 | i.v. q2d × 10 | 10 | 21 days |

| LNP | API |
|---|---|
| DODMA (Type1) | empty<br>A-AmiR6-10GA<br>B-G12DSi<br>D-Pos amiR-seq2 |
| DLIN-MC3-DMA(Type3) | empty<br>A-AmiR6-10GA<br>B-G12DSi<br>C-Neg amiRscrA<br>D-Pos amiR-seq2 |

3. Materials:

3.1 Animals and Housing Conditions

Species: Mus Musculus

Strain: B-NDG mice

Age: 6-8 weeks

Sex: female

Number of animals: 135 mice

Animal supplier: Beijing Biocytogen Co., Ltd.

3.2 Test Articles

Supplier: Nanothera Biosciences, Inc

Storage condition: −80° C.

Product Identification:

| RNA | Sequence Name | Manufacturing ID Wuxi | Sequence | Anhydrous MW (g/mol) | Purity (%) | Quantity received |
|---|---|---|---|---|---|---|
| A | amiRscrA | ET62426-16-P1 | 5'-rUrUrCrUrCrCrGrArArCrGrUrGrUrCrArCrGrU-3'<br>5'-rArCrGrUrGrArCrArCrGrUrUrCrGrGrArGrArA-3' | 12098.3 | 99.13% | 50 mg (5 aliquots of 10 mg) |
| B | amiR-seq2 | ET62507-10-P1 | 5'-rGrUrCrUrCrUrUrGrGrArUrArUrUrCrUrCrGrA-3'<br>5'-rUrCrGrArGrArArUrArUrCrCrArArGrArGrArC-3' | 12068.3 | 97.78% | 50 mg (5 aliquots of 10 mg) |

-continued

| RNA | Sequence Name | Manufacturing ID Wuxi | Sequence | Anhydrous MW (g/mol) | Purity (%) | Quantity received |
|---|---|---|---|---|---|---|
| C | amiR6-10GA | ET63373-2-P1 | 5'-rA*rC*rGrCrCrArUrCrArArCrU rCrCrArArCrUrArCrCrA*dT*dT-3' 5'-rU*rG*rGrUrArGrUrUrGrGrArG rUrUrGrArUrGrGrCrGrU*dT*dT-3' | 15364.4 | 93.54% | 50 mg (5 aliquots of 10 mg) |
| D | G12Dsi | ET6373-2-P2 | 5'-rU*rU*rGrCrCrUrArCrGrCrC rArUrCrArGrCrUrC*dT*dT-3' 5'-rG*rA*rGrCrUrGrArUrGrGrCrG rUrArGrGrCrArA*dT*dT-3' | 13458.3 | 98.73% | 50 mg (5 aliquots of 10 mg) |

Composition of the RNA Lipid Nanoparticles (RNA-LNPs):

| Product name | CAS number: | % w/w |
|---|---|---|
| Ribonucleic acid (RNA), modified (chemically synthesized): -RNA type A of sequence: 5'-rUrUrCrUrCrCrGrArArCrGrUrGrUrCrArCrGrU-3' 5'-rArCrGrUrGrArCrArCrGrUrUrCrGrGrArGrArA-3' -RNA type B of sequence: 5'-rGrUrCrUrCrUrUrGrGrArUrArUrUrCrUrCrGrA-3' 5'-rUrCrGrArGrArArUrArUrCrCrArArGrArGrArC-3' -RNA type C of sequence: 5'-rA*rC*rGrCrCrArUrCrArArCrUrCrCrArArCrUrArCrCrA*dT*dT-3' 5'-rU*rG*rGrUrArGrUrUrGrGrArGrUrUrGrArUrGrGrCrGrU*dT*dT-3' -RNA type D of sequence: 5'-rU*rU*rGrCrCrUrArCrGrCrCrArUrCrArGrCrUrC*dT*dT-3' 5'-rG*rA*rGrCrUrGrArUrGrGrCrGrUrArGrGrCrArA*dT*dT-3' | / | 0.015 |
| Lipid: -type 1: 1,2-Dioleyloxy-3-dimethylaminopropane (DODMA) -type 2: | 104162-47-2 | |
| 1,2-dilinoleyloxy-n,n-dimethyl-3-aminopropane (DLinDMA) -type 3: | 871258-12-7 | 0.033 |
| (6Z,9Z,28Z,31Z)-Heptatriaconta-6,9,28,31-tetraen-19-yl 4-(dimethylamino)butanoate (Dlin-MC3-DMA) 1,2-dioleoyl-sn-glycero-3-phosphoethanolamine (DOPE) | 768593 | 0.022 |
| Cholesterol | 57-88-5 | 0.012 |
| 1,2-Dimyristoyl-rac-glycero-3-methoxypolyethylene glycol-2000 (DMG-PEG2000) | 384835-59-0 | 0.006 |
| Sucrose | 57-50-1 | 9.095 |
| Histidine | 64-19-7 | 0.141 |
| Water, DEPC-Treated | 7732-18-5 | 90.677 |

Give sufficient volume (~255 ul of 0.157 siRNA in LNPs) to reach 2 mg/kg for each dose. For the 5 vials, open one vial at a time and once thawed store in a 4-degree fridge until used up rather than re-freeze.

4 Experimental Methods and Procedures:

4.1 Cell Culture

The Panc0403 tumor cells will be cultured in 1640 medium supplemented with 15% heat inactivated fetal bovine serum with 10 ug/ml insulin, 100 U/ml penicillin and 100 μg/ml streptomycin at 37° C. in an atmosphere of 5% CO2 in air. The tumor cells will be routinely subcultured 2 to 3 times weekly. The cells growing in an exponential growth phase will be harvested and counted for tumor inoculation.

4.2 Tumor Inoculation and Grouping

Each mouse will be inoculated subcutaneously at the right flank with the PAN0403 tumor cells ($5\times10^6$ per mouse) in 0.1 mL RPMI1640 medium with 50% matrigel for tumor development. 90 animals will be randomized using block randomization by Excel based upon their tumor volume (around 125 $mm^3$). This ensures that all the groups are comparable at the baseline.

4.3 Observations

All the procedures related to animal handling, care and the treatment in this study will be performed according to the guidelines approved by the Institutional Animal Care and Use Committee (IACUC) of BioDuro following the guidance of the Association for Assessment and Accreditation of Laboratory Animal Care (AAALAC). At the time of routine monitoring, the animals will be checked for any adverse effects of tumor growth and/or treatment on normal behavior such as effects on mobility, food and water consumption (by observation only), and body weight gain/loss (body weights will be measured twice weekly in the pre-dosing phase and daily in the dosing phase, have a record twice weekly), eye/hair matting and any other abnormal effect, including tumor ulceration. Unexpected deaths and observed clinical signs will be recorded based on the numbers of animals within each subset. Animals will not be allowed to become moribund.

4.4 Tumor Measurements

Tumor volume will be measured twice weekly in two dimensions using a caliper, and the volume will be expressed in $mm^3$ using the formula: $V=0.5\ a \times b^2$, where a and b are the long and short diameters of the tumor, respectively.

Figure 24:
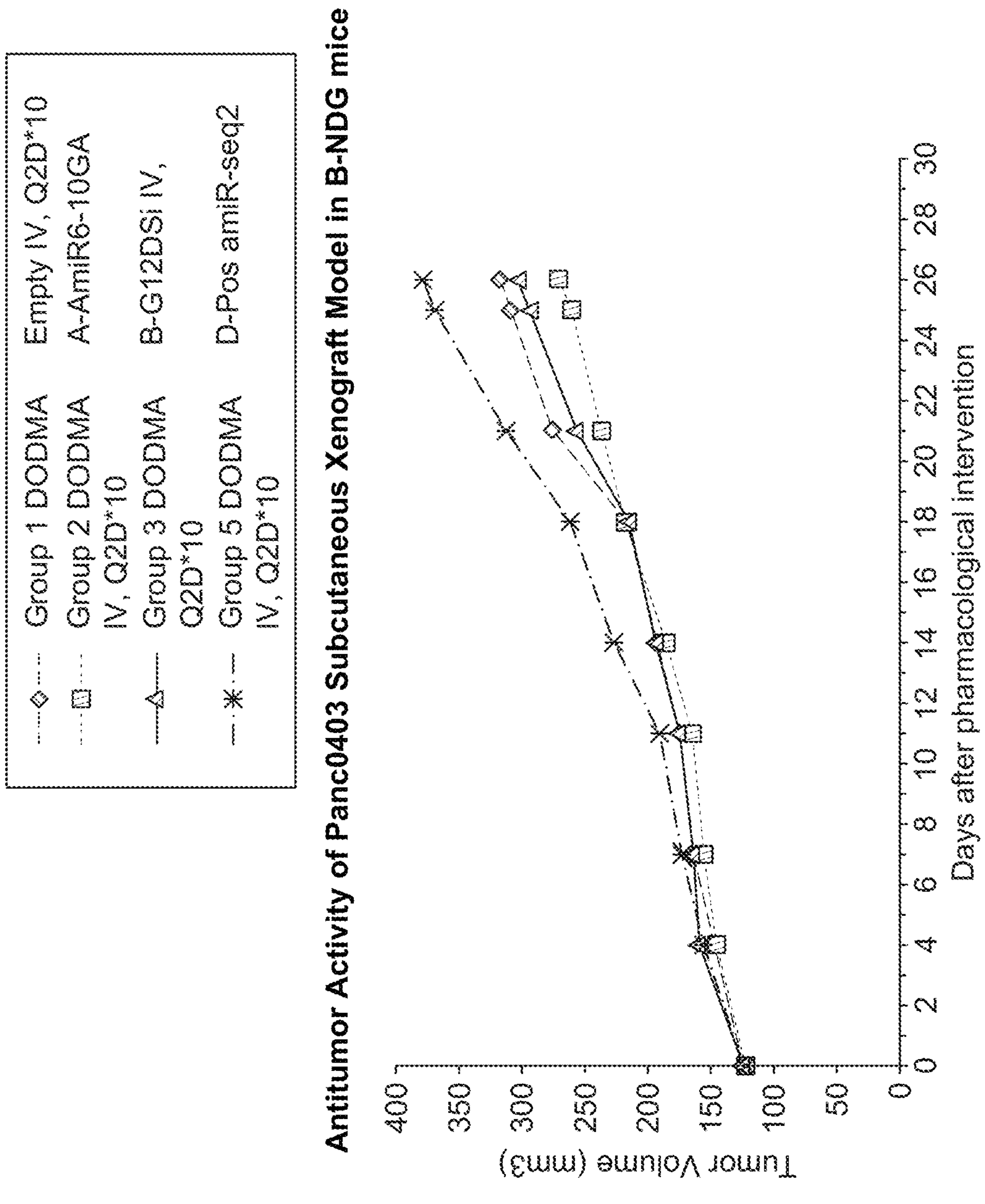
FIG. 24. Antitumor activity of amiR/siRNA in DODMA-based LNPs in PAN0403 xenograft model.
Figure 25:
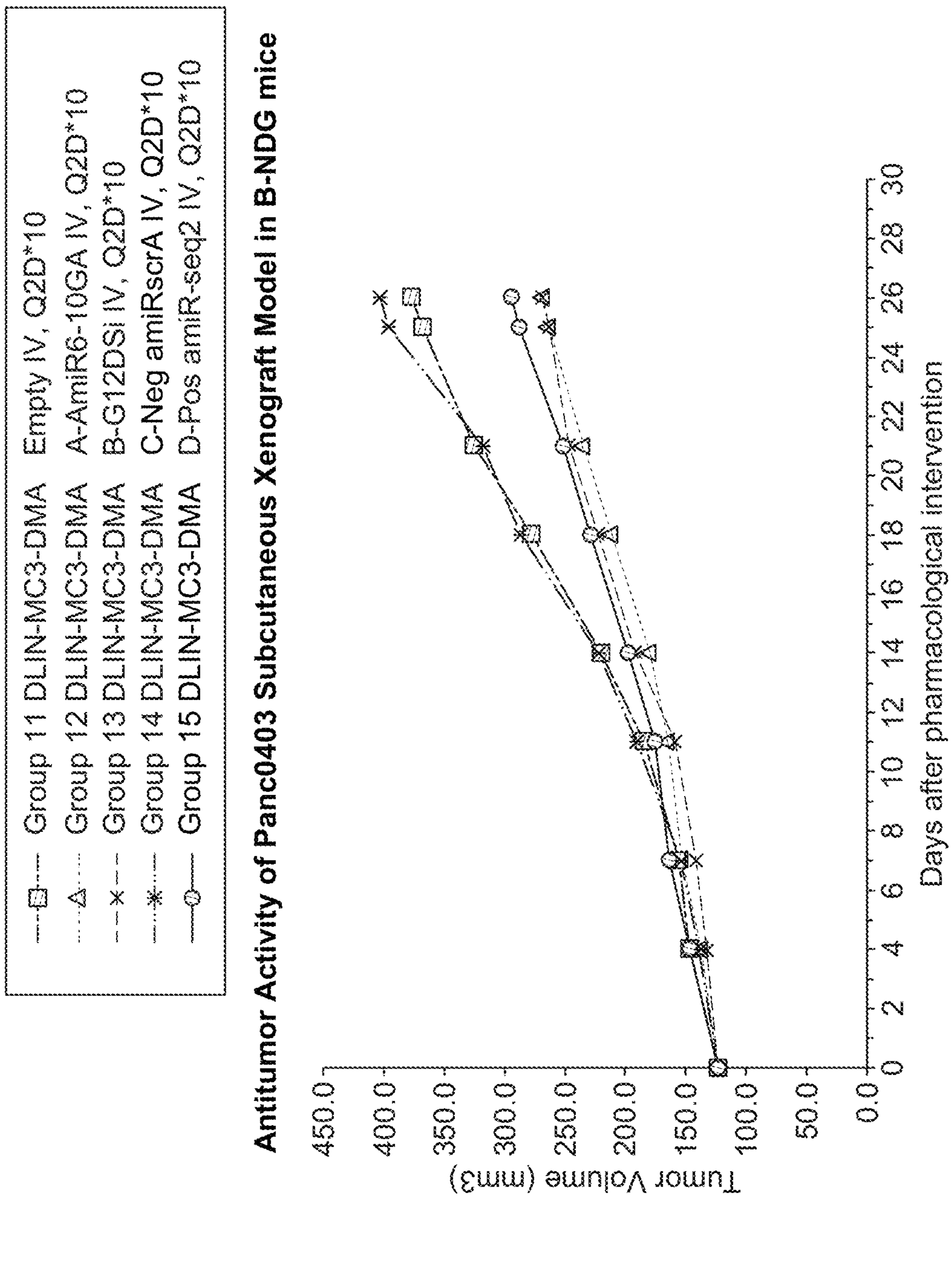
FIG. 25. Antitumor activity of amiR/siRNA in DLInMC3DMA-based LNPs in PAN0403 xenograft model.
Figure 26:
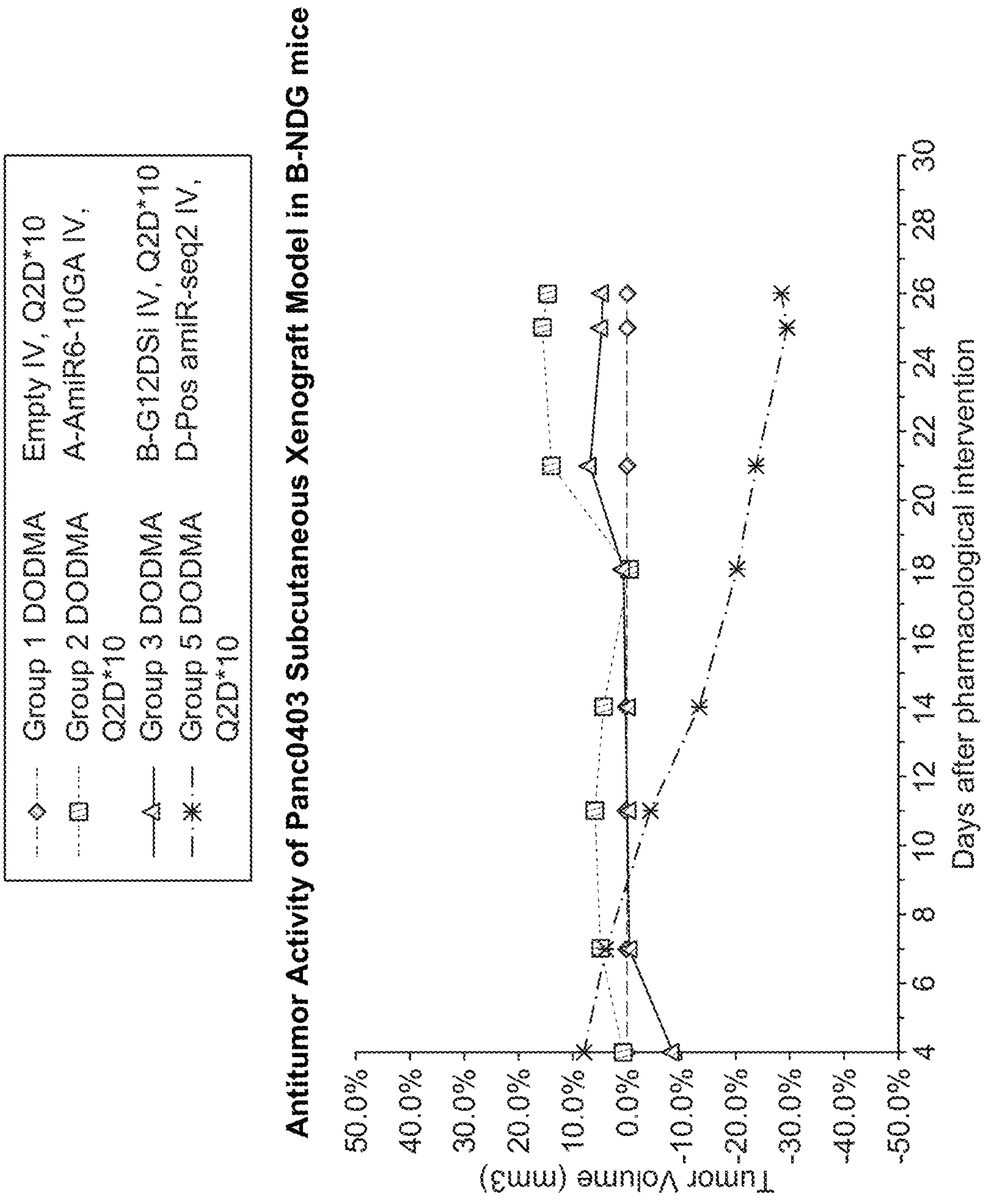
FIG. 26. Tumor growth inhibition by amiR/siRNA in DODMA-based LNPs in PAN0403 xenograft model. A positive value indicates tumor inhibition relative to empty LNPs.
Figure 27:
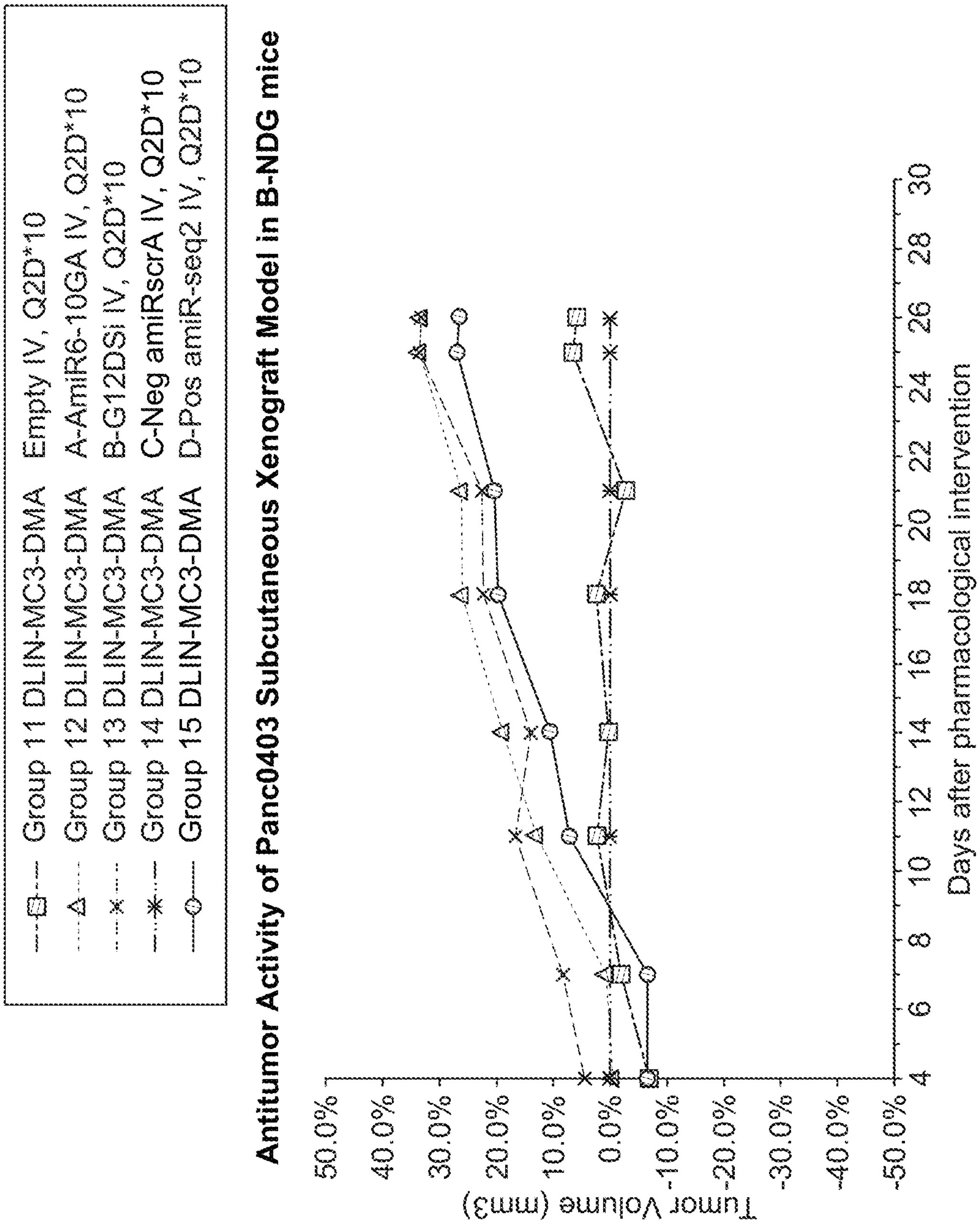
FIG. 27. Tumor growth inhibition by amiR/siRNA in DlinMC3DMA-based LNPs in PAN0403 xenograft model. A positive value indicates tumor inhibition relative to LNP-loaded scramble control.

The data obtained are illustrated in FIGS. 24-25. The tumor growth inhibition (TGI) values are provided in FIGS. 26-27.

The data showed that the LNP formulation has an important impact on tumor growth inhibition. With LNPs based on DODMA, the best performing amiR6-10GA produced a TGI of 15% over vehicle control ($p<0.01$). In contrast, the Seq2 siRNA was shown to promote tumor growth (TGI=−28%). This shows that the amiR6-10GA and 12Dsi were both superior to Seq2, the non-selective siRNA reported in the literature.

With the DLinMC3DMA/DOPE/PEG2000-DMG formulation, a TGI in excess of 33% was obtained with both amiR6-10GA and G12Dsi treatments relative to LNPs loaded with scrambled control ($p=0.0001$ for both agents).

TGI can be further improved by further increasing the dosage by increasing the concentration of amiR/siRNA-LNPs. Concentration of the LNPs can be readily accomplished by tangential-flow diafiltration (TFF), which has already been performed in the lab without issue. The LNPs loaded with amiR and siRNA described above can be further combined with other agents, such as chemotherapy, kinase inhibitors, angiogenesis inhibitors, and immunocheck point inhibitors to achieve an even higher TGI values.

Additional Analysis of Results

For the DlinMC3DMA-based LNP, targeted APIs (amiR6-10GA and G12Dsi are better than controls (empty LNPs and LNP-scramble control), with the margin of improvement being greater in vivo than in vitro.

DlinDMA-based LNPs were not selected for in vivo testing because of poor in vitro results.

In vitro, there are the following observations:

1. Mutant/WT selectivity is significantly greater for targeted APIs (e.g., amiR6-10GA and siRNA-12Dsi) compared to scramble control (tested with biomarker as well as viability studies in Panc0403 vs BxPC-3 cell lines). The seq2 siRNA was found to be cytotoxic toward HUVEC cells. This means there is greater potential for further improving TGI with the newly designed amiR and siRNA to improve by dose escalation because the MTD would be greater.
2. Scramble control (transfected, no LNP) is much less effective in downregulating biomarkers than targeted APIs
3. Scramble control (transfected, no LNP) has significantly lower efficacy than targeted APIs
4. Literature-reported mutant-specific siRNA (EFTX) is less selective than our targeted APIs (transfected, no LNP)

| Seq ID | Oligo name | Sequence (guide strand) |
|---|---|---|
| 1 | amiR3 | rCrCrA rUrCrA rGrCrA rGrGrA rArCrU rArCrC rArCrA rA |
| 2 | amiR3T | rCrCrA rUrCrA rGrCrA rGrGrA rArCrU rArCrC rArCrA rATT |
| 3 | amiR6 | rArCrG rCrCrA rUrCrU rCrGrU rCrCrA rArCrU rArCrC rA |
| 4 | amiR6T | rArCrG rCrCrA rUrCrU rCrGrU rCrCrA rArCrU rArCrC rATT |
| 5 | amiRscr | rGrUrU rGrGrA rGrGrC rGrGrU rArUrG rUrGrA rGTT |
| 6 | amiR3a | mC*rCmA* rUmC*rA mG*rCrA rGrGrA rArCrU rArCrC rA*rC*rA* rA |
| 7 | amiR6a | mA*rCmG* rCmC*rA* mUrCrU rCrGrU rCrCrA rArCrU rA*rC*rC* rA |
| 8 | amiR6-11CU | rA*rC*rG rCrCrA rUrCrA **rGrU**rU rCrCrA rArCrU rArCrC rA*T*T |
| 9 | amiR-10GA | rA*rC*rG rCrCrA rUrCrA **rArCrU** rCrCrA rArCrU rArCrC rA*T*T |
| 10 | EFTX-D1 | rUrUrG rCrCrU rArCrG rUrCrA rUrArA rGrCrU rC |
| 11 | G12Dsi | rU*rU*rG rCrCrU rArCrG rCrCrA rUrCrA rGrCrU rC*T*T |
| 12 | G12Dsi-4CA | rU*rU*rG rArCrU rArCrG rCrCrA rUrCrA rGrCrU rC*T*T |
| 13 | sikras 14 | rC*rU*rC rUrUrG rCrCrU rArCrG rCrCrA rUrCrA rG*T*T |
| 14 | amiR6-G12S<br>amiR6-G12S no | CGCCACUA**CGA**CCAACUACCAC |
| 15 | bulge<br>amiR6-G12S- | CGCCACUA**GCU**CCAACUACCAC |
| 16 | 10UC<br>amiR6-G12S- | CGCCACUA**GCC**CCAACUACCAC |
| 17 | 11CU | CGCCACUA**GCU**UCAACUACCAC |

-continued

| Seq ID | Oligo name | Sequence (guide strand) |
|---|---|---|
| 18 | G12Csi | UUGCCUACGCCA**CA**AGCUC |
| 19 | G12Csi-4CA | UUG**A**CUACGCCA**CA**AGCUC |
| 20 | scr (control) | UUCUCCGAACGUGUCACGU |
| 21 | Seq2 | rGrUrCrUrCrUrUrGrGrArUrArUrUrCrUrCrGrA |

All nucleotides are RNA, * denotes phosphorothioate linkages, mN indicates 2'-O-methyl-substituted nucleotides.

The invention claimed is:

1. An artificial miRNA (amiR) duplex for targeting mutants of kras, whose guide strand sequence follows the following rules: the $7^{th}$ nt matches comprising the mutant target sequence (mismatched against the WT sequence), wherein the rest of the amiR has one additional mismatch comprising the corresponding target sequence in either position 10 or position 11.

2. An artificial miRNA with SEQ ID 8 and 9 for selective targeting of KRAS G12D.

3. The artificial miRNA of claim 1 in which the RNA duplex contains chemical modifications to enhance its nuclease stabilty and efficacy of gene silencing.

4. An siRNA duplex for targeting of mutant of kras, whose target sequence is from the $2^{nd}$ nt of codon 10 to the $2^{nd}$ nt of codon 16, whose guide strand sequence contains 0-1 nt mismatch (mismatch at position 4 with C to A substitution) with the point mutated target sequence and 1-2 nt mismatch against kras WT (position 4 and the site of the point mutation).

5. An siRNA comprising SEQ ID 11 and 12 for selective targeting of KRAS G12D.

6. The siRNA of claim 4 in which the RNA duplex contains chemical modifications to enhance nuclease stabilty and efficacy of gene silencing.

7. The artificial miRNA of any of claims 1-3 or the siRNA of any of claims 4-6, for which the kras mutation target is G12C, G12S, G12V, and G13D.

8. The RNA duplex of claim 1, in which delivery is accomplished through incorporation into a nanoparticle.

9. The RNA duplex of claim 8 in which the said nanoparticle is a lipid nanoparticle-containing one ionizable lipid and a releasable PEG-modified lipid.

10. The RNA duplex of claim 9, in which the lipid compostion is of ionizable lipid/DOPE/cholesterol/$PEG_{2000}$-DMG at a ratio 46:26:26:2 and the ionizable lipid is selected from DODMA, DLin-DMA and DLin-MC3-DMA.

11. A pharmaceutical composition of claim 1 and a pharmaceutically acceptable carrier.

12. A method for treatment of neoplastic diseases associated with kras point mutations, comprising administering the artificial miRNA of any of claims 1-3 or the siRNA of any of claims 4-6 to a subject in need thereof.

13. The method of claim 12, for which the kras mutation target is G12C, G12S, G12V, and G13D.

14. The method of 12, for which the neoplastic diseases are selected from pancreatic cancer, lung cancer, and colorectal cancer.

15. A method for treating cancer with a KRAS mutation comprising administering the pharmaceutical composition of claim 11 to a subject in need thereof.

* * * * *